United States Patent [19]

Bourzat et al.

[11] Patent Number: 5,382,590
[45] Date of Patent: Jan. 17, 1995

[54] N-PHENYL-N-ACETAMIDOGLYCINAMIDES, THEIR PREPARATION AND MEDICAMENTS CONTAINING THEM

[75] Inventors: Jean-Dominique Bourzat, Vincennes; Marc Capet, Thiais; Claude Cotrel, Paris; Claude Guyon, Saint Maur des Fosses; Franco Manfre, Vitry sur Seine; Gérard Roussel, Soisy sur Seine, all of France

[73] Assignee: Rhone-Poulenc Rorer S.A., France

[21] Appl. No.: 867,690

[22] PCT Filed: Feb. 6, 1991

[86] PCT No.: PCT/FR91/00087
§ 371 Date: Jul. 8, 1992
§ 102(e) Date: Jul. 8, 1992

[87] PCT Pub. No.: WO91/12264
PCT Pub. Date: Oct. 22, 1991

[30] Foreign Application Priority Data

Feb. 9, 1990 [FR] France ............... 90 01553
Sep. 27, 1990 [FR] France ............... 90 11916
Oct. 12, 1990 [FR] France ............... 90 12594

[51] Int. Cl.⁶ ............... A61K 31/415; A61K 31/50; A61K 31/505; A61K 31/39; C07D 233/66; C07D 279/12; C07D 265/30; C07D 241/14
[52] U.S. Cl. ............... 514/396; 514/227.5; 514/227.8; 514/230.5; 514/249; 514/278; 514/326; 514/330; 514/331; 514/340; 514/561; 514/576; 514/597; 540/543; 540/596; 540/607; 544/52; 544/59; 544/60; 544/105; 544/353; 546/16; 546/19; 546/146; 546/166; 546/210; 546/226; 546/276; 548/335.5; 548/338.1; 548/407; 548/518
[58] Field of Search ............... 514/212, 224.2, 227.5, 514/227.8, 230.5, 249, 278, 326, 330, 331, 340, 359, 540, 561, 576, 596, 597, 598, 613, 615, 616, 396; 540/543, 596, 607; 544/52, 59, 60, 105, 353; 546/16, 19, 146, 166, 210, 226, 276, 328; 548/407, 518, 338.1, 335.5; 562/439; 564/48, 50, 51, 52, 53, 54, 153

[56] References Cited

U.S. PATENT DOCUMENTS 4,645,678 2/1987 Nofre et al. ............... 562/439

FOREIGN PATENT DOCUMENTS 0166355 1/1986 European Pat. Off. .
0175498 3/1987 European Pat. Off. .

OTHER PUBLICATIONS

Chem Abstr, vol. 113, No. 25, Dec. 17, 1990 "Synthesis of disulfides of N-(N-(2-mercaptobenzoyl)glycyl-)-N-alkyl/aryl-glycine;" p. 784, #231990r.
Chem Abstr, vol. 93, No. 3, Jul. 21, 1980 "Synthesis of peptices containing 1,2,3,4-tetrahydroquinoline-2-carboxylic acid," pp. 740-741 #26769c.

Primary Examiner—Mukund J. Shah
Assistant Examiner—Y. N. Gupta
Attorney, Agent, or Firm—Morgan & Finnegan

[57] ABSTRACT

Compounds of formula:

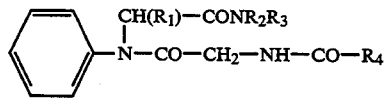

in which
$R_1$ represents a hydrogen atom or an alkyl, alkoxycarbonyl or an unsubstituted or substituted phenyl radical,
$R_2$ represents a hydrogen atom or an unsubstituted or substituted alkyl radical,
$R_3$ represents an alkyl, phenylalkyl, indanyl, cycloalkylalkyl or an unsubstituted or substituted phenyl radical, or
$R_2$ and $R_3$ form a heterocycle together with the nitrogen atom to which they are attached, and
$R_4$ represents an unsubstituted or substituted phenyl radical, a naphthyl, indolyl or quinolyl radical or a phenylamino radical in which the phenyl ring is unsubstituted or substituted, their preparation and medicaments containing them.

10 Claims, No Drawings

N-PHENYL-N-ACETAMIDOGLYCINAMIDES, THEIR PREPARATION AND MEDICAMENTS CONTAINING THEM

DESCRIPTION OF THE INVENTION

The present invention relates to compounds of formula

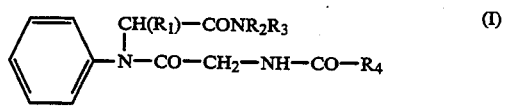

their preparation and medicaments containing them.

In the formula (I)

$R_1$ represents a hydrogen atom or an alkyl or alkoxycarbonyl radical or a phenyl radical (unsubstituted or substituted by one or more substituents chosen from halogen atoms and alkyl, alkoxy, alkylthio, nitro and amino radicals), $R_2$ represents a hydrogen atom or an alkyl radical (unsubstituted or substituted by an alkoxycarbonyl radical), $R_3$ represents an alkyl, phenylalkyl, indanyl, cycloalkylalkyl, phenyl (unsubstituted or substituted by one or more substituents chosen from halogen atoms and alkyl, alkoxy, alkylthio and dialkylamino radicals) or quinolyl radical, or $R_2$ and $R_3$ form, together with the nitrogen atom to which they are attached, a saturated or unsaturated monocyclic or polycyclic heterocycle containing 4 to 9 carbon atoms and one or more heteroatoms (O,S,N) and which is unsubstituted or substituted by one or more alkyl, alkoxycarbonyl, dialkylcarbamoyl, phenyl or alkoxy radicals or, in combination with a carbon atom of the heterocycle, a monocyclic spiro ring having 4 or 5 members and which may contain one or more heteroatoms (O,S,N), $R_4$ represents a phenyl radical (unsubstituted or substituted by one or more substituents chosen from halogen atoms and alkyl, alkoxy and alkylthio radicals), a naphthyl, indolyl or quinolyl radical or a phenylamino radical in which the phenyl ring is unsubstituted or substituted by one or more substituents chosen from halogen atoms and alkyl, alkoxy, alkylthio, hydroxyl, monohydroxyalkyl or polyhydroxyalkyl, nitro, amino, acyl, cyano, sulphamoyl, trifluoromethylsulphonamido, carbamoyl, benzoyl, carboxyl, alkoxycarbonyl, phenylhydroxymethyl, piperidino, hydroxyiminoalkyl, alkoxyiminoalkyl, alkylsulphinyl, hydroxyaminocarbonyl, alkoxyaminocarbonyl, 5-tetrazolyl, 5-tetrazolylalkyl, sulpho, —alk—O—CO—alk, —alk—O—alk, —alk—COOX, —O—alk—COOX, —alk-'—COOX, —CH=CH—COOX, —CO—COOX, —alk—SO$_3$H, —CH=CH—alk', —C(=NOH)—COOX and —S—alk—COOX radicals, alk represents an alkyl or alkylene radical, alk' represents a hydroxyalkylene or hydroxyalkyl radical, and X represents a hydrogen atom or an alkyl radical, with the proviso that, when $R_1$ represents a hydrogen atom, $R_4$ represents a naphthyl or indolyl radical or a phenylamino radical in which the phenyl ring is unsubstituted or substituted by an alkyl, alkoxy, alkylthio, nitro or hydroxyl radical or by one or two halogen atoms, $R_2$ and $R_3$ cannot form, with the nitrogen atom to which they are attached, a 1-pyrrolidinyl radical unsubstituted or substituted by an alkyl radical or $R_2$ and $R_3$ cannot represent alkyl radicals.

In the above definitions and those which will be given below, unless indicated to the contrary, the alkyl, alkylene and alkoxy radicals and moieties contain 1 to 4 carbon atoms in a straight or branched chain, the cycloalkyl moieties contain 3 to 6 carbon atoms and the acyl radicals contain 2 to 4 carbon atoms.

In formula (I), the halogen atoms are preferably chlorine, bromine or fluorine atoms.

When $R_2$ and $R_3$ form a heterocycle with the nitrogen atom to which they are attached, said heterocycle is preferably a piperidino (unsubstituted or substituted by at least one alkyl, phenyl, alkoxycarbonyl or dialkylcarbamoyl radical), 1-perhydroazepinyl, 1,2,3,6-tetrahydro-1-pyridyl, 1,2,3,4-tetrahydro-1-quinolyl, 1-pyrrolidinyl, 3,4-dihydro-1,4-2H-benzoxazin-4-yl, 3,4-dihydro-1,4-2H-benzothiazin-4-yl, N-alkyl-1,2,3,4-tetrahydro-1-quinoxalinyl, 1-perhydroquinolyl, 1,2,3,4-tetrahydro-2-isoquinolyl, 8-azaspiro[4,5]decan-8-yl, 8-aza-1,4-dioxaspiro[4,5]decan-8-yl, 2- or 3-phenyl-1-pyrrolidinyl, thiomorpholino (unsubstituted or substituted by at least one alkyl radical) or 1-indolinyl ring.

The compounds of formula (I) containing one or more asymmetric centers possess isomeric forms. The racemates and enantiomers of these compounds also form part of the invention.

The compounds of formula (I) for which $R_4$ represents a phenylamino radical in which the phenyl ring is unsubstituted or substituted by one or more substituents chosen from halogen atoms and alkyl, alkoxy, alkylthio, nitro, acyl, cyano, sulphamoyl, benzoyl, alkoxycarbonyl, 5-tetrazolyl, 5-tetrazolylalkyl, trifluoromethylsulphonamido and —alk—O—alk radicals may be prepared by the action of an amino derivative of formula:

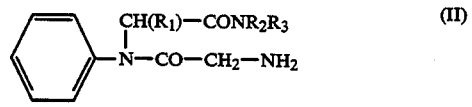

in which $R_1$, $R_2$ and $R_3$ have the same meanings as in formula (I), on an isocyanate of formula:

in which $R_5$ represents a phenyl radical optionally substituted by one or more substituents chosen from halogen atoms and alkyl, alkoxy, alkylthio, nitro, acyl, cyano, sulphamoyl, benzoyl, alkoxycarbonyl, 5-tetrazolyl, 5-tetrazolylalkyl, trifluoromethylsulphonamido and —alk—O—alk radicals.

This reaction generally takes place in an inert solvent such as tetrahydrofuran or dimethylformamide, a chlorinated solvent (chloroform or methylene chloride for example) or an aromatic solvent (benzene or toluene for example) at a temperature of between 10° C. and the boiling point of the solvent.

The isocyanates of formula (III) may be obtained by application or adaptation of the method described by R. Richter et al., The Chemistry of Cyanates and Their Thio Derivatives, S. Patai, Part 2, Wiley New York (1977).

The amino derivatives of formula (II) may be obtained by application or adaptation of the method described by T. Wieland et al., Justus Leibigs Ann. Chem., 613, 84 (1958) or by adaptation of Gabriel's method (Gibson et al., Angew. Chem. Int. Ed., 7, 919 (1968)), which comprises reacting hydrazine hydrate or N-methylhydrazine with a derivative of formula:

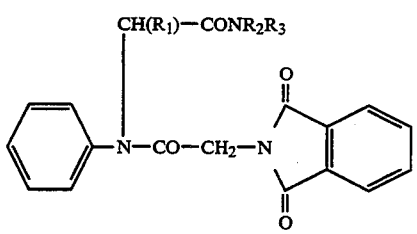

in which $R_1$, $R_2$ and $R_3$ have the same meanings as in formula (I).

This reaction preferably takes place in an inert solvent such as an alcohol (methanol, ethanol or propanol for example) at a temperature between 0° C. and the boiling point of the solvent.

The derivatives of formula (IV), with the exception of those for which $R_1$ represents an alkoxycarbonyl radical, may be obtained by the action of an amine of formula:

$$HNR_2R_3 \quad (V)$$

in which $R_2$ and $R_3$ have the same meanings as in formula (I), on an acid of formula:

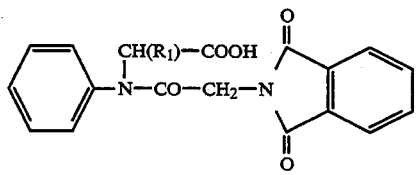

in which $R_1$ has the same meanings as above, or a reactive derivative of this acid.

When the acid is used, the reaction is carried out in the presence of a peptide condensing agent such as a carbodiimide (for example dicyclohexylcarbodiimide) or N,N'-diimidazolecarbonyl in an inert solvent such as an ether (for example THF or dioxane), an amide (for example DMF) or a chlorinated solvent (for example methylene chloride, dichloroethane or chloroform) at a temperature between 0° C. and the reflux temperature of the reaction mixture.

When a reactive derivative of the acid is used it is possible to react the anhydride, a mixed anhydride, an acid halide or an ester (which may be chosen from the activated or nonactivated esters of the acid).

The reaction is then carried out either in an organic medium, if appropriate in the presence of an acid acceptor such as a nitrogenous organic base (for example a trialkylamine, a pyridine, 1,8-diaza[5.4.0]-bicycluncdec-7-ene or 1,5-diaza[4.3.0]bicyclonon-5-ene), in a solvent such as indicated above, or a mixture of these solvents, at a temperature between 0° C. and the reflux temperature of the reaction mixture, or in a two-phase aqueous-organic medium in the presence of an alkali metal base or alkaline-earth metal base (sodium hydroxide or potassium hydroxide) or an alkali metal carbonate or bicarbonate or alkaline-earth metal carbonate or bicarbonate, at a temperature between 0° and 40° C.

The acids of formula (VI) may be obtained by hydrolysis of a corresponding ester of formula:

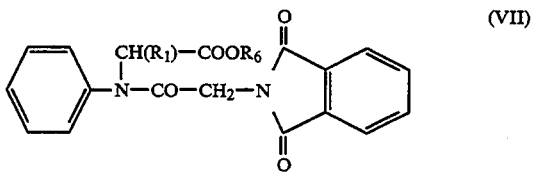

in which $R_6$ represents an alkyl radical and $R_1$ has the same meanings as above.

This reaction generally takes place by means of trifluoroacetic acid, in an inert solvent such as a chlorinated solvent (chloroform or dichloromethane for example), at the boiling point of the solvent.

The esters of formula (VII) may be obtained by the action of a derivative of formula:

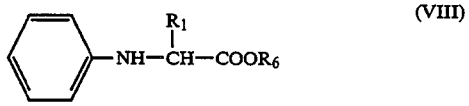

in which $R_1$ and $R_6$ have the same meanings as above, on a derivative of formula:

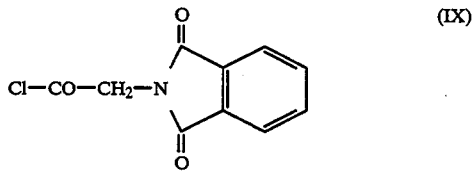

This reaction generally takes place in an inert solvent such as a chlorinated solvent (chloroform or 1,2-dichloroethane for example), in the presence of an alkaline agent such as an alkali metal bicarbonate, at a temperature between 20° C. and the boiling point of the solvent.

The derivative of formula (IX) may be obtained by application of the method described by W. Grassmann et al., Chem. Ber., 83, 244 (1950).

The derivatives of formula (VIII) may be obtained by the action of aniline on a derivative of formula:

in which Hal represents a halogen atom and $R_1$ and $R_6$ have the same meanings as above.

This reaction generally takes place in an inert solvent such as a chlorinated solvent (chloroform or dichloromethane for example), at the boiling point of the solvent.

The derivatives of formula (IV) may also be obtained by the action of a derivative of formula (IX) on an amine of formula:

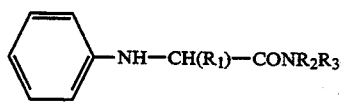 (XI)

in which $R_1$, $R_2$ and $R_3$ have the same meanings as in formula (I).

This reaction generally takes place under the same conditions as those described above for the reaction of a derivative of formula (IX) with a compound of formula (VIII).

The amines of formula (XI) may be obtained by the action of aniline on a derivative of formula:

$$Br-CH(R_1)-CONR_2R_3 \quad (XII)$$

in which $R_1$, $R_2$ and $R_3$ have the same meanings as in formula (I).

This reaction generally takes place under the same conditions as those described above for the reaction of aniline on a derivative of formula (X).

The derivatives of formula (XII) for which $R_1$ represents an alkoxycarbonyl radical may be obtained by bromination of a derivative of formula:

$$R_1-CH_2-CONR_2R_3 \quad (XIII)$$

in which $R_1$ represents an alkoxycarbonyl radical and $R_2$ and $R_3$ have the same meanings as in formula (I).

The reaction is generally carried out using bromine, if appropriate in the presence of acetamide.

The derivatives of formula (XIII) may be obtained by the action of alkyl hydrogen malonate or a reactive derivative of this acid on an amine of formula (V) in which $R_2$ and $R_3$ have the same meanings as in formula (I).

This reaction generally takes place under the conditions described above for the reaction of the amine of formula (V) with an acid of formula (VI).

The derivatives of formula (XII) for which $R_1$ represents a hydrogen atom, an alkyl radical or an optionally substituted phenyl radical may be obtained by the action of an acid chloride of formula:

$$Br-CH(R_1)-COCl \quad (XIV)$$

in which $R_1$ has the same meanings as above, on an amine of formula (V).

This reaction generally takes place in an inert solvent such as acetonitrile, dimethylformamide or tetrahydrofuran, in the presence of a tertiary amine such as a trialkylamine, at a temperature close to 25° C.

The compounds of formula (I) for which $R_4$ represents a phenylamino radical in which the phenyl ring is unsubstituted or substituted by one or more substituents chosen from halogen atoms and alkyl, alkylthio, 5-tetrazolylalkyl, 5-tetrazolyl, trifluoromethylsulphonamido, alkoxy, nitro, acyl, cyano, sulphamoyl, benzoyl, alkoxycarbonyl and —alk—O—alk radicals may also be prepared by the action of an amine of formula (XI) on an acid of formula:

$$HOOC-CH_2-NH-CO-R_4 \quad (XV)$$

in which $R_4$ has the same meanings as above.

This reaction generally takes place in an inert solvent such as a chlorinated solvent (chloroform or 1,2-dichloroethane for example), by means of thionyl chloride, at the boiling point of the solvent.

The acids of formula (XV) may be obtained by the action of an isocyanate of formula (III) on glycine.

This reaction generally takes place in an aqueous medium, in the presence of an alkaline agent such as an alkali metal bicarbonate, at a temperature between 15° and 30° C.

The compounds of formula (I) for which $R_4$ represents an unsubstituted or substituted phenylamino radical may also be prepared by the action of a derivative of formula

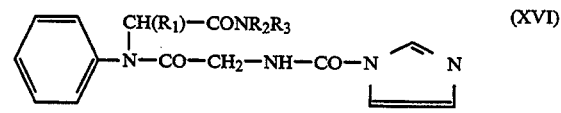 (XVI)

in which $R_1$, $R_2$ and $R_3$ have the same meanings as in formula (I), on an amine of formula:

$$H_2N-R_7 \quad (XVII)$$

in which $R_7$ represents a phenyl radical unsubstituted or substituted by one or more substituents chosen from halogen atoms and alkyl, alkoxy, alkylthio, hydroxyl, monohydroxyalkyl or polyhydroxyalkyl, nitro, amino, acyl, cyano, sulphamoyl, trifluoromethylsulphonamido, carbamoyl, benzoyl, carboxyl, alkoxycarbonyl, phenylhydroxymethyl, piperidino, hydroxyiminoalkyl, alkoxyiminoalkyl, alkylsulphinyl, hydroxyaminocarbonyl, alkoxyaminocarbonyl, 5-tetrazolylalkyl, 5-tetrazolyl, sulpho, —alk—O—CO—alk, —alk—O—alk, —alk—COOX, —O—alk—COOX, —alk'—COOX, —CH═CH—COOX, —CO—COOX, —alk—SO$_3$H, —CH═CH—alk', —C(═NOH)—COOX and —S—alk—COOX radicals.

This reaction generally takes place in an inert solvent such as tetrahydrofuran or dimethylformamide, a chlorinated solvent, or an aromatic solvent (benzene or toluene for example) at a temperature between 20° C. and the boiling point of the solvent.

For the amines of formula (XVII) comprising at least one sulpho radical, it is preferable to protect the sulpho functional group by any method known to those skilled in the art, for example in the form of a tetra-n-butylammonium salt, and then to regenerate this functional group.

The derivatives of formula (XVI) may be obtained by the action of an amino derivative of formula (II) on N,N'-carbonyldiimidazole.

This reaction takes place in an inert solvent such as tetrahydrofuran or dimethylformamide or a chlorinated or aromatic solvent, at a temperature between 10° C. and 50° C. It is possible not to isolate the compound of formula (XVI) and to react it in situ with the amine of formula (XVII).

The amines of formula (XVII) are commercially available compounds or may be obtained by application or adaptation of the methods described by G. J. Esselen et al., J. Am. Chem. Soc., 36, 322 (1914); G. Adriant et al., Bull. Soc. Chim. Fr., 1511 (1970); W. A. Jacobs et al., J. Am. Chem. Soc., 39, 2428, (1917); J. Am. Chem. Soc., 39, 1438 (1917) and in the examples.

The compounds of formula (I) for which $R_4$ represents a phenylamino radical in which the phenyl ring is substituted by at least one carboxyl, —alk—COOH, —O—alk—COOH, —alk'—COOH, —CH=CH—COOH, —CO—COOH, —C(=NOH)—COOH or —S—alk—COOH radical may also be prepared by hydrolysis of the corresponding esters.

This hydrolysis generally takes place by means of a base such as sodium hydroxide or potassium hydroxide, in an inert solvent such as tetrahydrofuran, dioxane, water or a mixture of these solvents, at a temperature between 20° and 40° C., or by means of trifluoroacetic acid, in an inert solvent such as a chlorinated solvent (dichloromethane, chloroform or 1,2-dichloroethane for example), at a temperature between 20° C. and the boiling point of the solvent.

The compounds of formula (I) for which $R_4$ represents a phenylamino radical in which the phenyl ring is substituted by at least one amino radical, with the exception of those for which $R_1$ represents a phenyl radical substituted by at least one nitro radical, may also be obtained by reduction of the corresponding nitro derivatives.

This reduction takes place by any method known to those skilled in the art which enables a nitro group to be converted to an amino group. Preferably, the reduction is carried out using hydrogen, in the presence of a catalyst such as palladium-on-charcoal, platinum oxide or Raney nickel, in an inert solvent such as an alcohol (methanol or ethanol for example) at a temperature between 20° and 100° C.

The compounds of formula (I) for which $R_4$ represents a phenylamino radical in which the phenyl ring is substituted by at least one phenylhydroxymethyl radical may also be obtained by reduction of the corresponding benzoyl compounds.

This reduction generally takes place by means of a reducing agent such as sodium borohydride, in an inert solvent such as tetrahydrofuran, an alcohol (methanol or ethanol for example) or a mixture of these solvents, at a temperature close to 25° C.

The compounds of formula (I) for which $R_4$ represents a phenylamino radical in which the phenyl ring is substituted by at least one acyl radical may also be prepared by oxidation of the corresponding hydroxyalkyl compounds.

This oxidation preferably takes place by means of an oxidizing agent such as manganese dioxide, in an inert solvent such as a chlorinated solvent chloroform or methylene chloride for example), at a temperature close to 25° C.

The compounds of formula (I) for which R4 represents a phenylamino radical in which the phenyl ring is substituted by at least one hydroxyiminoalkyl, alkoxyiminoalkyl, hydroxyaminocarbonyl or alkoxyaminocarbonyl or —C(=NOH)—COOX radical in which X represents an alkyl radical may also be obtained by the action of the corresponding derivatives for which $R_4$ represents a phenylamino radical in which the phenyl ring is substituted by at least one acyl, formyl or alkoxycarbonyl or —CO—COOX radical in which X represents an alkyl radical, on a derivative of formula:

$$H_2N—OR_8 \qquad (XVIII)$$

in which $R_8$ represents a hydrogen atom or an alkyl radical.

This reaction generally takes place in an inert solvent such as an alcohol (methanol or ethanol for example), water or a mixture of these solvents, at the boiling point of the solvent and if appropriate in the presence of a base such as pyridine.

The formyl-containing intermediate derivatives may be obtained by oxidation of the hydroxymethyl derivatives by adaptation of the method described above for the preparation of the acyl compounds and of the method described in the examples.

The compounds of formula (I) for which $R_4$ represents a phenylamino radical in which the phenyl ring is substituted by at least one alkylsulphinyl radical may also be prepared by oxidation of the corresponding alkylthio derivatives.

This oxidation preferably takes place by means of m-chloroperbenzoic acid, in an inert solvent such as a chlorinated solvent (chloroform or methylene chloride for example), at a temperature close to 25° C.

The compounds of formula (I) for which $R_4$ represents a phenylamino radical in which the phenyl ring is substituted by at least one —alk—O—CO—alk radical may also be prepared by the action of an acyl chloride on the corresponding hydroxyalkyl compounds.

This reaction generally takes place in an anhydrous solvent such as a chlorinated solvent (chloroform or methylene chloride for example), in the presence of a base such as trialkylamine, at a temperature between 0° and 50° C.

The compounds of formula (I) for which $R_4$ represents a phenylamino radical in which the phenyl ring is substituted by at least one trifluoromethylsulphonamido radical may also be prepared by the action of trifluoromethanesulphonic anhydride on a corresponding compound for which $R_4$ represents a phenylamino radical in which the phenyl ring is substituted by at least one amino radical.

This reaction generally takes place in an inert solvent such as a chlorinated solvent (methylene chloride or chloroform) in the presence of a nitrogenous base such as triethylamine at a temperature close to 25° C.

The compounds of formula (I) for which $R_4$ represents an optionally substituted phenyl radical, or a naphthyl, indolyl or quinolyl radical, may be prepared by the action of an amino derivative of formula (II) on a derivative of formula:

$$HOOC—R_4 \qquad (XIX)$$

in which $R_4$ has the same meanings as above, or a reactive derivative of this acid.

This reaction takes place under the same conditions as those described above for the reaction of an amine of formula (V) on an acid of formula (VI).

It is understood by those skilled in the art that, in order to carry out the processes according to the invention which have been described above, it may be necessary to introduce protective groups for the amino functional groups in order to prevent side reactions. These functional groups may, for example, be blocked in the form of trifluoromethylacetamide and then regenerated by the action of ammoniacal methanol after having carried out the process according to the invention.

The enantiomers of the compounds of formula (I) containing at least one site of asymmetry may be obtained by resolution of the racemates, for example by chiral column chromatography using the method of W. H. Pirckle et al., Asymmetric Synthesis, Vol. 1, Academic Press (1983) or by synthesis from chiral precursors.

The compounds of formula (I) may be purified by the customary known methods, for example by crystallization, chromatography or extraction.

The compounds of formula (I) may optionally be converted to addition salts with an inorganic or organic acid by the action of such an acid in an organic solvent such as an alcohol, a ketone, an ether or a chlorinated solvent.

The compounds of formula (I) comprising a carboxyl, sulpho or alk—$SO_3H$ group may also be converted to metal salts or to addition salts with nitrogenous bases using methods known per se. These salts may be obtained by the action of a metal base (alkali metal base or alkaline-earth metal base for example), ammonia or an amine on a compound of formula (I) in a solvent such as an alcohol, an ether or water, or by exchange reaction with a salt of an organic acid. The salt formed is separated off by the customary methods.

These salts also form part of the invention.

Examples of pharmaceutically acceptable salts which may be mentioned are the addition salts with inorganic or organic acids (such as acetate, propionate, succinate, benzoate, fumarate, maleate, oxalate, methanesulphonate, isethionate, theophyllinacetate, salicylate, methylene-bis-$\beta$-oxynaphthoate, hydrochloride, sulphate, nitrate and phosphate), the salts with alkali metals (sodium, potassium or lithium) or with alkaline-earth metals (calcium or magnesium), the ammonium salt, the salts of nitrogenous bases (ethanolamine, trimethylamine, methylamine, benzylamine, N-benzyl-$\beta$-phenethylamine, choline, arginine, leucine, lysine or N-methylglucamine).

The compounds of formula (I) have valuable pharmacological properties. These compounds have a strong affinity for cholecystokinin (CCK) and for gastrin receptors and are therefore useful in the treatment and the prevention of disorders associated with CCK and gastrin in the nervous system and the gastrointestinal system.

Thus, these compounds may be used for the treatment and the prevention of psychoses, anxiety complaints, Parkinson's disease, tardive dyskinesia, irritable colon syndrome, acute pancreatitis, ulcers and disorders of the intestinal motility and certain tumours of the lower oesophagus, the colon and the intestine and as an appetite regulator.

These compounds also have a boosting effect on the analgesic activity of narcotic and nonnarcotic medicaments.

The affinity of the compounds of formula (I) for the CCK receptors has been determined using a technique inspired by that of A. Saito et al. (J. Neuro. Chem., 37,483–490 (1981)) in the cerebral cortex and in the pancreas.

In these tests, the $IC_{50}$ of the compounds of formula (I) is generally less than or equal to 1000 nM.

Moreover, it is known that products which recognize central CCK receptors have a similar specificity for gastrin receptors in the gastrointestinal tract (Boch et al., J. Med. Chem., 32, 16–23 (1989); Reyfeld et al, Am. J. Physiol. 240, G255–266 (1981); Beinfeld et al., Neuropeptides 3, 411–427 (1983)).

The compounds of formula (I) have a low toxicity. Their $LD_{50}$ is generally higher than 40 mg/kg administered subcutaneously to mice.

Compounds of formula (I) which are of particular value are those for which $R_1$ represents a hydrogen atom, $R_2$ represents an alkyl radical and $R_3$ represents a phenyl radical, or $R_2$ and $R_3$ form, with the nitrogen atom to which they are attached, a piperidino radical substituted by at least one alkyl radical, or a thiomorpholino radical substituted by at least one alkyl radical, and $R_4$ represents a phenylamino radical in which the phenyl ring is substituted by one or more substituents chosen from hydroxyl, carboxyl, hydroxyiminoalkyl, —alk—COOH, alkyl, alkylthio, monohydroxyalkyl and —C(=NOH)—COOH radicals.

The following are the preferred compounds:
2-{2-[3-(3-hydroxymethylphenyl)ureido]-N-phenylacetamido}-N-methyl-N-phenylacetamide,
(E)-2-{2-{3-[3-(1-hydroxyiminoethyl)phenyl]ureido}-N-phenylacetamido}-N-methyl-N-phenylacetamide,
3-{3-[N-(N-methyl-N-phenylcarbamoylmethyl)-N-phenylcarbamoylmethyl]ureido}benzoic acid,
2-{2-{3-[3-(2-hydroxyethyl)phenyl]ureido}-N-phenylacetamido}-N-methyl-N-phenylacetamide,
5-{3-[N-(N-methyl-N-phenylcarbamoylmethyl)-N-phenylcarbamoylmethyl]ureido}salicylic acid,
3-{3-[N-(N-methyl-N-phenylcarbamoylmethyl)-N-phenylcarbamoylmethyl]ureido}phenylacetic acid,
N-methyl-2-{2-[3-(3-methylthiophenyl)ureido]-N-phenylacetamido}-N-phenylacetamide,
(RS)-N-[2-(3,3-dimethylpiperidino)-2-oxoethyl]-2-{3-[3-(1-hydroxyethyl)phenyl]ureido}-N-phenylacetamide,
N-[2-(3,3-dimethylpiperidino)-2-oxoethyl]-2-[3-(3-methylthiophenyl)ureido]-N-phenylacetamide,
(E)-2-{2-[3-(3-hydroxyiminomethylphenyl)ureido]-N-phenylacetamido}-N-methyl-N-phenylacetamide,
3-{3-{3-[N-(N-methyl-N-phenylcarbamoylmethyl)-N-phenylcarbamoylmethyl]ureido}phenyl}propionic acid,
2-hydroxyimino-2-{3-{3-[N-(N-methyl-N-phenylcarbamoylmethyl)-N-phenylcarbamoylmethyl]ureido}phenyl}acetic acid (A form), and
N-[2-(2,2-dimethylthiomorpholino)-2-oxoethyl]-2-[3-(3-methylphenyl)ureido]-N-phenylacetamide.

EXAMPLE

The following examples, given on a non-limiting basis, show how the invention can be implemented.

EXAMPLE 1

0.15 g of 3-methylphenyl isocyanate is added to a solution of 0.3 g of 2-(2-amino-N-phenylacetamido)-N-phenylacetamide in 10 cm³ of anhydrous tetrahydrofuran, at a temperature close to 25° C. The suspension obtained is stirred for 12 hours at a temperature close to 25° C. and the insoluble product is separated off by filtration. After recrystallization from acetonitrile, 0.3 g of 2-{2-[3-(3-methylphenyl)ureido]acetamido}-N-phenylacetamide melting at 210° C. are obtained.

2-(2-Amino-N-phenylacetamido)-N-phenylacetamide may be prepared in the following way: 0.29 g of hydrazine hydrate is added to a solution of 1.2 g of 2-(N-phenyl-2-phthalimidoacetamido)-N-phenylacetamide in 15 cm³ of methanol. The reaction mixture is stirred under reflux for 2 hours. After cooling and adding 5 cm³ of a 4N aqueous hydrochloric acid solution, the insoluble product is separated off by filtration. The filtrate is concentrated to dryness under reduced pressure (2.7 kPa) at 30° C. The residue obtained is dissolved in 10 cm³ of distilled water and the solution obtained is then washed with 10 cm³ of diethyl ether, rendered alkaline with 0.5 g of sodium hydroxide pellets and extracted with twice 20 cm³ of ethyl acetate. The combined organic phases are dried over magnesium sulphate and then concentrated to dryness under reduced pressure (2.7 kPa) at 30° C. 0.3 g of 2-(2-amino-N-phenylacetamido)-N-phenylacetamide is thus obtained in the form of an oil which is used as such in the subsequent syntheses.

2-(N-Phenyl-2-phthalimidoacetamido)-N-phenylacetamide may be prepared in the following way: 0.7 g of oxalyl dichloride and then one drop of dimethylformamide are added to a suspension of 1.7 g of 2-(N-phenyl-2-phthalimidoacetamido)acetic acid in 25 cm³ of 1,2-dichloroethane. The mixture is stirred for 2 hours at a temperature close to 25° C. and 1.12 g of aniline in solution in 10 cm³ of 1,2-dichloroethane are then added. The solution obtained is stirred for 2 hours at a temperature close to 25° C. and then washed with twice 30 cm³ of distilled water, dried over magnesium sulphate and concentrated to dryness under reduced pressure (2.7 kPa) at 40° C. After recrystallization from acetonitrile, 1.2 g of 2-(N-phenyl-2-phthalimidoacetamido)-N-phenylacetamide melting at 140° C. are obtained.

2-(N-Phenyl-2-phthalimidoacetamido)acetic acid may be prepared in the following way: 17.9 g of trifluoroacetic acid are added to a solution of 8 g of tert-butyl 2-(N-phenyl-2-phthalimidoacetamido)acetate in 30 cm³ of dichloromethane. The solution obtained is stirred under reflux for one hour and then concentrated to dryness under reduced pressure (2.7 kPa) at 40° C. After recrystallization from diisopropyl ether, 5.9 g of 2-(N-phenyl-2-phthalimidoacetamido)acetic acid melting at 224° C. are obtained.

tert-Butyl 2-(N-phenyl-2-phthalimidoacetamido)acetate may be prepared in the following way: 92.4 g of sodium bicarbonate are added to a solution of 207 g of tert-butyl N-phenylglycinate in 500 cm³ of 1,2-dichloroethane. The suspension is stirred at a temperature close to 5° C. and a solution of 223 g of 2-phthalimidoacetyl chloride in 1100 cm³ of 1,2-dichloroethane is added. The reaction mixture is stirred under reflux for 4 hours. After separating off the insoluble product by filtration, the filtrate is washed with 300 cm³ of distilled water, dried over magnesium sulphate and concentrated to dryness under reduced pressure (2.7 kPa) at 40° C. After recrystallization from acetonitrile, 236 g of tert-butyl 2-(N-phenyl-2-phthalimidoacetamido)acetate melting at 128° C. are obtained.

tert-Butyl N-phenylglycinate may be prepared in the following way: 58 g of tert-butyl bromoacetate are added to a solution of 56 g of aniline in 600 cm³ of 1,2-dichloroethane and the solution obtained is stirred under reflux for 48 hours. After cooling, the insoluble product is separated off by filtration and the filtrate is washed with 200 cm³ of a 0.1N aqueous hydrochloric acid solution and with 3 times 200 cm³ of distilled water. The organic phase is dried over magnesium sulphate and then concentrated to dryness under reduced pressure (2.7 kPa) at 40° C. 54 g of tert-butyl N-phenylglycinate are thus obtained in the form of an oil which is used as such in the subsequent syntheses.

2-Phthalimidoacetyl chloride may be prepared by the method described by W. Grassmann and E. Schulte-Uebling, Chem. Ber., 83, 244, (1950).

EXAMPLE 2

The procedure is analogous to that described in Example 1 but 0.9 g of 2-(2-amino-N-phenyl-acetamido)-N-methyl-N-phenylacetamide and 0.4 g of 3-methylphenyl isocyanate are used as the starting material. After recrystallization from a mixture of diethyl ether and ethyl acetate (60-40 by volume), 0.4 g of N-methyl-N-phenyl-2-{2-[3-(3-methylphenyl)ureido]-N-phenyl-acetamido}acetamide melting at 168° C. is obtained.

2-(2-Amino-N-phenylacetamido)-N-methyl-N-phenylacetamide may be prepared in a manner analogous to that described in Example 1 for the preparation of 2-(2-amino-N-phenylacetamido)-N-phenylacetamide, but using 1.4 g of N-methyl-N-phenyl-2-(N-phenyl-2-phthalimidoacetamido)acetamide and 0.25 g of hydrazine hydrate as the starting material. 0.9 g of 2-(2-amino-N-phenylacetamido)-N-methyl-N-phenylacetamide is thus obtained in the form of an oil which is used as such in the subsequent syntheses.

N-Methyl-N-phenyl-2-(N-phenyl-2-phthalimidoacetamido)acetamide may be prepared in a manner analogous to that described in Example 1 for the preparation of 2-(N-phenyl-2-phthalimidoacetamido)-N-phenylacetamide, but using 10.1 g of 2-(N-phenyl-2-phthalimidoacetamido)acetic acid, 3.9 g of oxalyl dichloride and 7.7 g of N-methylaniline as the starting material. After recrystallization from diisopropyl ether, 9.6 g of N-methyl-N-phenyl-(N-phenyl-2-phthalimidoacetamido)acetamide melting at 216° C. are obtained.

EXAMPLE 3

The procedure is analogous to that described in Example 1, but 2.2 g of 2-(2-amino-N-phenylacetamido)-N-(4-chlorophenyl)-N-methylacetamide and 0.87 g of 3-methylphenyl isocyanate are used as the starting material. The product obtained is purified by chromatography on 60 g of silica (0.065-0.200 mm) contained in a column 2.5 cm in diameter [eluent: methylene chloride/methanol (99-1 by volume)], collecting 20 cm³ fractions. Fractions 30 to 43 are combined and concentrated to dryness under reduced pressure (2.7 kPa) at 40° C. After recrystallization from acetonitrile, 1.0 g of N-(4-chlorophenyl)-N-methyl-2-{2-[3-(3-methylphenyl)ureido]-N-phenylacetamido}acetamide melting at 160° C. is obtained.

2-(2-Amino-N-phenylacetamido)-N-(4-chlorophenyl)-N-methylacetamide may be prepared in a manner analogous to that described in Example 1 for the preparation of 2-(2-amino-N-phenylacetamido)-N-phenylacetamide, but using 11 g of N-(4-chlorophenyl)-N-methyl-2-(N-phenyl-2-phthalimidoacetamido)acetamide and 2.4 g of hydrazine hydrate as the starting material. 6.6 g of 2-(2-amino-N-phenylacetamido)-N-(4-chlorophenyl)-N-methylacetamide are thus obtained in the form of an oil which is used as such in the subsequent syntheses.

N-(4-Chlorophenyl)-N-methyl-2-(N-phenyl-2-phthalimidoacetamido)acetamide may be prepared in a manner analogous to that described in Example 1 for the preparation of 2-(N-phenyl-2-phthalimidoacetamido)-N-phenylacetamide, but using 10.1 g of 2-(N-phenyl-2-phthalimidoacetamido)acetic acid, 3.9 g of oxalyl dichloride and 10.1 g of 4-chloro-N-methylaniline as the starting material. After recrystallization from diisopropyl ether, 11.0 g of N-(4-chlorophenyl)-N-methyl-2-(N-phenyl-2- phthalimidoacetamido)acetamide melting at 180° C. are obtained.

EXAMPLE 4

The procedure is analogous to that described in Example 1, but 1.2 g of 2-(2-amino-N-phenyl-acetamido)-N-(2,4-difluorophenyl)-N-methylacetamide and 0.46 g of 3-methylphenyl isocyanate are used as the starting material. The product obtained is purified by chromatography on 70 g of silica (0.065–0.200 mm) contained in a column 2.5 cm in diameter [eluent: dichloromethane/methanol (99-1 by volume)], collecting 15 cm³ fractions. Fractions 24 to 36 are combined and concentrated to dryness under reduced pressure (2.7 kPa) at 40° C. After recrystallization from diisopropyl ether, 0.6 g of N-(2,4-difluorophenyl)-N-methyl-2-{2-[3-(3-methylphenyl)ureido]-N-phenylacetamido}acetamide melting at 100° C. is obtained.

2-(2-Amino-N-phenylacetamido)-N-(2,4-difluorophenyl)-N-methylacetamide may be prepared in a manner analogous to that described in Example 1 for the preparation of 2-(2-amino-N-phenylacetamido)-N-phenylacetamide, but using 2.2 g of N-(2,4-difluorophenyl)-N-methyl-2-(N-phenyl-2-phthalimidoacetamido)acetamide and 0.47 g of hydrazine hydrate as the starting material. 1.2 g of 2-(2-amino-N-phenylacetamido)-N-(2,4-difluorophenyl)-N-methylacetamide are thus obtained in the form of an oil which is used as such in the subsequent syntheses.

N-(2,4-Difluorophenyl)-N-methyl-2-(N-phenyl-2-phthalimidoacetamido)acetamide may be prepared in a manner analogous to that described in Example 1 for the preparation of 2-(N-phenyl-2-phthalimidoacetamido)-N-phenylacetamide, but using 4.6 g of 2-(N-phenyl-2-phthalimidoacetamido)acetic acid, 1.7 g of oxalyl dichloride and 3.9 g of 2,4-difluoro-N-methylaniline as the starting material. The product obtained is purified by chromatography on 100 g of silica (0.065–0.200 mm) contained in a column 3.5 cm in diameter [eluent: dichloromethane/methanol (99-1 by volume)], collecting 20 cm³ fractions. Fractions 14 to 23 are combined and concentrated to dryness under reduced pressure (2.7 kPa) at 40° C. 2.2 g of N-(2,4-difluorophenyl)-N-methyl-2-(N-phenyl-2-phthalimidoacetamido)acetamide are obtained in the form of a meringue which is used as such in the subsequent syntheses.

EXAMPLE 5

The procedure is analogous to that described in Example 1, but 1.9 g of 2-(2-amino-N-phenylacetamido)-N-(4-methoxyphenyl)-N-methylacetamide and 0.77 g of 3-methylphenyl isocyanate are used as the starting material. The product obtained is purified by chromatography on 70 g of silica (0.065–0.200 mm) contained in a column 2.5 cm in diameter [eluent: ethyl acetate/cyclohexane (80-20 by volume)], collecting 20 cm³ fractions. Fractions 14 to 26 are combined and concentrated to dryness under reduced pressure (2.7 kPa) at 40° C. After recrystallization from acetonitrile, 1.0 g of N-(4-methoxyphenyl)-N-methyl-2-{2-[3-(3-methylphenyl)ureido]-N-phenylacetamido}acetamide melting at 202° C. is obtained.

2-(2-Amino-N-phenylacetamido)-N-(4-methoxyphenyl)-N-methylacetamide may be prepared in a manner analogous to that described in Example 1 for the preparation of 2-(2-amino-N-phenylacetamido)-N-phenylacetamide, but using 3.8 g of N-(4-methoxyphenyl)-N-methyl-2-(N-phenyl-2-phthalimidoacetamido)acetamide and 0.83 g of hydrazine hydrate as the starting material. 1.9 g of 2-(2-amino-N-phenylacetamido)-N-(4-methoxyphenyl)-N-methylacetamide are thus obtained in the form of an oil which is used as such in the subsequent syntheses.

N-(4-Methoxyphenyl)-N-methyl-2-(N-phenyl-2-phthalimidoacetamido)acetamide may be prepared in a manner analogous to that described in Example 1 for the preparation of 2-(N-phenyl-2-phthalimidoacetamido)-N-phenylacetamide, but using 5.0 g of 2-(N-phenyl-2-phthalimidoacetamido)acetic acid, 1.86 g of oxalyl dichloride and 2.4 g of 4-methoxy-N-methylaniline as the starting material. 3.8 g of N-(4-methoxyphenyl)-N-methyl-2-(N-phenyl-2-phthalimidoacetamido)acetamide melting at 162° C. are thus obtained.

EXAMPLE 6

The procedure is analogous to that described in Example 1, but 3.3 g of 2-amino-N-[2-oxo-2-(3,3-dimethylpiperidino)ethyl]-N-phenylacetamide and 1.6 g of 3-methylphenyl isocyanate are used as the starting material. After recrystallization from acetonitrile, 3.2 g of N-[2-oxo-2-(3,3-dimethylpiperidino)ethyl]-2-[3-(3-methylphenyl)ureido]-N-phenylacetamide melting at 170° C. are obtained.

2-Amino-N-[2-oxo-2-(3,3-dimethylpiperidino)ethyl]-N-phenylacetamide may be prepared in a manner analogous to that described in Example 1 for the preparation of 2-(2-amino-N-phenylacetamido)-N-phenylacetamide, but using 5.0 g of N-[2-oxo-2-(3,3-dimethylpiperidino)ethyl]-N-phenyl-2-phthalimidoacetamide and 1.2 g of hydrazine hydrate as the starting material. 3.3 g of 2-amino-N-[2-oxo-2-(3,3-dimethylpiperidino)ethyl]-N-phenylacetamide are thus obtained in the form of an oil which is used as such in the subsequent syntheses.

N-[2-Oxo-2-(3,3-dimethylpiperidino)ethyl]-N-phenyl-2-phthalimidoacetamide may be prepared in a manner analogous to that described in Example 1 for the preparation of 2-(N-phenyl-2-phthalimidoacetamido)-N-phenylacetamide, but using 6.8 g of 2-(N-phenyl-2-phthalimidoacetamido)-acetic acid, 2.8 g of oxalyl dichloride and 5.4 g of 3,3-dimethylpiperidine as the starting material. After recrystallization from an ethyl acetate/diisopropyl ether mixture (50-50 by volume), 5.0 g of N-[2-oxo-2-(3,3-dimethylpiperidino)ethyl]-N-phenyl-2-phthalimidoacetamide melting at 156° C. are thus obtained.

EXAMPLE 7

The procedure is analogous to that described in Example 1, but 2.8 g of 2-amino-N-[2-(4-methylpiperidino)-2-oxoethyl]-N-phenylacetamide and 1.3 g of 3-methylphenyl isocyanate are used as the starting material. The product obtained is purified by chromatography on 80 g of silica (0.065–0.200 mm) contained in a column 2.5 cm in diameter [eluent: methylene chloride/methanol (95-5 by volume)], collecting 20 cm³ fractions. Fractions 20 to 36 are combined and concentrated to dryness under reduced pressure (2.7 kPa) at 40° C. After recrystallization from acetonitrile, 1.4 g of N-[2-(4-methylpiperidino)-2-oxoethyl]-2-[3-(3-methylphenyl)ureido]-N-phenylacetamide melting at 180° C. are obtained.

2-Amino-N-[2-(4-methylpiperidino)-2-oxoethyl]-N-phenylacetamide may be prepared in a manner analogous to that described in Example 1 for the preparation of 2-(2-amino-N-phenylacetamido)-N-phenylacetamide but using 5.7 g of N-[2-(4-methylpiperidino)-2-oxoethyl]-N-phenyl-2-phthalimidoacetamide and 1.45 g of hydrazine hydrate as the starting material. 2.8 g of 2-amino-N-[2-(4-methylpiperidino)-2-oxoethyl]-N-phenylacetamide are thus obtained in the form of an oil which is used as such in the subsequent syntheses.

N-[2-(4-Methylpiperidino)-2-oxoethyl]-N-phenyl-2-phthalimidoacetamide may be prepared in a manner analogous to that described in Example 1 for the preparation of 2-(N-phenyl-2-phthalimidoacetamido)-N-phenylacetamide, but using 10.1 g of 2-(N-phenyl-2-phthalimidoacetamido)acetic acid, 3.9 g of oxalyl dichloride and 7.1 g of 4-methylpiperidine as the starting material. After recrystallization from diisopropyl ether, 6.0 g of N-[2-(4-methylpiperidino)-2-oxoethyl]-N-phenyl-2-phthalimidoacetamide melting at 138° C. are obtained.

EXAMPLE 8

The procedure is analogous to that described in Example 1, but 1.45 g of (RS)-2-amino-N-[2-(2-methylpiperidino)-2-oxoethyl]-N-phenylacetamide and 0.67 g of 3-methylphenyl isocyanate used as the starting material. After recrystallization from a mixture of ethanol and diisopropyl ether (50-50 by volume), 0.80 g of (RS)-N-[2-(2-methylpiperidino)-2-oxoethyl]-2-[3-(3-methylphenyl)ureido]-N-phenylacetamide melting at 188° C. is obtained.

(RS)-2-Amino-N-[2-(2-methylpiperidino)-2-oxoethyl]-N-phenylacetamide may be prepared in a manner analogous to that described in Example 1 for the preparation of 2-(2-amino-N-phenylacetamido)-N-phenylacetamide, but using 4.5 g of (RS)-N-[2-(2-methylpiperidino)-2-oxoethyl]-N-phenyl-2-phthalimidoacetamide and 1.1 g of hydrazine hydrate as the starting material. 2.9 g of (RS)-2-amino-N-[2-(2-methylpiperidino)-2-oxoethyl]-N-phenylacetamide are thus obtained in the form of an oil which is used as such in the subsequent syntheses.

(RS)-N-[2-(2-Methylpiperidino)-2-oxoethyl]-N-phenyl-2-phthalimidoacetamide may be prepared in a manner analogous to that described in Example 1 for the preparation of 2-(N-phenyl-2-phthalimidoacetamido)-N-phenylacetamide, but using 5.1 g of 2-(N-phenyl-2-phthalimidoacetamido)acetic acid, 2.1 g of oxalyl dichloride and 3.6 g of (RS)-2-methylpiperidine as the starting material. After recrystallization from diisopropyl ether, 4.4 g of (RS)-N-[2-(2-methylpiperidino)-2-oxoethyl]-N-phenyl-2-phthalimidoacetamide melting at 110° C. are obtained.

EXAMPLE 9

The procedure is analogous to that described in Example 1, but 1.0 g of (RS)-2-amino-N-[2-(3-methylpiperidino)-2-oxoethyl]-N-phenylacetamide and 0.47 g of 3-methylphenyl isocyanate are used as the starting material. After recrystallization from a mixture of ethanol and diisopropyl ether (50-50 by volume), 0.66 g of (RS)-N-[2-(3-methylpiperidino)-2-oxoethyl]-2-N-[3-(3-methylphenyl)ureido]-N-phenylacetamide melting at 180° C. is obtained.

(RS)-2-amino-N-[2-(3-methylpiperidino)-2-oxoethyl]-N-phenylacetamide may be prepared in a manner analogous to that described in Example 1 for the preparation of 2-(2-amino-N-phenylacetamido)-N-phenylacetamide, but using 3.3 g of (RS)-N-[2-(3-methylpiperidino)-2-oxoethyl]-N-phenyl-2-phthalimidoacetamide and 0.8 g of hydrazine hydrate as the starting material. 2 g of (RS)-2-amino-N-[2-(3-methylpiperidino)-2-oxoethyl]-N-phenylacetamide are thus obtained in the form of an oil which is used as such in the subsequent syntheses.

(RS)-N-[2-(3-Methylpiperidino)-2-oxoethyl]-N-phenyl-2-phthalimidoacetamide may be prepared in a manner analogous to that described in Example 1 for the preparation of 2-(N-phenyl-2-phthalimidoacetamido)-N-phenylacetamide, but using 5.1 g of 2-(N-phenyl-2-phthalimidoacetamido)acetic acid, 2.1 g of oxalyl dichloride and 3.6 g of (RS)-3-methylpiperidine as the starting material. After recrystallization from diisopropyl ether, 3.3 g of (RS)-N-[2-(3-methylpiperidino)-2-oxoethyl]-N-phenyl-2-phthalimidoacetamide melting at 134° C. are obtained.

EXAMPLE 10

The procedure is analogous to that described in Example 1, but 1.2 g of 2-amino-N-[2-oxo-2-(1perhydroazepinyl)ethyl]-N-phenylacetamide and 0.55 g of 3-methylphenyl isocyanate are used as the starting material. After recrystallization from a mixture of dimethylformamide and ethyl acetate (63-35 by volume), 0.9 g of N-[2-oxo-2-(1-perhydroazepinyl)ethyl]-2-[3-(3-methylphenyl)ureido]-N-phenylacetamide melting at 245° C. is obtained.

2-Amino-N-[2-oxo-2-(1-perhydroazepinyl)-ethyl]-N-phenylacetamide may be prepared in a manner analogous to that described in Example 1 for the preparation of 2-(2-amino-N-phenylacetamido)-N-phenylacetamide, but using 2.1 g of N-[2-oxo-2-(1-perhydroazepinyl)ethyl]-N-phenyl-2-phthalimidoacetamide and 0.5 g of hydrazine hydrate as the starting material. 1.2 g of 2-amino-N-[2-oxo-2-(1-perhydroazepinyl)ethyl]-N-phenylacetamide are thus obtained in the form of an oil which is used as such in the subsequent syntheses.

N-[2-Oxo-2-(1-perhydroazepinyl)ethyl]-N-phenyl-2-phthalimidoacetamide may be prepared in a manner analogous to that described in Example 1 for the preparation of 2-(N-phenyl-2-phthalimidoacetamido)-N-phenylacetamide, but using 10.1 g of 2-(N-phenyl-2-phthalimidoacetamido)acetic acid, 4.2 g of oxalyl dichloride and 6 g of perhydroazepine as the starting material. After recrystallization from ethyl acetate, 3.8 g N-[2-oxo-2-(1-perhydroazepinyl)ethyl]-N-phenyl-2-phthalimidoacetamide melting at 140° C. are thus obtained.

EXAMPLE 11

The procedure is analogous to that described in Example 1, but 1.8 g of 2-amino-N-[2-(1-indolinyl)-2-oxoethyl]-N-phenylacetamide and 0.8 g of 3-methylphenyl isocyanate are used as the starting material. After recrystallization from a mixture of ethyl acetate and dimethylformamide (80-20 by volume), 0.7 g of N-[2-(1-indolinyl)-2-oxoethyl]-2-[3-(3-methylphenyl)ureido]-N-phenylacetamide melting at 190° C. is obtained.

2-Amino-N-[2-(1-indolinyl)-2-oxoethyl]-N-phenylacetamide may be prepared in a manner analogous to that described in Example 1 for the preparation of 2-(2-amino-N-phenylacetamido)-N-phenylacetamide, but using 3.7 g of N-[2-(1-indolinyl)-2-oxoethyl]-N-phenyl2-phthalimidoacetamide and 1.7 g of hydrazine hydrate as the starting material. 1.8 g of 2-amino-N-[2-(1-indolinyl)-2-oxoethyl]-N-phenylacetamide are thus obtained in the form of an oil which is used as such in the subsequent syntheses.

N-[2-(1-Indolinyl)-2-oxoethyl]-N-phenyl-2-phthalimidoacetamide may be prepared in a manner analogous to that described in Example 1 for the preparation of 2-(N-phenyl-2-phthalimidoacetamido)-N-phenylacetamide, but using 4 g of 2-(N-phenyl-2-phthalimidoacetamide)acetic acid, 1.7 g of oxalyl dichloride and 2.8 g of indoline as the starting material. 3.7 g of N-[2-(1-indolinyl)-2-oxoethyl]-N-phenyl-2-phthalimidoacetamide melting at 230° C. are thus obtained.

EXAMPLE 12

The procedure is analogous to that described in Example 1, but 2.0 g of 2-amino-N-[2-oxo-2-(1,2,3,6-tetrahydro-1-pyridyl)ethyl]-N-phenylacetamide and 0.97 g of 3-methylphenyl isocyanate are used as the starting material. After recrystallization from acetonitrile, 1.4 g of N-[2-oxo-2-(1,2,3,6-tetrahydro-1-pyridyl)ethyl]-2-[3-(3-methytphenyl)ureido]-N-phenylacetamide melting at 171° C. are obtained.

2-Amino-N-[2-oxo-2-(1,2,3,6-tetrahydro-1-pyridyl)ethyl]-N-phenylacetamide may be prepared in a manner analogous to that described in Example 1 for the preparation of 2-(2-amino-N-phenylacetamido)-N-phenylacetamide, but using 3.6 g of N-[2-oxo-2-(1,2,3,6-tetrahydro-1-pyridyl)ethyl]-N-phenyl-2-phthalimidoacetamide and 0.92 g of hydrazine hydrate as the starting material. 2.1 g of 2-amino-N-[2-oxo-2-(1,2,3,6-tetrahydro-1-pyridyl)ethyl]-N-phenylacetamide are thus obtained in the form of an oil which is used as such in the subsequent syntheses.

N-[2-oxo-2-(1,2,3,6-tetrahydro-1-pyridyl)ethyl]-N-phenyl-2-phthalimidoacetamide may be prepared in a manner analogous to that described in Example 1 for the preparation of 2-(N-phenyl-2-phthalimidoacetamide)-N-phenylacetamide, but using 5.1 g of 2-(N-phenyl-2-phthalimidoacetamido)acetic acid, 2.1 g of oxalyl dichloride and 3.7 g of 1,2,3,6-tetrahydropyridine as the starting material. After recrystallization from ethanol, 3.7 g of N-[2-oxo-2-(1,2,3,6-tetrahydro-1-pyridyl)ethyl]-N-phenyl-2-phthalimidoacetamide melting at 180° C. are thus obtained.

EXAMPLE 13

The procedure is analogous to that described in Example 1, but 0.9 g of 2-(2-amino-N-phenylacetamido)-N-cyclopropylmethylacetamide and 0.45 g of 3-methylphenyl isocyanate are used as the starting material. After recrystallization from acetonitrile, 1 g of N-cyclopropylmethyl-2-{2-[3-(3-methylphenyl)ureido]-N-phenylacetamido}acetamide melting at 168° C. is obtained.

2-(2-Amino-N-phenylacetamido)-N-cyclopropylmethylacetamide may be prepared in a manner analogous to that described in Example 1 for the preparation of 2-(2-amino-N-phenylacetamido)-N-phenylacetamide, but using 1.8 g of N-cyclopropylmethyl-2-(N-phenyl-2-phthalimidoacetamido)acetamide and 0.46 g of hydrazine hydrate as the starting material. 0.9 g of 2-(2-amino-N-phenylacetamido)-N-cyclopropylmethylacetamide is thus obtained in the form of an oil which is used as such in the subsequent syntheses.

N-Cyclopropylmethyl-2-(N-phenyl-2-phthalimidoacetamido)acetamide may be prepared in the following way: 0.8 g of N,N'-diimidazolecarbonyl is added to a suspension of 1.7 g of 2-(N-phenyl-2-phthalimidoacetamido)acetic acid in 20 cm³ of anhydrous tetrahydrofuran. The mixture is stirred for 1 hour at a temperature close to 25° C. and a mixture of 0.65 g of cyclopropylamine hydrochloride and 0.62 g of triethylamine in 15 cm³ of anhydrous tetrahydrofuran is then added in a single amount. The reaction mixture is stirred under reflux for 8 hours and then concentrated to dryness under reduced pressure (2.7 kPa) at 40° C. The residue is dissolved in 25 cm³ of ethyl acetate and the solution obtained is washed with twice 15 cm³ of distilled water, dried over magnesium sulphate and then concentrated to dryness under reduced pressure (2.7 kPa) at 40° C. After recrystallization from diethyl ether, 1.5 g of N-cyclopropylmethyl-2-(N-phenyl-2-phthalimidoacetamido)acetamide melting at 144° C. are obtained.

EXAMPLE 14

The procedure is analogous to that described in Example 1, but 1.0 g of 2-(2-amino-N-phenylacetamido)-N-tert-butylacetamide and 0.55 g of 3-methylphenyl isocyanate are used as the starting material. After recrystallization from acetonitrile, 1.0 g of N-tert-butyl-2-{2-[3-(3-methylphenyl)ureido]-N-phenylacetamido}acetamide melting at 214° C. is obtained.

2-(2-Amino-N-phenylacetamido)-N-tert-butylacetamide may be prepared in a manner analogous to that described in Example 1 for the preparation of 2-(2-amino-N-phenylacetamido)-N-phenylacetamide, but using 1.6 g of N-tert-butyl-2-(N-phenyl-2-phthalimidoacetamido)acetamide and 0.23 g of hydrazine hydrate as the starting material. 1.1 g of 2-(2-amino-N-phenylacetamido)-N-tert-butylacetamide are thus obtained in the form of a meringue which is used as such in the subsequent syntheses.

N-tert-Butyl-2-(N-phenyl-2-phthalimidoacetamido)acetamide may be prepared in a manner analogous to that described in Example 1 for the preparation of 2-(N-phenyl-2-phthalimidoacetamido)-N-phenylacetamide, but using 1.7 g of 2-(N-phenyl-2-phthalimidoacetamido)acetic acid, 0.64 g of oxalyl dichloride and 0.8 g of tert-butylamine as the starting material. 1.65 g of N-tert-butyl-2-(N-phenyl-2-phthalimidoacetamido)acetamide melting at 166° C. are thus obtained.

EXAMPLE 15

The procedure is analogous to that described in Example 1, but 0.25 g of 2-(2-amino-N-phenylacetamido)-N-benzylacetamide and 0.11 g of 3-methylphenyl isocyanate are used as the starting material. After recrystallization from acetonitrile, 0.17 g of N-benzyl-2-{2-[3-(3-methylphenyl)ureido]-N-phenylacetamido]acetamide melting at 204° C. is obtained.

2-(2-Amino-N-phenylacetamido)-N-benzylacetamide may be prepared in a manner analogous to that described in Example 1 for the preparation of 2-(2-amino-N-phenylacetamido)-N-phenylacetamide, but using 1.0 g of N-benzyl-2-(N-phenyl-2-phthalimidoacetamido)acetamide and 0.23 g of hydrazine hydrate as the starting material. 0.25 g of 2-(2-amino-N-phenylacetamido)-N-benzylacetamide is thus obtained in the form of an oil which is used as such in the subsequent syntheses.

N-Benzyl-2-(N-phenyl-2-phthalimidoacetamido)acetamide may be prepared in a manner analogous to that described in Example 1 for the preparation of 2-(N-phenyl-2- phthalimidoacetamido)-N-phenylacetamide, but using 1.0 g of 2-(N-phenyl-2-phthalimidoacetamido)acetic acid, 0.38 g of oxalyl dichloride and 0.59 g of benzylamine as the starting material. 1.0 g of N-benzyl-2-(N-phenyl-2-phthalimidoacetamido)acetamide is thus obtained in the form of an oil which is used as such in the subsequent syntheses.

EXAMPLE 16

The procedure is analogous to that described in Example 1, but 3.0 g of 2-(2-amino-N-phenylacetamido)-N-(4-chlorophenyl)acetamide and 1.2 g of 3-methylphenyl isocyanate are used as the starting material. After recrystallization from tetrahydrofuran, 2.3 g of N-(4-chlorophenyl)-2-{2-[3-(3-methylphenyl)ureido]-N-phenylacetamido}acetamide melting at 220° C. are obtained.

2-(2-Amino-N-phenylacetamido)-N-(4-chlorophenyl)acetamide may be prepared in a manner analogous to that described in Example 1 for the preparation of 2-(2-amino-N-phenylacetamido)-N-phenylacetamide, but using 3.0 g of N-(4-chlorophenyl)2-(N-phenyl-2-phthalimidoacetamido)acetamide and 0.9 g of hydrazine hydrate as the starting material. 3.0 g of 2-(2-amino-N-phenylacetamido)-N-(4-chlorophenyl)acetamide are thus obtained in the form of an oil which is used as such in the subsequent syntheses.

N-(4-Chlorophenyl)-2-(N-phenyl-2-phthalimidoacetamido)acetamide may be prepared in a manner analogous to that described in Example 1 for the preparation of 2-(N-phenyl-2-phthalimidoacetamido)-N-phenylacetamide, but using 4.0 g of 2-(N-phenyl-2-phthalimidoacetamido)acetic acid, 1.7 g of oxalyl dichloride and 3.0 g of 4-chloroaniline as the starting material. After recrystallization from an ethyl acetate/diisopropyl ether mixture (50-50 by volume), 4.0 g of N-(4-chlorophenyl)-2-(N-phenyl-2-phthalimidoacetamido)acetamide melting at 200° C. are obtained.

EXAMPLE 17

The procedure is analogous to that described in Example 1, but 1.9 g of 2-(2-amino-N-phenylacetamido)-N-(4-methylphenyl)acetamide and 0.85 g of 3-methylphenyl isocyanate are used as the starting material. After recrystallization from acetonitrile, 1.3 g of N-(4-methylphenyl)-2-{2-[3-(3-methylphenyl)ureido]-N-phenylacetamido}acetamide melting at 170° C. are obtained.

2-(2-Amino-N-phenylacetamido)-N-(4-methylphenyl)acetamide may be prepared in a manner analogous to that described in Example 1 for the preparation of 2-(2-amino-N-phenylacetamido)-N-phenylacetamide, but using 3.1 g of N-(4-methylphenyl)-2-(N-phenyl-2-phthalimidoacetamido)acetamide and 0.73 g of hydrazine hydrate as the starting material. 1.9 g of 2-(2-amino-N-phenylacetamido)-N-(4-methylphenyl)acetamide are thus obtained in the form of an oil which is used as such in the subsequent syntheses.

N-(4-Methylphenyl)-2-(N-phenyl-2-phthalimidoacetamido)acetamide may be prepared in a manner analogous to that described in Example 1 for the preparation of 2-(N-phenyl-2-phthalimidoacetamido)-N-phenylacetamide, but using 4.0 g of 2-(N-phenyl-2-phthalimidoacetamido)acetic acid, 1.7 g of oxalyl dichloride and 2.5 g of 4-methylaniline as the starting material. After recrystallization from an ethyl acetate/diisopropyl ether mixture (50-50 by volume), 3.1 g of N-(4-methylphenyl)-2-(N-phenyl-2-phthalimidoacetamido)acetamide melting at 185° C. are obtained.

EXAMPLE 18

The procedure is analogous to that described in Example 1, but 3.0 g of 2-(2-amino-N-phenylacetamido)-N-(5-indanyl)acetamide and 1.2 g of 3-methylphenyl isocyanate are used as the starting material. After recrystallization from acetonitrile, 0.8 g of N-(5-indanyl)-2-{2-[3-(3-methylphenyl)ureido]-N-phenylacetamido}acetamide melting at 210° C. is obtained.

2-(2-Amino-N-phenylacetamido)-N-(5-indanyl)acetamide may be prepared in a manner analogous to that described in Example 1 for the preparation of 2-(2-amino-N-phenylacetamido)-N-phenylacetamide, but using 4.0 g of N-(5-indanyl)-2-(N-phenyl-2-phthalimidoacetamido)acetamide and 0.9 g of hydrazine hydrate as the starting material. 3.0 g of 2-(2-amino-N-phenylacetamido)-N-(5-indanyl)acetamide are thus obtained in the form of an oil which is used as such in the subsequent syntheses.

N-(5-Indanyl)-2-(N-phenyl-2-phthalimidoacetamido)acetamide may be prepared in a manner analogous to that described in Example 1 for the preparation of 2-(N-phenyl-2-phthalimidoacetamido)-N-phenylacetamide, but using 4.0 g of 2-(N-phenyl-2-phthalimidoacetamido)acetic acid, 1.7 g of oxalyl dichloride and 3.1 g of 5-aminoindane, as the starting material. After recrystallization from an ethyl acetate/diisopropyl ether mixture (50-50 by volume), 4.0 g of N-(5-indanyl)-2-(N-phenyl-2-phthalimidoacetamido)acetamide melting at 216° C. are obtained.

EXAMPLE 19

The procedure is analogous to that described in Example 1, but 1.8 g of 2-(2-amino-N-phenylacetamido)-N-(2-methylphenyl)acetamide and 0.82 g of 3-methylphenyl isocyanate are used as the starting material. After recrystallization from acetonitrile, 1.2 g of N-(2-methylphenyl)-2-{2-[3-(3methylphenyl)ureido]-N-phenylacetamido}acetamide melting at 200° C. are obtained.

2-(2-Amino-N-phenylacetamido)-N-(2-methylphenyl)acetamide may be prepared in a manner analogous to that described in Example 1 for the preparation of 2-(2-amino-N-phenylacetamido)-N-phenylacetamide, but using 6.8 g of N-(2-methylphenyl)-2-(N-phenyl-2-phthalimidoacetamido)acetamide and 1.55 g of hydrazine hydrate as the starting material. 1.8 g of 2-(2-amino-N-phenylacetamido)-N-(2-methylphenyl)acetamide are thus obtained in the form of an oil which is used as such in the subsequent syntheses.

N-(2-Methylphenyl)-2-(N-phenyl-2-phthalimidoacetamido)acetamide may be prepared in a manner analogous to that described in Example 1 for the preparation of 2-(N-phenyl-2-phthalimidoacetamido)-N-phenylacetamide, but using 6.8 g of 2-(N-phenyl-2-phthalimidoacetamido)acetic acid, 1.7 g of oxalyl dichloride and 5.1 g of 2-methylaniline as the starting material. 6.8 g of N-(2-methylphenyl)-2-(N-phenyl-2-phthalimidoacetamido)acetamide melting at 160° C. are thus obtained.

EXAMPLE 20

The procedure is analogous to that described in Example 1, but 1.4 g of tert-butyl N-{2-[(2-aminoacetyl)-phenylamino]acetyl}-N-phenylglycinate and 0.45 g of 3-methylphenyl isocyanate are used as the starting material. The product obtained is purified by chromatography on 80 g of silica (0.04–0.063 mm) contained in a column 3 cm in diameter [eluent: methylene chloride/methanol (98-2 by volume)] using an excess pressure of 30 kPa of nitrogen and collecting 35 cm³ fractions. Fractions 19 to 21 are combined and concentrated to dryness under reduced pressure (2.7 kPa) at 40° C. After churning the residue obtained with 25 cm³ of heptane, 0.4 g of tert-butyl N-{2-{2-[3-(3-methylphenyl)ureido]-N-phenylacetamido}acetyl}-N-phenylglycinate melting at 76°–80° C. is obtained.

tert-Butyl N-{2-[(2-aminoacetyl)-phenylamino]acetyl}-N-phenylglycinate may be prepared in a manner analogous to that described in Example 1 for the preparation of 2-(2-amino-N-phenylacetamido)-N-phenylacetamide, but using 2.3 g of tert-butyl N-{2-[(2-phthalimidoacetyl)-phenylamino]acetyl}-N-phenylglycinate and 0.4 g of hydrazine hydrate as the starting material. 1.4 g of tert-butyl N-{2-[(2-aminoacetyl)phenylamino]acetyl}-N-phenylglycinate are thus obtained in the form of a thick oil which is used as such in the subsequent syntheses.

tert-Butyl N-{2-[(2-phthalimidoacetyl)-phenylamino]acetyl}-N-phenylglycinate may be prepared in a manner analogous to that described in Example 1 for the preparation of 2-(N-phenyl-2-phthalimidoacetamido)-N-phenylacetamide, but using 5.1 g of 2-(N-phenyl-2-phthalimidoacetamido)acetic acid, 2.1 g of oxalyl dichloride and 3.1 g of tert-butyl N-phenylglycinate as the starting material. 2.3 g of tert-butyl N-{2-[(2-phthalimidoacetyl)-phenylamino]acetyl}-N-phenylglycinate melting at 80° C. are thus obtained.

EXAMPLE 21

The procedure is analogous to that described in Example 1, but 1.5 g of (RS)-2-amino-N-[1-(3,3-dimethylpiperidino)-1-oxo-2-propyl]-N-phenylacetamide and 0.63 g of 3-methylphenyl isocyanate are used as the starting material. The product obtained is purified by chromatography on 40 g of silica (0.065–0.200 mm) contained in a column 2.2 cm in diameter [eluent: methylene chloride/ethyl acetate (50-50 by volume)], collecting 25 cm³ fractions. Fractions 14 to 24 are combined and concentrated to dryness under reduced pressure (2.7 kPa) at 40° C. After recrystallization from diethyl ether, 1.6 g of (RS)-N-[1-(3,3-dimethylpiperidino)-1-oxo-2-propyl]-2-[3-(3-methylphenyl)ureido]-N-phenylacetamide melting at 149° are obtained.

(RS)-2-Amino-N-[1-(3,3-dimethylpiperidino)-1-oxo-2-propyl]-N-phenylacetamide may be prepared in a manner analogous to that described in Example 1 for the preparation of 2-(2-amino-N-phenylacetamido)-N-phenylacetamide, but using 10.8 g of (RS)-N-[1-(3,3-dimethylpiperidino)-1-oxo-2-propyl]-N-phenyl-2-phthalimidoacetamide and 2.4 g of hydrazine hydrate as the starting material. 6.6 g of (RS)-2-amino-N-[1-(3,3-dimethylpiperidino)-1-oxo-2-propyl]-N-phenylacetamide are thus obtained in the form of an oil which is used as such in the subsequent syntheses.

N-[1-(3,3-dimethylpiperidino)-1-oxo-2-propyl]-N-phenyl-2-phthalimidoacetamide may be prepared in a manner analogous to that described in Example 1 for the preparation of tert-butyl 2-(N-phenyl-2-phthalimidoacetamido)-acetate, but using 6.4 g of (RS)-3,3-dimethyl-1-(2-phenylaminopropionyl)piperidine and 5.5 g of 2-phthalimidoacetyl chloride as the starting material. 10.9 g of (RS)-N-[1-(3,3-dimethylpiperidino)-1-oxo-2-propyl]-N-phenyl-2-phthalimidoacetamide melting at 171° C. are thus obtained.

(RS)-3,3-Dimethyl-1-(2-phenylaminopropionyl)-piperidine may be prepared in the following way: a solution of 5.7 g of 3,3-dimethylpiperidine and 6.0 g of triethylamine in 15 cm³ of acetonitrile is added in the course of 1 hour to a solution of 8.5 g of 2-bromopropionyl chloride in 90 cm³ of acetonitrile. The reaction mixture is stirred at a temperature close to 25° C. for 18 hours and 7 g of aniline and 6 g of triethylamine are then added. The acetonitrile is distilled and the reaction mixture is stirred at a temperature close to 100° C. for 5 hours. After cooling, 200 cm³ of ethyl acetate and 200 cm³ of distilled water are added. The organic phase is extracted with twice 100 cm³ of a 1N aqueous hydrochloric acid solution. The aqueous phase obtained is rendered alkaline to pH 10 with a 4N aqueous sodium hydroxide solution and extracted with twice 100 cm³ of diethyl ether. The organic phases are combined, washed with 100 cm³ of distilled water, dried over magnesium sulphate and concentrated to dryness under reduced pressure (2.7 kPa) at 30° C.). After recrystallization from diisopropyl ether, 6.5 g of (RS)-3,3-dimethyl-1-(2-phenylamino-propionyl)piperidine melting at 98° C. are obtained.

EXAMPLE 22

The procedure is analogous to that described in Example 1, but 1.0 g of (RS)-2-(2-amino-N-phenylacetamido)-N-methyl-N-phenylpropionamide and 0.42 g of 3-methylphenyl isocyanate are used as the starting material. After recrystallization from a mixture of acetonitrile and dimethylformamide (93-7 by volume), 0.5 g of (RS)-N-methyl-2-{2-[3-(3-methylphenyl)ureido]-N-phenylacetamido}-N-phenylpropionamide melting at 214° C. is obtained.

(RS)-2-(2-Amino-N-phenylacetamido)-N-methyl-N-phenylpropionamide may be prepared in a manner analogous to that described in Example 1 for the preparation of 2-(2-amino-N-phenylacetamido)-N-phenylacetamide, but using 15.4 g of (RS)-N-methyl-N-phenyl-2-(N-phenyl-2-phthalimidoacetamido)propionamide and 3.4 g of hydrazine hydrate as the starting material. 9.6 g of (RS)-2-(2-amino-N-phenylacetamido)-N-methyl-N-phenylpropionamide are thus obtained in the form of an oil which is used as such in the subsequent syntheses.

(RS)-N-Methyl-N-phenyl-2-(N-phenyl-2-phthalimidoacetamido)propionamide may be prepared in a manner analogous to that described in Example 1 for the preparation of tert-butyl 2-(N-phenyl-2-phthalimidoacetamido)acetate, but using 9.5 g of (RS)-2-anilino-N-methyl-N-phenylpropionamide and 8.3 g of 2-phthalimidoacetyl chloride as the starting material. After recrystallization from diethyl ether, 15.5 g of (RS)-N-methyl-N-phenyl-2-(N-phenyl-2-phthalimidoacetamido)propionamide melting at 120° C. are thus obtained.

(RS)-2-Anilino-N-methyl-N-phenylpropionamide may be prepared in a manner analogous to that described in Example 21 for the preparation of (RS)-3,3- dimethyl-1-(2-phenylaminopropionyl)piperidine, but using 20 g of 2-bromopropionyl chloride, 20 g of triethylamine, 12.5 g of N-methylaniline and 32.6 g of aniline as the starting material. The product obtained is purified by chromatography on 700 g of silica gel (0.065–0.200 mm) contained in a column 6 cm in diameter [eluent: ethyl acetate/cyclohexane (30-70 by volume)], collecting 200 cm³ fractions. Fractions 9 to 13 are combined and concentrated to dryness under reduced pressure (2.7 kPa) at 40° C. After recrystallization from cyclohexane, 9.6 g of (RS)-2-anilino-N-methyl-N-phenylpropionamide melting at 90° C. are obtained.

EXAMPLE 23

0.37 g of hydrazine hydrate is added to a suspension of 1.6 g of N-(3-methylphenyl)-2-(N-phenyl-2-phthalimidoacetamido)acetamide in 10 cm³ of methanol. The reaction mixture is stirred under reflux for 40 minutes and then concentrated to dryness under reduced pressure (2.7 kPa) at 40° C. The residue is stirred for 30 minutes in 15 cm³ of anhydrous tetrahydrofuran and the insoluble product is separated off by filtration. 0.5 g of 3-methylphenyl isocyanate is then added to the filtrate and the mixture is stirred for 30 minutes at a temperature close to 25° C. and then concentrated to dryness under reduced pressure (2.7 kPa) at 40° C. The residue obtained is purified by chromatography on 150 g of silica (0.065–0.200 mm) contained in a column 3.5 cm in diameter [eluent: methylene chloride/ethyl acetate (80-20 by volume)], collecting 25 cm³ fractions. Fractions 21 to 27 are combined and concentrated to dryness under reduced pressure (2.7 kPa) at 40° C. After recrystallization from acetonitrile, 0.27 g of N-(3-methylphenyl)-2-{2-[3-(3-methylphenyl)ureido]-N-phenylacetamido}acetamide melting at 187° C. is thus obtained.

N-(3-Methylphenyl)-2-(N-phenyl-2-phthalimidoacetamido)acetamide may be prepared in the following way: 0.75 g of 3-methylaniline is added to a suspension of 2.6 g of N-[2-(1-imidazolyl)-2-oxoethyl]-N-phenyl-2-phthalimidoacetamide in 25 cm³ of toluene. The reaction mixture is stirred under reflux for 6 hours and then concentrated to dryness under reduced pressure (2.7 kPa) at 40° C. The residue is dissolved in 30 cm³ of methylene chloride and the solution obtained is washed successively with 20 cm³ of a 1N aqueous hydrochloric acid solution and with twice 15 cm³ of distilled water, then dried over magnesium sulphate and concentrated to dryness under reduced pressure (2.7 kPa) at 40° C. 1.6 g of N-(3-methylphenyl)-2-(N-phenyl-2-phthalimidoacetamido)acetamide are thus obtained in the form of a meringue which is used as such in the subsequent syntheses.

N-[2-(1-Imidazolyl)-2-oxoethyl]-N-phenyl-2-phthalimidoacetamide may be prepared in the following way: 2.4 g of N,N'-diimidazolecarbonyl are added to a suspension of 5 g of 2-(N-phenyl-2-phthalimidoacetamido)acetic acid in 30 cm³ of anhydrous tetrahydrofuran. The reaction mixture is stirred for 1 hour at a temperature close to 25° C. and the insoluble product obtained is then separated off by filtration and washed with twice 5 cm³ of tetrahydrofuran and air-dried. 5.3 g of N-[2-(1-imidazolyl)-2-oxoethyl]-N-phenyl-2-phthalimidoacetamide melting at 206° C. are thus obtained.

EXAMPLE 24

The procedure is analogous to that described in Example 23, but 3.1 g of N-[2-oxo-2-(1,2,3,4-tetrahydro-1-quinolyl)ethyl]-N-phenyl-2-phthalimidoacetamide, 0.69 g of hydrazine hydrate and 0.91 g of 3-methylphenyl isocyanate are used as the starting material. The product obtained is purified by chromatography on 25 g of silica (0.065–0.200 mm) contained in a column 1.7 cm in diameter [eluent: methylene chloride/ethyl acetate (80-20 by volume)], collecting 25 cm³ fractions. Fractions 12 to 23 are combined and concentrated to dryness under reduced pressure (2.7 kPa) at 40° C. After recrystallization from ethyl acetate, 0.9 g of 2-[3-(3-methylphenyl)ureido]-N-[2-oxo-2-(1,2,3,4-tetrahydro-1-quinolyl)ethyl]-N-phenylacetamide melting at 167° C. is obtained.

N-[2-Oxo-2-(1,2,3,4-tetrahydro-1-quinolyl)ethyl]-N-phenyl-2-phthalimidoacetamide may be prepared in a manner analogous to that described in Example 1 for the preparation of 2-(N-phenyl-2-phthalimidoacetamido)-N-phenylacetamide but using 2.5 g of 2-(N-phenyl-2-phthalimidoacetamido)acetic acid, 0.95 g of oxalyl dichloride and 1.0 g of 1,2,3,4-tetrahydroquinoline as the starting material. 3.2 g of N-[2-oxo-2-(1,2,3,4-tetrahydro-1-quinolyl)ethyl]-N-phenyl-2-phthalimidoacetamide are thus obtained in the form of a meringue which is used as such in the subsequent syntheses.

EXAMPLE 25

The procedure is analogous to that described in Example 23, but 1.6 g of N-methyl-N-(4-methylphenyl)-2-(N-phenyl-2-phthalimidoacetamido)acetamide, 0.36 g of hydrazine hydrate and 0.3 g of 3-methylphenyl isocyanate are used as the starting material. The product obtained is purified by chromatography on 80 g of silica gel (0.065–0.200 mm) contained in a column 2.5 cm in diameter [eluent: methylene chloride], collecting 20 cm³ fractions. Fractions 10 to 12 are combined and concentrated to dryness under reduced pressure (2.7 kPa) at 40° C. After recrystallization from a mixture of ethyl acetate and diethyl ether (40-60 by volume), 0.7 g of N-methyl-N-(4-methylphenyl)-2-{2-[3-(3-methylphenyl)ureido]-N-phenylacetamido}acetamide melting at 162° C. is obtained.

N-Methyl-N-(4-methylphenyl)-2-(N-phenyl-2-phthalimidoacetamido)acetamide may be prepared in a manner analogous to that descried in Example 1 for the preparation of 2-(N-phenyl-2-phthalimidoacetamido)-N-phenylacetamide, but using 2.0 g of 2-(N-phenyl-2-phthalimidoacetamido)acetic acid, 0.82 g of oxalyl dichloride and 1.55 g of N-methyl-4-methylaniline as the starting material. After recrystallization from cyclohexane, 9.6 g of N-methyl-N-(4-methylphenyl)-2-(N-phenyl-2-phthalimidoacetamido)acetamide melting at 90° C. are obtained.

N-Methyl-4-methylaniline may be prepared by the method described by A. M. HJort, E. J. DeBeer, J. S. Buck and W. S. Ide, J. Pharmacol. Exp. Therap., 55, 152 (1935).

EXAMPLE 26

The procedure is analogous to that described in Example 23, but 2.7 g of N-methyl-N-(3-methylphenyl)-2-(N-phenyl-2-phthalimidoacetamido)acetamide, 0.6 g of hydrazine hydrate and 0.8 g of 3-methylphenyl isocyanate are used as the starting material. The product obtained is purified by chromatography on 25 g of silica gel (0.065–0.200 mm) contained in a column 1.7 cm in diameter [eluent: methylene chloride/ethyl acetate (80-20 by volume)], collecting 25 cm³ fractions. Fractions 13 to 27 are combined and concentrated to dryness under reduced pressure (2.7 kPa) at 40° C. After recrystallization from diethyl ether, 0.86 g of N-methyl-N-(3-methylphenyl)-2-{2-[3-(3-methylphenyl)ureido]-N-phenylacetamido}acetamide melting at 165° C. is obtained.

N-Methyl-N-(3-methylphenyl)-2-(N-phenyl-2-phthalimidoacetamido)acetamide may be prepared in a manner analogous to that described in Example 1 for the preparation of 2-(N-phenyl-2-phthalimidoacetamido)-N-phenylacetamide, but using 2.0 g of 2-(N-phenyl-2-phthalimidoacetamido)acetic acid, 0.76 g of oxalyl dichloride and 0.74 g of N-methyl-3-methylaniline and 0.6 g of triethylamine as the starting material. 2.7 g of N-methyl-N-(3-methylphenyl)-2-(N-phenyl-2-phthalimidoacetamido)acetamide are thus obtained in the form of an oil which is used as such in the subsequent syntheses.

N-Methyl-3-methylaniline may be prepared by the method described by J. A. Martus, Hormone, 10, 81 (1937); [C. A., 32, 510 (1938)].

EXAMPLE 27

The procedure is analogous to that described in Example 23, but 1.2 g of N-(4-methoxyphenyl)-2-(N-phenyl-2-phthalimidoacetamido)acetamide, 0.28 g of hydrazine hydrate and 0.38 g of 3-methylphenyl isocyanate are used as the starting material. The product obtained is purified by chromatography on 25 g of silica (0.065–0.200 mm) contained in a column 1.7 cm in diameter [eluent: methylene chloride/ethyl acetate (80-20 by volume)], collecting 25 cm³ fractions. Fractions 2 to 7 are combined and concentrated to dryness under reduced pressure (2.7 kPa) at 40° C. After recrystallization from acetonitrile, 0.12 g of N-(4-methoxyphenyl)-2-{2-[3-(3-methylphenyl)ureido]-N-phenylacetamido}acetamide melting at 194° C. is obtained.

N-(4-Methoxyphenyl)-2-(N-phenyl-2-phthalimidoacetamido)acetamide may be prepared in a manner analogous to that described in Example 23 for the preparation of N-(3-methylphenyl)-2-(N-phenyl-2-phthalimidoacetamido)acetamide, but using 2.6 g of N-[2-oxo-2-(1-imidazolyl)ethyl]-N-phenyl-2-phthalimidoacetamide and 0.84 g of 4-methoxyaniline as the starting material. 1.25 g of N-(4-methoxyphenyl)-2-(N-phenyl-2-phthalimidoacetamido)acetamide are thus obtained in the form of a meringue which is used as such as in the subsequent syntheses.

EXAMPLE 28

The procedure is analogous to that described in Example 23, but 3.1 g of N-ethyl-N-phenyl-2-(N-phenyl-2-phthalimidoacetamido)acetamide, 0.4 g of hydrazine hydrate and 0.54 g of 3-methylphenyl isocyanate are used as the starting material. The product obtained is purified by chromatography on 20 g of silica (0.065–0.200 mm) contained in a column 1.7 cm in diameter [eluent: methylene chloride], collecting 20 cm³ fractions. Fractions 10 to 23 are combined and concentrated to dryness under reduced pressure (2.7 kPa) at 40° C. After recrystallization from diethyl ether, 0.55 g of N-ethyl-N-phenyl-2-{2-[3-(3-methylphenyl)ureido]-N-phenylacetamido}acetamide melting at 158° C. is obtained.

N-Ethyl-N-phenyl-2-(N-phenyl-2-phthalimidoacetamido)acetamide may be prepared in a manner analogous to that described in Example 1 for the preparation of 2-(N-phenyl-2-phthalimidoacetamido)-N-phenylacetamide, but using 2.0 g of 2-(N-phenyl-2-phthalimidoacetamido)acetic acid, 0.76 g of oxalyl dichloride and 1.5 g of N-ethylaniline as the starting material. After recrystallization from diethyl ether, 1.8 g of N-ethyl-N-phenyl-2-(N-phenyl-2-phthalimidoacetamido)acetamide melting at 105° C. are obtained.

EXAMPLE 29

12.6 g of (RS)-3-(1-hydroxyethyl)aniline are added to a solution of 18.0 g of 2-{2-[(1-imidazolyl)carboxamido]-N-phenylacetamido}-N-methyl-N-phenylacetamide in 300 cm³ of toluene and the mixture is stirred under reflux for 4 hours. After cooling, 300 cm³ of ethyl acetate are added and the solution obtained is then washed successively with 300 cm³ of distilled water, with twice 300 cm³ of a 1N aqueous hydrochloric acid solution, with twice 300 cm³ of a saturated aqueous sodium bicarbonate solution and with 300 cm³ of a saturated aqueous sodium chloride solution. The organic phase is dried over magnesium sulphate and concentrated to dryness under reduced pressure (2.7 kPa) at 40° C. After recrystallization from ethyl acetate, 13.6 g of (RS)-2-{2-{3-[3-(1-hydroxyethyl)phenyl]ureido}-N-phenylacetamido}-N-methyl-N-phenylacetamide melting at 168° C. are obtained.

2-{2-[(1-Imidazolyl)carboxamido]-N-phenylacetamido}-N-methyl-N-phenylacetamide may be prepared in the following way: a solution of 37 g of 2-(2-amino-N-phenylacetamido)-N-methyl-N-phenylacetamide in 150 cm³ of anhydrous tetrahydrofuran is added to a solution of 31 g of N,N'-diimidazolecarbonyl in 300 cm³ of anhydrous tetrahydrofuran. The solution is stirred for 3 hours at a temperature close to 25° C. and then concentrated to dryness under reduced pressure (2.7 kPa) at 40° C. The residue is dissolved in 500 cm³ of ethyl acetate and the solution obtained is washed successively with 4 times 300 cm³ of distilled water and with 300 cm³ of a saturated aqueous sodium chloride solution. The organic phase is dried over magnesium sulphate and then concentrated to dryness under reduced pressure (2.7 kPa) at 40° C. After recrystallization from ethyl acetate, 33.3 g of 2-{2-[(1-imidazolyl)carboxamido]-N-phenylacetamido}-N-methyl-N-phenylacetamide melting at 120° C. are obtained.

EXAMPLE 30

The procedure is analogous to that described in Example 29, but 0.9 g of 2-{2-[(1-imidazolyl)carboxamido]-N-phenylacetamido}-N-methyl-N-phenylacetamide and 0.64 g of 3-methylthioaniline are used as the starting material. The product obtained is purified by chromatography on 100 g of silica (0.065–0.200 mm) contained in a column 2 cm in diameter [eluent: methylene chloride/methanol (95-5 by volume)], collecting 20 cm³ fractions. Fractions 9 to 12 are combined and concentrated to dryness under reduced pressure (2.7 kPa) at 40° C. After recrystallization from a mixture of ethyl acetate and diethyl ether (85-15 by volume), 0.22 g of N-methyl-2-{2-[3-(3-methylthiophenyl)-ureido]-N-

EXAMPLE 31

The procedure is analogous to that described in Example 29, but 3.25 g of 2-[(1-imidazolyl)carboxamido]-N-[2-oxo-2-(1,2,3,4-tetrahydro-1-quinolyl)ethyl]-N-phenylacetamide and 2.13 g of (RS)-3-(1-hydroxyethyl)aniline are used as the starting material. The product obtained is purified by chromatography on 60 g of silica (0.065-0.200 mm) contained in a column 2.0 cm in diameter [eluent: ethyl acetate], collecting 25 cm³ fractions. Fractions 8 to 15 are combined and concentrated to dryness under reduced pressure (2.7 kPa) at 40° C. After recrystallization from a mixture of diisopropyl ether and ethyl acetate (90-10 by volume), 1.7 g of (RS)-2-{3-[3-(1-hydroxyethyl)phenyl]ureido}-N-[2-oxo-2-(1,2,3,4-tetrahydro-1-quinolyl)ethyl]-N-phenylacetamide melting at 120° C. are obtained.

2-[(1-Imidazolyl)carboxamido]-N-[2-oxo-2-(1,2,3,4-tetrahydro-1-quinolyl)ethyl]-N-phenylacetamide may be prepared in a manner analogous to that described in Example 29 for the preparation of 2-{2-[(1-imidazolyl)carboxamido]-N-phenylacetamido}-N-methyl-N-phenylacetamide, but using 6.7 g of 2-amino-N-[2-oxo-2-(1,2,3,4-tetrahydro-1-quinolyl)ethyl]-N-phenylacetamide and 3.36 g of N,N'-diimidazolecarbonyl as the starting material. The product obtained is purified by chromatography on 150 g of silica (0.065-0.200 mm) contained in a column 2.7 cm in diameter [eluent: ethyl acetate/dichloromethane (80-20 by volume)], collecting 30 cm³ fractions. Fractions 6 to 13 are combined and concentrated to dryness under reduced pressure (2.7 kPa) at 40° C. 6.5 g of 2-[(1-imidazolyl)carboxamido]-N-[2-oxo-2-(1,2,3,4-tetrahydro-1-quinolyl)ethyl]-N-phenylacetamide are thus obtained in the form of a meringue which is used as such in the subsequent syntheses.

2-Amino-N-[2-oxo-2-(1,2,3,4-tetrahydro-1-quinolyl)ethyl]-N-phenylacetamide may be prepared in a manner analogous to that described in Example 2 for the preparation of 2-(2-amino-N-phenylacetamido)-N-methyl-N-phenylacetamide, but using 4.5 g of N-[2-oxo-2-(1,2,3,4-tetrahydro-1-quinolyl)ethyl]-N-phenyl-2-phthalimidoacetamide and 1.0 g of hydrazine hydrate as the starting material. 2.2 g of 2-amino-N-[2-oxo-2-(1,2,3,4-tetrahydro-1-quinolyl)ethyl]-N-phenylacetamide are thus obtained in the form of an oil which is used as such in the subsequent syntheses.

EXAMPLE 32

The procedure is analogous to that described in Example 29, but 3.25 g of 2-[(1-imidazolyl)carboxamido]-N-[2-oxo-2-(1,2,3,4-tetrahydro-1-quinolyl)ethyl]-N-phenylacetamide and 2.16 g of 3-methylthioaniline are used as the starting material. The product obtained is purified by chromatography on 60 g of silica (0,065-0,200 mm) contained in a column 1.7 cm in diameter [eluent: ethyl acetate/cyclohexane (75-25 by volume)], collecting 25 cm³ fractions. Fractions 11 to 18 are combined and concentrated to dryness under reduced pressure (2.7 kPa) at 40° C. After recrystallization from diisopropyl ether, 1.3 g of 2-[3-(3-methylthiophenyl)ureido]-N-[2-oxo-2-(1,2,3,4-tetrahydro-1-quinolyl)ethyl]-N-phenylacetamide melting at 110° C. are obtained.

EXAMPLE 33

The procedure is analogous to that described in Example 29, but 2.0 g of N-[2-(3,3-dimethylpiperidino)-2-oxoethyl]-2-[(1-imidazolyl)carboxamido]-N-phenylacetamide and 1.38 g of (RS)-3-(1-hydroxyethyl)aniline are used as the starting material. After recrystallization from a mixture of ethanol and diisopropyl ether (50-50 by volume), 1.4 g of (RS)-N-[2-(3,3-dimethylpiperidino)-2-oxoethyl]-2-{3-[3-(1-hydroxyethyl)phenyl]ureido}-N-phenylacetamide melting at 200° C. are obtained.

N-[2-(3,3,-Dimethylpiperidino)-2-oxoethyl]-2-(1-imidazolyl)carboxamido]-N-phenylacetamide may be prepared in a manner analogous to that described in Example 29 for the preparation of 2-{2-[(1-imidazolyl)carboxamido]-N-phenylacetamido}-N-methyl-N-phenylacetamide, but using 6.8 g of 2-amino-N-[2-oxo-2-(3,3-dimethylpiperidino)ethyl]-N-phenylacetamide and 3.7 g of N,N'-diimidazolecarbonyl as the starting material. After recrystallization from diisopropyl ether, 6.4 g of N-[2-(3,3-dimethylpiperidino)-2-oxoethyl]-2-[(1-imidazolyl)carboxamido]-N-phenylacetamide melting at 104° C. are thus obtained.

EXAMPLE 34

The procedure is analogous to that described in Example 29, but 2.0 g of N-[2-(3,3-dimethylpiperidino)-2-oxoethyl]-2-[(1-imidazolyl)carboxamido]-N-phenylacetamide and 1.25 g of 3-methoxyaniline are used as the starting material. After recrystallization from a mixture of acetonitrile and diisopropyl ether (50-50 by volume), 0.96 g of N-[2-(3,3-dimethylpiperidino)-2-oxoethyl]-2-[3-(3-methoxyphenyl)ureido]-N-phenylacetamide melting at 200° C. is obtained.

EXAMPLE 35

The procedure is analogous to that described in Example 29, but 2.0 g of N-[2-(3,3-dimethylpiperidino)-2-oxoethyl]-2-[(1-imidazolyl)carboxamido]-N-phenylacetamide and 1.4 g of 3-methylthioaniline are used as the starting material. After recrystallization from an ethyl acetate/diisopropyl ether mixture (50-50 by volume), 1.1 g of N-[2-(3,3-dimethylpiperidino)-2-oxoethyl]-2-[3-(3-methylthiophenyl)ureido]-N-phenylacetamide melting at 172° C. are obtained.

EXAMPLE 36

The procedure is analogous to that described in Example 29, but 1.8 g of (RS)-2-{2-[(1-imidazolyl)carboxamido]-N-phenylacetamido}-N-methyl-N-phenylpropionamide and 1.24 g of (RS)-3-(1-hydroxyethyl)aniline are used as the starting material. The product obtained is purified by chromatography on 30 g of silica (0.065-0.200 mm) contained in a column 2.2 cm in diameter [eluent: ethyl acetate/cyclohexane (80-20 by volume)], collecting 25 cm³ fractions. Fractions 7 to 17 are combined and concentrated to dryness under reduced pressure (2.7 kPa) at 40° C. After recrystallization from ethyl acetate, 0.9 g of (RS)-2-{2-{3-[(RS)-3-(1-hydroxyethyl)phenyl]ureido}-N-phenylacetamido}-N-methyl-N-phenylpropionamide melting at 185° C. are obtained.

(RS)-2-{2-[(1-Imidazolyl)carboxamido]-N-phenylacetamido}-N-methyl-N-phenylpropionamide may be prepared in a manner analogous to that described in Example 29 for the preparation of 2-{2-[(1-imidazolyl)carboxamido]-N-phenylacetamido}-N-methyl-N-phenylacetamide, but using 5.1 g of (RS)-2-

(2-amino-N-phenylacetamido)-N-methyl-N-phenylpropionamide and 3.1 g of N,N'-diimidazolecarbonyl as the starting material. 5.0 g of (RS)-2-{2-[(1-imidazolyl)carboxamido]-N-phenylacetamido}-N-methyl-N-phenylpropionamide are thus obtained in the form of a meringue which is used as such in the subsequent syntheses.

EXAMPLE 37

The procedure is analogous to that described in Example 29, but 3.2 g of (RS)-2-{2-[(1-imidazolyl)carboxamido]-N-phenylacetamido}-N-methyl-N-phenylpropionamide and 2.2 g of 3-methylthioaniline are used as the starting material. The product obtained is purified by chromatography on 100 g of silica gel (0.065–0.200 mm) contained in a column 3.3 cm in diameter [eluent: ethyl acetate/methylene chloride (50-50 by volume)], collecting 50 cm³ fractions. Fractions 22 to 32 are combined and concentrated to dryness under reduced pressure (2.7 kPa) at 40° C. After recrystallization from acetonitrile, 1.5 g of (RS)-N-methyl-2-{2-[3-(3-methylthiophenyl)ureido]-N-phenylacetamido}-N-phenylpropionamide melting at 175° C. are obtained.

EXAMPLE 38

The procedure is analogous to that described in Example 29, but 2.0 g of (RS)-N-[1-(3,3-dimethylpiperidino)-1-oxo-2-propyl]-2-[(1-imidazolyl)carboxamido]-N-phenylacetamide and 1.38 g of (RS)-3-(1-hydroxyethyl)aniline are used as the starting material. The product obtained is purified by chromatography on 40 g of silica (0.065–0.200 mm) contained in a column 2.4 cm in diameter [eluent: methylene chloride/ethyl acetate (40-60 by volume)], collecting 25 cm³ fractions. Fractions 6 to 13 are combined and concentrated to dryness under reduced pressure (2.7 kPa) at 40° C. After recrystallization from ethyl acetate, 0.6 g of N-[(RS)-1-(3,3-dimethylpiperidino)-1-oxo-2-propyl]-2-{3-[(RS)-3-(1-hydroxyethyl)phenyl]ureido}-N-phenylacetamide melting at 186° C. is obtained.

(RS)-N-[1-(3,3-Dimethylpiperidino)-1-oxo-2-propyl]-2-[(1-imidazolyl)carboxamido]-N-phenylacetamide may be prepared in a manner analogous to that described in Example 29 for the preparation of 2-{2-[(1-imidazolyl)carboxamido]-N-phenylacetamido}-N-methyl-N-phenylacetamide, but using 5.1 g of (RS)-2-amino-N-[1-(3,3-dimethylpiperidino)-1-oxo-2-propyl]-N-phenylacetamide and 3.1 g of N,N'-diimidazolecarbonyl as the starting material. 6.0 g of (RS)-N-[1-(3,3-dimethylpiperidino)-1-oxo-2-propyl]-2-[(1-imidazolyl)carboxamido]-N-phenylacetamide are thus obtained in the form of a meringue which is used as such in the subsequent syntheses.

EXAMPLE 39

The procedure is analogous to that described in Example 29, but 3.6 g of (RS)-N-[1-(3,3-dimethylpiperidino)-1-oxo-2-propyl]-2- [(1-imidazolyl)carboxamido]-N-phenylacetamide and 2.44 g of 3-methylthioaniline are used as the starting material. The product obtained is purified by chromatography on 90 g of silica (0.065–0.200 mm) contained in a column 3.3 cm in diameter [eluent: methylene chloride/ethyl acetate (50-50 by volume)], collecting 30 cm³ fractions. Fractions 17 to 24 are combined and concentrated to dryness under reduced pressure (2.7 kPa) at 40° C. After recrystallization from a mixture of diethyl ether and ethyl acetate (60-2 by volume), 2.1 g of (RS)-N-[1-(3,3-dimethylpiperidino)-1-oxo-2-propyl]-2-[3-(3-methylthiophenyl)ureido]-N-phenylacetamide melting at 130° C are obtained.

EXAMPLE 40

A suspension of 1.6 g of (RS)-1-(α-phenylaminophenylacetyl)pyrrolidine and 1.2 g of 2-[3-(3-methylphenyl)ureido]acetic acid in 50 cm³ of anhydrous 1,2-dichlorethane is heated to reflux. 0.68 g of thionyl chloride is added, maintaining reflux until the evolution of gas has ceased. The reaction mixture is then poured into 30 cm³ of a saturated aqueous sodium bicarbonate solution and 50 cm³ of methylene chloride are then added. The organic phase is washed with 50 cm³ of distilled water, dried over magnesium sulphate and concentrated to dryness under reduced pressure (2.7 kPa) at 40° C. The product obtained is purified by chromatography on 50 g of silica (0.065–0.200 mm) contained in a column 2.2 cm in diameter [eluent: ethyl acetate/methylene chloride (50-50 by volume)], collecting 25 cm³ fractions. Fractions 9 to 22 are combined and concentrated to dryness under reduced pressure (2.7 kPa) at 40° C. After recrystallization from a mixture of ethyl acetate and acetonitrile (90-10 by volume), 0.55 g of (RS)-2-[3-(3-methylphenyl)ureido]-N-[2-oxo-1-phenyl-2-(1-pyrrolidinyl)ethyl]-N-phenylacetamide melting at 138° C. is obtained.

(RS)-1-(α-Phenylaminophenylacetyl)pyrrolidine may be prepared in a manner analogous to that described in Example 21 for the preparation of (RS)-3,3-dimethyl-1-(2-phenylaminopropionyl)piperidine, but using 2.58 g of α-bromophenylacetyl chloride, 0.77 g of pyrrolidine, 1.52 g of triethylamine and 3.0 g of aniline as the starting material. After recrystallization from petroleum ether, 1.65 g of (RS)-1-(α-phenylaminophenylacetyl)pyrrolidine melting at 65° C are obtained.

2-[3-(3-Methylphenyl)ureido]acetic acid may be prepared in the following way: 53 g of 3-methylphenyl isocyanate are added in the course of 15 minutes to a solution of 30 g of glycine and 53 g of sodium bicarbonate in 600 cm³ of distilled water. The reaction mixture is stirred for 4 hours at a temperature close to 25° C, then washed with 200 cm³ of ethyl acetate and acidified to pH 1 with 200 cm³ of a 4N hydrochloric acid solution. The product obtained is separated off by filtration, washed with water and air-dried. 72 g of 2-[3-(3-methylphenyl)ureido]acetic acid melting at 208° C are thus obtained.

EXAMPLE 41

The procedure is analogous to that described in Example 40, but 2.4 g of (RS)-2-anilino-N-tert-butylphenylacetamide, 1.2 g of 2-[3-(3-methylphenyl)ureido]acetic acid and 1.0 g of thionyl chloride are used as the starting material. The product obtained is purified by chromatography on 50 g of silica (0.065–0.200 mm) contained in a column 1.7 cm in diameter [eluent: ethyl acetate/methylene chloride (20-80 by volume)], collecting 30 cm³ fractions. Fractions 5 to 7 are combined and concentrated to dryness under reduced pressure (2.7 kPa) at 40° C. After recrystallization from acetonitrile, 0.8 g of (RS)-N-tert-butyl-2-{2-[3-(3-methylphenyl)ureido]-N-phenylacetamido} phenylacetamide melting at 216° C is obtained.

(RS)-2-Anilino-N-tert-butylphenylacetamide may be prepared in a manner analogous to that described in Example 21 for the preparation of (RS)-3,3-dimethyl-1-(2-phenylaminopropionyl)piperidine, but using 2.6 g of α-bromophenylacetyl chloride, 0.77 g of tert-butylamine, 1.51 g of triethylamine and 3.1 g of aniline as the starting material. 2.55 g of (RS)-2-anilino-N-tert-butylphenylacetamide are obtained in the form of an oil which is used as such in the subsequent syntheses.

EXAMPLE 42

The procedure is analogous to that described in Example 40, but 0.62 g of 2-[3-(3-methylphenyl)ureido]acetic acid, 0.9 g of tert-butyl (RS)-2-anilino-2-[(1-pyrrolidinyl)carbonyl]acetate and 0.21 cm³ of thionyl chloride are used as the starting material. After recrystallization from 8 cm³ of a mixture of diethyl ether and ethyl acetate (90-10 by volume), 0.65 g of tert-butyl (RS)-2-{2-[3-(3-methylphenyl)ureido]-N-phenylacetamido}-2-[(1-pyrrolidinyl)carbonyl]acetate melting at 148° C. is thus obtained.

tert-Butyl (RS)-2-anilino-2-[(1-pyrrolidinyl)carbonyl]acetate may be prepared in the following way: 1.8 cm³ of aniline are added to a solution of 4.4 g of tert-butyl (RS)-2-bromo-2-[(1-pyrrolidinyl)carbonyl]acetate in 15 cm³ of acetonitrile and the reaction mixture is kept under reflux for 5 hours and then at a temperature close to 20° C for 20 hours. The insoluble product is separated off by filtration and the filtrate is concentrated to dryness under reduced pressure (2.7 kPa). After recrystallization from 10 cm³ of diisopropyl ether, 0.95 g of tert-butyl (RS)-2-anilino-2-[(1-pyrrolidinyl)carbonyl]acetate melting at 80° C is obtained.

tert-Butyl (RS)-2-bromo-2-[(1-pyrrolidinyl)carbonyl]acetate may be prepared in the following way: 0.51 cm³ of bromine is added dropwise to a solution of 2.6 g of tert-butyl 2-[(1-pyrrolidinyl)carbonyl]acetate and 1.18 g of acetamide in 45 cm³ of chloroform, which is kept under reflux, and the mixture is heated under reflux for 11 hours. After cooling, the insoluble matter is separated off by filtration and the filtrate is washed with twice 10 cm³ of a saturated sodium bicarbonate solution, dried over sodium sulphate and then concentrated to dryness under reduced pressure (2.7 kPa) at 35° C. 4.4 g of tert-butyl (RS)-2-bromo-2-[(1-pyrrolidinyl)carbonyl]acetate are thus obtained in the form of an oil which is used as such in the subsequent syntheses.

tert-Butyl 2-[(1-pyrrolidinyl)carbonyl]acetate may be prepared in the following way: 0.84 cm³ of pyrrolidine and then a solution of 2.1 g of dicyclohexylcarbodiimide in 10 cm³ of dichloromethane are added to a solution of 1.6 g of tert-butyl hydrogen malonate in 16 cm³ of dichloromethane, which is kept at a temperature close to 0° C. The mixture is stirred for 7 days at a temperature close to 25° C, the insoluble matter is separated off by filtration and the filtrate is concentrated to dryness under reduced pressure <2.7 kPa) at 35° C. 2.6 g of tert-butyl 2-[(1-pyrrolidinyl)carbonyl]acetate are thus obtained in the form of an oil which is used as such in the subsequent syntheses.

tert-Butyl hydrogen malonate may be prepared by the method described in Acta Chem. Scand. B29, 687 (1975).

EXAMPLE 43

The procedure is analogous to that described in Example 40, but 2.2 g of 2-[3-(3-methylphenyl)ureido]acetic acid, 3.4 g of tert-butyl (RS)-2-anilino-2-phenylcarbamoylacetate and 0.75 cm³ of thionyl chloride are used as the starting material. After recrystallization from 8 cm³ of a mixture of diethyl ether and ethyl acetate (90-10 by volume), 0.45 g of tert-butyl (RS)-2-{2-[3-(3-methylphenyl)ureido]-N-phenylacetamido}-2-phenylcarbamoylacetate melting at 176° C is thus obtained.

tert-Butyl (RS)-2-anilino-2-phenylcarbamoylacetate may be prepared in a manner analogous to that described in Example 42 for the preparation of tert-butyl (RS)-2-anilino-2-[(1-pyrrolidinyl)carbonyl]acetate, but using 20.4 g of tert-butyl (RS)-2-bromo-2-phenylcarbamoylacetate and 9.1 cm³ of aniline in 100 cm³ of acetonitrile as the starting material. After recrystallization from 25 cm³ of diisopropyl ether, 3.4 g of tert-butyl (RS)-2-anilino-2-phenylcarbamoylacetate melting at 125° C are obtained.

tert-Butyl (RS)-2-bromo-2-phenylcarbamoylacetate may be prepared in a manner analogous to that described in Example 42 for the preparation of tert-butyl (RS)-2-bromo-2-[(1-pyrrolidinyl)carbonyl]acetate, but using 16 g of tert-butyl 2-phenylcarbamoylacetate, 5.9 g of acetamide and 8 cm³ of bromine as the starting material. 20.4 g of tert-butyl <RS)-2-bromo-2-phenylcarbamoylacetate are thus obtained in the form of an oil which is used as such in the subsequent syntheses.

tert-Butyl 2-phenylcarbamoylacetate may be prepared in a manner analogous to that described in Example 42 for the preparation of tert-butyl 2-[(1-pyrrolidinyl)carbonyl]acetate, but using 8 g of tert-butyl hydrogen malonate, 4.5 cm³ of aniline and 10.5 g of dicyclohexylcarbodiimide as the starting material. 16 g of tert-butyl 2-phenylcarbamoylacetate are thus obtained in the form of an oil which is used as such in the subsequent syntheses.

EXAMPLE 44

The procedure is analogous to that described in Example 29, but 1.95 g of 2-{2-[(1-imidazolyl)carboxamido]-N-phenylacetamido}-N-methyl-N-phenylacetamide and 1.2 g of 3-ethylaniline are used as the starting material. The crude product obtained is purified by chromatography on 50 g of silica (0.065-0.200 mm) contained in a column 2 cm in diameter [eluent: cyclohexane/ethyl acetate (40-60 by volume)], collecting 25 cm³ fractions. Fractions 7 to 13 are combined and concentrated to dryness under reduced pressure (2.7 kPa) at 40° C. After recrystallization from diisopropyl ether, 0.75 g of 2-{2-[3-(3-ethylphenyl)ureido]-N-phenylacetamido}-N-methyl-N-phenylacetamide melting at 105° C is obtained.

EXAMPLE 45

The procedure is analogous to that described in Example 29, but 1.95 g of 2-{2-[(1-imidazolyl)carboxamido]-N-phenylacetamido}-N-methyl-N-phenylacetamide and 1.2 g of 3-aminobenzyl alcohol are used as the starting material. The product obtained is purified by chromatography on 50 g of silica (0.065-0.200 mm) contained in a column 1.5 cm in diameter [eluent: methylene chloride/ethanol (95-5 by volume)], collecting 20 cm³ fractions. Fractions 6 to 13 are combined and concentrated to dryness under reduced pressure (2.7 kPa) at 40° C. After recrystallization from diisopropyl ether, 1 g of 2-{2-[3-(3-hydroxymethylphenyl)ureido]-N-phenylacetamido}-N-methyl-N-phenylacetamide melting at 120° C is obtained.

EXAMPLE 46

The procedure is analogous to that described in Example 29, but 2.0 g of 2-{2-[(1-imidazolyl)carboxamido]-N-phenylacetamido}-N-methyl-N-phenylacetamide mide and 1.55 g of (RS)-1-(3-aminophenyl)butanol are used as the starting material. The crude product obtained is purified by chromatography on 50 g of silica (0.065–0.200 mm) contained in a column 1.5 cm in diameter [eluent: dichloromethane/ethyl acetate (50-50 by volume)], collecting 25 cm³ fractions. Fractions 20 to 29 are combined and concentrated to dryness under reduced pressure (2.7 kPa) at 40° C. After recrystallization from ethyl acetate, 0.9 g of (RS)-2-{-2-{3-[3-(1-hydroxybutyl)phenyl]ureido}-N-phenylacetamido}-N-methyl-N-phenylacetamide melting at 154° C is thus obtained.

(RS)-1-(3-Aminophenyl)butanol may be prepared in the following way: 0.2 g of 5% palladium-on-charcoal is added to a solution of 2.2 g of (RS)-1-(3-nitrophenyl)butanol in 40 cm³ of ethanol. The suspension is stirred for 2 hours at a temperature close to 25° C under a hydrogen atmosphere (100 kPa). The catalyst is then separated off and the filtrate is concentrated to dryness under reduced pressure (2.7 kPa) at 40° C. 1.8 g of (RS)-1-(3-aminophenyl)butanol are thus obtained in the form of an oil which is used as such in the subsequent syntheses.

(RS)-1-(3-Nitrophenyl)butanol may be prepared by the method described by E. Felder et al., J. Med. Chem., 13, 559 (1970).

EXAMPLE 47

The procedure is analogous to that described in Example 29, but 2.0 g of 2-{2-[(1-imidazolyl)carboxamido]-N-phenylacetamido}-N-methyl-N-phenylacetamide and 1.1 g of 3-aminophenol are used as the starting material. After recrystallization from methanol, 0.8 g of 2-{2-[3-(3-hydroxyphenyl)ureido]-N-phenylacetamido}-N-methyl-N-phenylacetamide melting at 180° C is obtained.

EXAMPLE 48

The procedure is analogous to that described in Example 29, but 2.35 g of 2-{2-[(1-imidazolyl)carboxamido]-N-phenylacetamido}-N-methyl-N-phenylacetamide and 1.65 g of 2-(3-aminophenyl)ethanol are used as the starting material. The crude product obtained is purified by chromatography on 150 g of silica (0.065–0.200 mm) contained in a column 4.1 cm in diameter [eluent: methylene chloride/ethanol (96-4 by volume)], collecting 20³ fractions. Fractions 17 to 32 are combined and concentrated to dryness under reduced pressure (2.7 kPa) at 40° C. After recrystallization from acetonitrile, 0.89 g of 2-{2-{3-[3-(2-hydroxyethyl)phenyl]ureido}-N-phenylacetamido}-N-methyl-N-phenylacetamide melting at 152° C is obtained.

2-(3-Aminophenyl)ethanol may be prepared by the method described by B. Carnmalm et al., Acta Pharm. Suecica, 11, 33 (1974).

EXAMPLE 49

The procedure is analogous to that described in Example 29, but 1.58 g of N-[2-(3,3-dimethylpiperidino)-2-oxoethyl]-2-[(1-imidazolyl)carboxamido]-N-phenylacetamide and 0.98 g of 3-hydroxymethylaniline are used as the starting material. After recrystallization from a dimethylformamide/acetonitrile mixture (25-75 by volume), 1.0 g of N-[2-(3,3-dimethylpiperidino)-2-oxoethyl]-2-[3-(3-hydroxymethylphenyl)ureido]-N-phenylacetamide melting at 248° C is obtained.

EXAMPLE 50

The procedure is analogous to that described in Example 29, but 2.0 g of N-[2-(3,3-dimethylpiperidino)-2-oxoethyl]-2-[(1-imidazolyl)carboxamido]-N-phenylacetamide and 1.4 g of 2-(3-aminophenyl)ethanol are used as the starting material. After recrystallization from acetonitrile, 0.45 g of N-[2-(3,3-dimethylpiperidino)-2-oxoethyl]-2-{3-[3-(2-hydroxyethyl)phenyl]ureido}-N-phenylacetamide melting at 175° C is obtained.

EXAMPLE 51

The procedure is analogous to that described Example 1, but 1.5 g of (RS)-2-amino-N-[1-oxo-1-(1,2,3,4-tetrahydro-1-quinolyl)-2-propyl]-N-phenylacetamide and 0.59 g of 3-methylphenyl isocyanate are used as the starting material. After recrystallization from an acetonitrile/dimethylformamide mixture (96-4 by volume), 1.4 g of (RS)-2-[3-(3-methylphenyl)ureido]-N-[1-oxo-1-(1,2,3,4,-tetrahydro-1-quinolyl)-2-propyl]-N-phenylacetamide melting at 215° C are obtained.

(RS)-2-Amino-N-[1-oxo-1-(1,2,3,4-tetrahydro-1-quinolyl)-2-propyl]-N-phenylacetamide may be prepared in a manner analogous to that described in Example 1 for the preparation of 2-(2-amino-N-phenylacetamido)-N-phenylacetamide, but using 9.7 g of (RS)-N-[1-oxo-1-(1,2,3,4-tetrahydro-1-quinolyl)-2-propyl]-N-phenyl-2-phthalimidoacetamide and 2.07 g of hydrazine hydrate as the starting material. 6.8 g of (RS)-2-amino-N-[1-oxo-1-(1,2,3,4-tetrahydro-1-quinolyl)-2-propyl]-N-phenylacetamide is thus obtained in the form of an oil which is used as such in the subsequent syntheses.

(RS)-N-[1-Oxo-1-(1,2,3,4-tetrahydro-1-quinolyl)-2-propyl]-N-phenyl-2-phthalimidoacetamide may be prepared in a manner analogous to that described in Example 1 for the preparation of tert-butyl 2-(N-phenyl-2-phthalimidoacetamido)acetate but using 7.8 g of (RS)-1-(2-phenylaminopropionyl)-1,2,3,4-tetrahydroquinoline and 6.2 g of 2-phthalimidoacetyl chloride as the starting material. 9.8 g of (RS)-N-[1-oxo-1-(1,2,3,4-tetrahydro-1-quinolyl)-2-propyl]-N-phenyl-2-phthalimidoacetamide melting at 191° C are thus obtained.

(RS)-1-(2-Phenylaminopropionyl)-1,2,3,4-tetrahydroquinoline may be prepared in a manner analogous to that described in Example 21 for the preparation of (RS)-3,3-dimethyl-1-(2-phenylaminopropionyl)piperidine, but using 8.5 g of 2-bromopropionyl chloride, 6.6 g of 1,2,3,4-tetrahydroquinoline, 6.1 g of triethylamine and 7 g of aniline as the starting material. After recrystallization from cyclohexane, 7.8 g of (RS)-1-(2-phenylaminopropionyl)-1,2,3,4-tetrahydroquinoline melting at 98° C are obtained.

EXAMPLE 52

The procedure is analogous to that described in Example 29, but 2 g of (RS)-2-[(1-imidazolyl)carboxamido]-N-[1-oxo-1-(1,2,3,4-tetrahydro-1-quinolyl)-2-propyl]-N-phenylacetamide and 1.3 g of (RS)-1-(3-aminophenyl)ethanol are used as the starting material. The crude product obtained is purified by chromatography on 40 g of silica (0.065–0.200 mm) contained in a column 2.4 cm in diameter [eluent: dichloromethane/ethyl acetate (60-40 by volume)], collecting 25 cm³ fractions. Fractions 15 to 21 are combined and concentrated to dryness under reduced pressure (2.7 kPa) at 40° C. After recrystallization from ethyl acetate, 0.9 g of (RS)-2-{3-[(RS)-3-(1-hydroxyethyl)phenyl-]ureido}-N-[1-oxo-1-(1,2,3,4-tetrahydro-1-quinolyl)-2-propyl]-N-phenylacetamide melting at 170° C is obtained.

(RS)-2-[(1-Imidazolyl)carboxamido]-N-[1-oxo-1-(1,2,3,4-tetrahydro-1-quinolyl)-2-propyl]-N-phenylacetamide may be prepared in a manner analogous to that described in Example 29 for the preparation of 2-{2-[(1-imidazolyl)carboxamido]-N-phenylacetamido}-N-methyl-N-phenylacetamide, but using 5.3 g of (RS)-2-amino-N-[1-oxo-1-(1,2,3,4-tetrahydro-1-quinolyl)-2-propyl]-N-phenylacetamide and 3.07 g of N,N'-diimidazolecarbonyl as the starting material. 6.5 g of (RS)-2-[(1-imidazolyl)carboxamido]-N-[1-oxo-1-(1,2,3,4-tetrahydro-1-quinolyl)-2-propyl]-N-phenylacetamide are thus obtained in the form of a meringue which is used as such in the subsequent syntheses.

EXAMPLE 53

The procedure is analogous to that described in Example 29, but 2.0 g of (RS)-2-[(1-imidazolyl)carboxamido]-N-[1-oxo-1-(1,2,3,4-tetrahydro-1-quinolyl)-2-propyl]-N-phenylacetamide and 1.28 g of 3-methylthioaniline are used as the starting material. The crude product obtained is purified by chromatography on 40 g of silica (0.065-0.200 mm) contained in a column 2.4 cm in diameter [eluent: dichloromethane/ethyl acetate (70-30 by volume)], collecting 25 cm³ fractions. Fractions 12 to 20 are combined and concentrated to dryness under reduced pressure (2.7 kPa) at 40° C. After recrystallization from a diethyl ether/ethyl acetate mixture (90-10 by volume), 0.75 g of (RS)-2-[3-(3-methylthiophenyl)ureido]-N-[1-oxo-1-(1,2,3,4-tetrahydro-1-quinolyl)-2-propyl]-N-phenylacetamide melting at 165° C is obtained.

EXAMPLE 54

1.5 g of triethylamine and then 2.7 g of indole-2-carbonyl chloride in solution in 20 cm³ of 1,2-dichloroethane are added to a solution of 3 g of 2-(2-amino-N-phenylacetamido)-N-methyl-N-phenylacetamide in 50 cm³ of 1,2-dichloroethane at a temperature close to 25° C and the reaction mixture is stirred for 18 hours at a temperature close to 25° C. 50 cm³ of dichloromethane and then 30 cm³ of a saturated aqueous sodium bicarbonate solution are then added. The organic phase is washed with twice 30 cm³ of distilled water, dried over magnesium sulphate and concentrated to dryness under reduced pressure (2.7 kPa) at 40° C. After recrystallization from a dimethylformamide/methanol mixture (65-35 by volume), 0.6 g of N-[N-(N-methyl-N-phenylcarbamoylmethyl)-N-phenylcarbamoylmethyl]indole-2-carboxamide melting at 255° C is obtained.

Indole-2-carbonyl chloride may be prepared in the following way: 0.2 cm³ of dimethyl formamide and then 3.25 g of oxalyl dichloride in solution in 20 cm³ of anhydrous diethyl ether are added to a suspension of 4.0 g of indole-2-carboxylic acid in 80 cm³ of anhydrous diethyl ether at a temperature close to 5° C. The reaction mixture is stirred at a temperature close to 25° C for 2 hours and the ether phase is then concentrated to dryness under reduced pressure (2.7 kPa) at 30° C. 4.0 g of indole-2-carbonyl chloride melting at 120° C are thus obtained.

EXAMPLE 55

1.8 g of oxalyl dichloride are added in the course of 5 minutes to a suspension of 2.4 g of naphthalene-2-carboxylic acid in 50 cm³ of anhydrous diethyl ether. The mixture is stirred for 3 hours at a temperature close to 25° C and then concentrated to dryness under reduced pressure (2.7 kPa) at 30° C. The residue obtained is dissolved in 25 cm³ of 1,2-dichloroethane and the solution is added in the course of 10 minutes to a mixture of 3.8 g of 2-(2-amino-N-phenylacetamido)-N-methyl-N-phenylacetamide and 2.0 g of triethylamine in 50 cm³ of dichloromethane kept at a temperature close to 5° C. The mixture is stirred for 16 hours at a temperature close to 25° C. 50 cm³ of dichloromethane and 30 cm³ of a saturated aqueous sodium bicarbonate solution are then added. The organic phase is washed with twice 30 cm³ of distilled water, dried over magnesium sulphate and concentrated to dryness under reduced pressure (2.7 kPa) at 40° C. After recrystallization from ethyl acetate, 1.4 g of N-[N-(N-methyl-N-phenylcarbamoyl-methyl)-N-phenylcarbamoyl-methyl]naphthalene-2-carboxamide melting at 134° C are obtained.

EXAMPLE 56

The procedure is analogous to that described in Example 1, but 3.1 g of 2-amino-N-[2-(3,4-dihydro-1,4-2H-benzothiazin-4-yl)-2-oxoethyl]-N-phenylacetamide and 1.2 g of 3-methylphenyl isocyanate are used as the starting material. After recrystallization from ethyl acetate, 2.4 g of N-[2-(3,4-dihydro-1,4-2H-benzothiazin-4-yl)-2-oxoethyl]-2-[3-(3-methylphenyl)ureido]-N-phenylacetamide melting at 170° C are obtained.

2-Amino-N-[2-(3,4-dihydro-1,4-2H-benzothiazin-4-yl)-2-oxoethyl]-N-phenylacetamide may be prepared in a manner analogous to that described in Example 1 for the preparation of 2-(2-amino-N-phenyl-acetamido)-N-phenylacetamide, but using 4.5 g of N-[2-(3,4-dihydro-1,4-2H-benzothiazin-4-yl)-2-oxoethyl]-N-phenyl-2-phthalimidoacetamide and 0.95 g of hydrazine hydrate as the starting material. 3.1 g of 2-amino-N-[2-(3,4-dihydro-1,4-2H-benzothiazin-4-yl)-2-oxoethyl]-N-phenylacetamide are thus obtained in the form of an oil which is used as such in the subsequent syntheses.

N-[2-(3,4-Dihydro-1,4-2H-benzothiazin-4-yl)-2-oxoethyl]-N-phenyl-2-phthalimidoacetamide may be prepared in a manner analogous to that described in Example 1 for the preparation of 2-(N-phenyl-2-phthalimidoacetamido)-N-phenylacetamide, but using 5.1 g of 2-(N-phenyl-2-phthalimidoacetamido)acetic acid, 2.1 g of oxalyl dichloride and 6 g of 3,4-dihydro-1,4-2H-benzothiazine as the starting material. After recrystallization from ethanol, 4.5 g of N-[2-(3,4-dihydro-1,4-2H-benzothiazin-4-yl)-2-oxoethyl]-N-phenyl-2-phthalimidoacetamide melting at 120° C are obtained.

3,4-Dihydro-1,4-2H-benzothiazine may be prepared by the method described by C. C. J. Culvenor et al., J. Chem. Soc., 278 (1949).

EXAMPLE 57

The procedure is analogous to that described in Example 1, but 1.2 g of cis-2-amino-N-[2-(2,6-dimethylpiperidino)-2-oxoethyl]-N-phenylacetamide and 0.61 g of 3-methylphenyl isocyanate are used as the starting material. After recrystallization from an ethyl acetate/acetonitrile mixture (50-50 by volume), 20 0.75 g of cis-N-[2-(2,6-dimethylpiperidino)-2-oxoethyl]-2-[3-

(3-methylphenyl)ureido]-N-phenylacetamide melting at 212° C is obtained.

cis-2-Amino-N-[2-(2,6-dimethylpiperidino)-2-oxoethyl]-N-phenylacetamide may be prepared in a manner analogous to that described in Example 1 for the preparation of 2-(2-amino-N-phenylacetamido)-N-phenylacetamide, but using 3.3 g of cis-N-[2-(2,6-dimethylpiperidino)-2-oxoethyl]-N-phenyl-2-phthalimidoacetamide and 0.82 g of hydrazine hydrate as the starting material. 1.2 g of cis-2-amino-N-[2-(2,6-dimethylpiperidino)-2-oxoethyl]-N-phenylacetamide are thus obtained in the form of an oil which is used as such in the subsequent syntheses.

cis-N-[2-(2,6-Dimethylpiperidino)-2-oxoethyl]-N-phenyl-2-phthalimidoacetamide may be prepared in a manner analogous to that described in Example 1 for the preparation of 2-(N-phenyl-2-phthalimidoacetamido)-N-phenylacetamide, but using 3.38 g of 2-(N-phenyl-2-phthalimidoacetamido)acetic acid, 1.4 g of oxalyl dichloride and 2.5 g of cis-2,6-dimethylpiperidine as the starting material. 3.3 g of cis-N-[2-(2,6-dimethylpiperidino)-2-oxoethyl]-N-phenyl-2-phthalimidoacetamide are thus obtained in the form of a meringue which is used as such in the subsequent syntheses.

EXAMPLE 58

The procedure is analogous to that described in Example 1, but 2.4 g of 2-amino-N-[2-(3,4-dihydro-1,4-2H-benzoxazin-4-yl)-2-oxoethyl]-N-phenylacetamide and 0.98 g of 3-methylphenyl isocyanate are used as the starting material. After recrystallization from acetonitrile, 1.6 g of N-[2-(3,4-dihydro-1,4-2H-benzoxazin-4-yl)-2-oxoethyl]-2-[3-(3-methylphenyl)ureido]-N-phenylacetamide melting at 185° C. are obtained.

2-Amino-N-[2-(3,4-dihydro-1,4-2H-benzoxazin-4-yl)-2-oxoethyl]-N-phenylacetamide may be prepared in a manner analogous to that described in Example 1 for the preparation of 2-(2-amino-N-phenylacetamido)-N-phenylacetamide, but using 3.8 g of N-[2-(3,4-dihydro-1,4-2H-benzoxazin-4-yl)-2-oxoethyl]-N-phenyl-2-phthalimidoacetamide and 0.83 g of hydrazine hydrate as the starting material. 2.4 g of 2-amino-N-[2-(3,4-dihydro-1,4-2H-benzoxazin-4-yl)-2-oxoethyl]-N-phenylacetamide are thus obtained in the form of an oil which is used as such in the subsequent syntheses.

N-[2-(3,4-Dihydro-1,4-2H-benzoxazin-4-yl)-2-oxoethyl]-N-phenyl-2-phthalimidoacetamide may be prepared in a manner analogous to that described in Example 1 for the preparation of 2-(N-phenyl-2-phthalimidoacetamido)-N-phenylacetamide, but using 5.1 g of 2-(N-phenyl-2-phthalimidoacetamido)acetic acid, 2.1 g of oxalyl dichloride and 4.8 g of 3,4-dihydro-1,4-2H-benzoxazine as the starting material. The crude product obtained is purified by chromatography on 80 g of silica (0.065–0.200 mm) contained in a column 3.2 cm in diameter [eluent: methylene chloride/ethyl acetate (90-10 by volume)], collecting 20 cm³ fractions. Fractions 17 to 24 are combined and concentrated to dryness under reduced pressure (2.7 kPa) at 40° C. After recrystallization from an ethyl acetate/isopropyl ether mixture (50-50 by volume), 3.9 g of N-[2-(3,4-dihydro-1,4-2H-benzoxazin-4-yl)-2-oxoethyl]-N-phenyl-2-phthalimidoacetamide melting at 173° C are obtained.

3,4-Dihydro-1,4-2H-benzoxazine may be prepared by the method described by Shirai Hideaki et al., C. A., 78, 25378z.

EXAMPLE 59

The procedure is analogous to that described in Example 1, but 1.7 g of 2-amino-N-[2-(4-ethyl-4-methylpiperidino)-2-oxoethyl]-N-phenylacetamide and 0.7 g of 3-methylphenyl isocyanate are used as the starting material. After recrystallization from ethyl acetate, 0.5 g of N-[2-(4-ethyl-4-methylpiperidino)-2-oxoethyl]-2-[3-(3-methylphenyl)ureido]-N-phenylacetamide melting at 204° C is obtained.

2-Amino-N-[2-(4-ethyl-4-methylpiperidino)-2-oxoethyl]-N-phenylacetamide may be prepared in a manner analogous to that described in Example 1 for the preparation of 2-(2-amino-N-phenylacetamido)-N-phenylacetamide, but using 2.7 g of N-[2-(4-ethyl-4-methylpiperidino)-2-oxoethyl]-N-phenyl-2-phthalimidoacetamide and 0.6 g of hydrazine hydrate as the starting material. 1.7 g of 2-amino-N-[2-(4-ethyl-4-methylpiperidino)-2-oxoethyl]-N-phenylacetamide are thus obtained in the form of an oil which is used as such in the subsequent syntheses.

N-[2-(4-Ethyl-4-methylpiperidino)-2-oxoethyl]-N-phenyl-2-phthalimidoacetamide may be prepared in a manner analogous to that described in Example 1 for the preparation of 2-(N-phenyl-2-phthalimidoacetamido)-N-phenylacetamide, but using 5.0 g of 2-(N-phenyl-2-phthalimidoacetamido)acetic acid, 2.3 g of oxalyl dichloride and 3.8 g of 4-ethyl-4-methylpiperidine as the starting material. After recrystallization from a cyclohexane/ethyl acetate mixture (50-50 by volume), 2.8 g of N-[2-(4-ethyl-4-methylpiperidino)-2-oxoethyl]-N-phenyl-2-phthalimidoacetamide melting at 166° C are obtained.

4-Ethyl-4-methylpiperidine may be prepared by the method described by J. M. McManus et al., J. Med. Chem., 774 (1965).

EXAMPLE 60

The procedure is analogous to that described in Example 1, but 1.0 g of 2-amino-N-[2-(4,4-dimethylpiperidino)-2-oxoethyl]-N-phenylacetamide and 0.44 g of 3-methylphenyl isocyanate are used as the starting material. After recrystallization from an ethyl acetate/acetonitrile mixture (50-50 by volume), 0.7 g of N-[2-(4,4-dimethylpiperidino)-2-oxoethyl]-2-[3-(3-methylphenyl)ureido]-N-phenylacetamide melting at 205° C is obtained.

2-Amino-N-[2-(4,4-dimethylpiperidino)-2-oxoethyl]-N-phenylacetamide may be prepared in a manner analogous to that described in Example 1 for the preparation of 2-(2-amino-N-phenylacetamido)-N-phenylacetamide, but using 6.2 g of N-[2-(4,4-dimethylpiperidino)-2-oxoethyl]-N-phenyl-2-phthalimidoacetamide and 1.45 g of hydrazine hydrate as the starting material. 2.6 g of 2-amino-N-[2-(4,4-dimethylpiperidino)-2-oxoethyl]-N-phenylacetamide are thus obtained in the form of an oil which is used as such in the subsequent syntheses.

N-[2-(4,4-Dimethylpiperidino)-2-oxoethyl]-N-phenyl-2-phthalimidoacetamide may be prepared in a manner analogous to that described in Example 1 for the preparation of 2-(N-phenyl-2-phthalimidoacetamido)-N-phenylacetamide, but using 9.0 g of 2-(N-phenyl-2-phthalimidoacetamido)acetic acid, 3.8 g of oxalyl dichloride and 6.0 g of 4,4-dimethylpiperidine as the starting material. After recrystallization from ethyl acetate, 4.25 g of N-[2-(4,4-dimethylpiperidino)-2-oxoethyl]-N-phenyl-2-phthalimidoacetamide melting at 131° C are thus obtained.

4,4-Dimethylpiperidine may be prepared by the method described by J. M. McManus et al., J. Med. Chem., 774 (1965).

EXAMPLE 61

The procedure is analogous to that described in Example 1, but 2.6 g of 2-amino-N-[2-(3,5-dimethylpiperidino)-2-oxoethyl]-N-phenylacetamide, as a mixture of the cis and trans isomers, and 1.06 g of 3-methylphenyl isocyanate are used as the starting material. The crude product obtained is purified by chromatography on 50 g of silica (0.065–0.200 mm) contained in a column 2.5 cm in diameter [eluent: methylene chloride/methanol (99-1 by volume)], collecting 20 cm³ fractions. Fractions 27 to 36 are combined and concentrated to dryness under reduced pressure (2.7 kPa) at 40° C. After recrystallization from ethanol, 1.4 g of N-[2-(3,5-dimethylpiperidino)-2-oxoethyl]-2-[3-(3-methylphenyl)ureido]-N-phenylacetamide are obtained as a mixture of the cis and trans isomers melting at 210° C.

2-Amino-N-[2-(3,5-dimethylpiperidino)-2-oxoethyl]-N-phenylacetamide, as a mixture of the cis and trans isomers, may be prepared in a manner analogous to that described in Example 1 for the preparation of 2-(2-amino-N-phenylacetamido)-N-phenylacetamide, but using 6.8 g of N-[2-(3,5-dimethylpiperidino)-2-oxoethyl]-N-phenyl-2-phthalimidoacetamide and 1.56 g of hydrazine hydrate as the starting material. 2.6 g of 2-amino-N-[2-(3,5-dimethylpiperidino)-2-oxoethyl]-N-phenylacetamide are thus obtained as a mixture of the cis and trans isomers in the form of an oil which is used as such in the subsequent syntheses.

N-[2-(3,5-Dimethylpiperidino)-2-oxoethyl]-N-phenyl-2-phthalimidoacetamide, as a mixture of the cis and trans isomers, may be prepared in a manner analogous to that described in Example 1 for the preparation of 2-( N-phenyl-2-phthalimidoacetamido)-N-phenylacetamide, but using 10 g of 2-(N-phenyl-2-phthalimidoacetamido)acetic acid, 3.74 g of oxalyl dichloride and 6.6 g of 3,5-dimethylpiperidine (mixture of the cis and trans isomers) as the starting material. The crude product obtained is purified by chromatography on 80 g of silica (0.065–0.200 mm) contained in a column 3.5 cm in diameter [eluent: methylene chloride/methanol (99-1 by volume)], collecting 20 cm³ fractions. Fractions 4 to 28 are combined and concentrated to dryness under reduced pressure (2.7 kPa) at 40° C. 6.8 g of N-[2-(3,5-dimethylpiperidino)-2-oxoethyl]-N-phenyl-2-phthalimidoacetamide are thus obtained as a mixture of the cis and trans isomers in the form of a meringue which is used as such in the subsequent syntheses.

EXAMPLE 62

The procedure is analogous to that described in Example 1, but 2.0 g of 2-amino-N-[2-(5-ethyl-2-methylpiperidino)-2-oxoethyl]-N-phenylacetamide, as a mixture of the cis and trans isomers, and 0.8 g of 3-methylphenyl isocyanate are used as the starting material. The crude product obtained is purified by chromatography on 50 g of silica (0.065–0.200 mm) contained in a column 1.5 cm in diameter [eluent: methylene chloride/methanol (98-2 by volume)], collecting 20 cm³ fractions. Fractions 2 to 8 are combined and concentrated to dryness under reduced pressure (2.7 kPa) at 40° C. After recrystallization from an ethyl acetate/diethyl ether mixture (40-60 by volume), 0.5 g of N-[2-(5-ethyl-2-methylpiperidino)-2-oxoethyl]-2-[3-(3-methylphenyl)ureido]-N-phenylacetamide is obtained as a mixture of the cis and trans isomers melting at 158° C.

2-Amino-N-[2-(5-ethyl-2-methylpiperidino)-2-oxoethyl]-N-phenylacetamide, as a mixture of the cis and trans isomers, may be prepared in a manner analogous to that described in Example 1 for the preparation of 2-amino-2-(N-phenylacetamido)-N-phenylacetamide, but using 2.7 g of N-[2-(5-ethyl-2-methylpiperidino)-2-oxoethyl]-N-phenyl-2-phthalimidoacetamide, as a mixture of the cis and trans isomers, and 0.6 g of hydrazine hydrate as the starting material. 2.0 g of 2-amino-N-[2-(5-ethyl-2-methylpiperidino)-2-oxoethyl]-N-phenylacetamide are thus obtained as a mixture of the cis and trans isomers in the form of an oil which is used as such in the subsequent syntheses.

N-[2-(5-Ethyl-2-methylpiperidino)-2oxoethyl]-N-phenyl-2-phthalimidoacetamide, as a mixture of the cis and trans isomers, may be prepared in a manner analogous to that described in Example 1 for the preparation of 2-(N-phenyl-2-phthalimidoacetamido)-N-phenylacetamide, but using 5.0 g of 2-(N-phenyl-2-phthalimidoacetamido)acetic acid, 2.3 g of oxalyl dichloride and 3.8 g of 5-ethyl-2-methylpiperidine (mixture of the cis and trans isomers) as the starting material. The crude product obtained is purified by chromatography on 80 g of silica (0.065–0.200 mm) contained in a column 2.5 cm in diameter [eluent: methylene chloride/methanol (98-2 by volume)], collecting 30 cm³ fractions. Fractions 8 to 18 are combined and concentrated to dryness under reduced pressure (2.7 kPa) at 40° C. 2.7 g of N-[2-(5-ethyl-2-methylpiperidino)-2-oxoethyl]-N-phenyl-2-phthalimidoacetamide are thus obtained as a mixture of the cis and trans isomers in the form of a meringue which is used as such in the subsequent syntheses.

EXAMPLE 63

The procedure is analogous to that described in Example 1, but 1.9 g of 2-(2-amino-N-phenyl-acetamido-N-(2-chlorophenyl)-N-methylacetamide and 0.76 g of 3-methylphenyl isocyanate are used as the starting material. The product obtained is purified by chromatography on 100 g of silica (0.065–0.200 mm) contained in a column 3.2 cm in diameter [eluent: ethyl acetate/cyclohexane (50-50 by volume)], collecting 25 cm³ fractions. Fractions 7 to 15 are combined and concentrated to dryness under reduced pressure (2.7 kPa) at 40° C. After recrystallization from a diethyl ether/ethyl acetate mixture (75-25 by volume), 1.0 g of N-(2-chlorophenyl)-N-methyl-2-{2-[3-(3-methylphenyl)ureido]-N-phenylacetamido}acetamide melting at 175° C is obtained.

2-(2-Amino-N-phenylacetamido)-N-(2-chlorophenyl)-N-methylacetamide may be prepared in a manner analogous to that described in Example 1 for the preparation of 2-(2-amino-N-phenylacetamido)-N-phenylacetamide, but using 2.6 g of N-(2-chlorophenyl)-N-methyl-2-(N-phenyl-2-phthalimidoacetamido)acetamide and 0.6 g of hydrazine hydrate as the staring material. 1.9 g of 2-(2-amino-N-phenylacetamido)-N-(2-chlorophenyl)-N-methylacetamide are thus obtained in the form of an oil which is used as such in the subsequent syntheses.

N-(2-Chlorophenyl)-N-methyl-2-(N-phenyl-2-phthalimidoacetamido)acetamide may be prepared in a manner analogous to that described in Example 1 for the preparation of 2-(N-phenyl-2-phthalimidoacetamido)-N-phenylacetamide, but using 4.15 g of 2-(N-phenyl-2-phthalimidoacetamido)acetic acid, 1.9 g of oxalyl dichloride and 3.5 g of 2-chloro-N-methylaniline as the starting material. The crude product obtained is purified by chromatography on 60 g of silica (0.065–0.200 mm) contained in a column 2.2 cm in diameter [eluent: ethyl acetate/cyclohexane (50-50 by volume)] collecting 25 cm³ fractions. Fractions 6 to 10 are combined and concentrated to dryness under reduced pressure (2.7 kPa) at 40° C. After recrystallization from diisopropyl ether, 2.6 g of N-(2-chlorophenyl)-N-methyl-2-(N-phenyl-2-phthalimidoacetamido)acetamide melting at 175° C are obtained.

2-Chloro-N-methylaniline may be prepared by the method described by R. Stoermer, Chem. Ber., 31, 2531 (1898 [sic]).

EXAMPLE 64

The procedure is analogous to that described in Example 1, but 10.0 g of 2-(2-amino-N-phenyl-acetamido)-N-(3-chlorophenyl)-N-methylacetamide and 3.9 g of 3-methylphenyl isocyanate are used as the starting material. The crude product obtained is purified by chromatography on 150 g of silica (0.065–0.200 mm) contained in a column 3.5 cm in diameter [eluent: dichloromethane/methanol (99-1 by volume)], collecting 50 cm³ fractions. Fractions 5 to 18 are combined and concentrated to dryness under reduced pressure (2.7 kPa) at 40° C. After recrystallization from an ethyl acetate/diethyl ether mixture (60-40 by volume), 5.5 g of N-(3-chlorophenyl)-N-methyl-2-{2-[3-(3-methylphenyl)ureido]-N-phenylacetamido}acetamide melting at 196° C are obtained.

2-(2-Amino-N-phenylacetamido)-N-(3-chlorophenyl)-N-methylacetamide may be prepared in a manner analogous to that described in Example 1 for the preparation of 2-(2-amino-N-phenylacetamido)-N-phenylacetamide, but using 15.6 g of N-(3-chlorophenyl)-N-methyl-2-(N-phenyl-2-phthalimidoacetamido)acetamide and 3.3 g of hydrazine hydrate as the starting material. 10.0 g of 2-(2-amino-N-phenylacetamido)-N-(3-chlorophenyl)-N-methylacetamide are thus obtained in the form of an oil which is used as such in the subsequent syntheses.

N-(3-Chlorophenyl)-N-methyl-2-(N-phenyl-2-phthalimidoacetamido)acetamide may be prepared in a manner analogous to that described in Example 1 for the preparation of 2-(N-phenyl-2-phthalimidoacetamido)-N-phenylacetamide, but using 16.7 g of 2-(N-phenyl-2-phthalimidoacetamido acetic acid, 6.7 g of oxalyl dichloride and 14.0 g of 3-chloro-N-methylaniline as the starting material. After recrystallization from an ethyl acetate/diethyl ether mixture (70-30 by volume), 15.6 g of N-(3-chlorophenyl)-N-methyl-2-(N-phenyl-2-phthalimidoacetamido)acetamide melting at 218° C are obtained.

3-Chloro-N-methylaniline may be prepared by the method described by R. Stoermer, Chem. Ber., 31, 2531 (1898 [sic]).

EXAMPLE 65

The procedure is analogous to that described in Example 1, but 5.3 g of 2-(2-amino-N-phenylacetamido)-N-(2-fluorophenyl)-N-methylacetamide and 2.3 g of 3-methylphenyl isocyanate are used as the starting material. The crude product obtained is purified by chromatography on 140 g of silica (0.065–0.200 mm) contained in a column 3.5 cm in diameter [eluent: dichloromethane/methanol (99-1 by volume)], collecting 30 cm³ fractions. Fractions 8 to 48 are combined and concentrated to dryness under reduced pressure (2.7 kPa) at 40° C. After recrystallization from ethyl acetate, 1.8 g of N-(2-fluorophenyl)-N-methyl-2-{2-[3-(3-methylphenyl)ureido]-N-phenylacetamido}acetamide melting at 172° C are obtained.

2-(2-Amino-N-phenylacetamido)-N-(2-fluorophenyl)-N-methylacetamide may be prepared in a manner analogous to that described in Example 1 for the preparation of 2-(2-amino-N-phenylacetamido)-N-phenylacetamide, but using 8.4 g of N-(2-fluorophenyl)-N-methyl-2-(N-phenyl-2-phthalimidoacetamido)acetamide and 2.0 g of hydrazine hydrate as the staring material. 5.3 g of 2-(2-amino-N-phenylacetamido)-N-(2-fluorophenyl)-N-methylacetamide are thus obtained in the form of an oil which is used as such in the subsequent syntheses.

N-(2-Fluorophenyl)-N-methyl-2-(N-phenyl-2-phthalimidoacetamido)acetamide may be prepared in a manner analogous to that described in Example 1 for the preparation of 2-(N-phenyl-2-phthalimidoacetamido)-N-phenylacetamide, but using 9.4 g of 2-(N-phenyl-2-phthalimidoacetamido)acetic acid, 4.3 g of oxalyl dichloride and 7.2 g of 2-fluoro-N-methylaniline as the starting material. After recrystallization from an ethyl acetate/cyclohexane mixture (50-50 by volume), 8.4 g of N-(2-fluorophenyl)-N-methyl-2-(N-phenyl-2-phthalimidoacetamido)acetamide melting at 184° C are obtained.

2-Fluoro-N-methylaniline may be prepared in the following way: a solution of 12.2 g of 2-fluoroformanilide in 100 cm³ of anhydrous tetrahydrofuran is added in the course of 15 minutes to a suspension of 4.9 g of lithium aluminium hydride in 100 cm³ of anhydrous tetrahydrofuran kept at a temperature close to 25° C. The mixture is stirred at a temperature close to 25° C for 3 hours. After cooling to a temperature close to 5° C, 5.7 cm³ of water, 4.2 cm³ of a 5N aqueous sodium hydroxide solution and then 19 cm³ of water are added successively. The suspension obtained is stirred for 30 minutes and 150 cm³ of diethyl ether are added thereto. The insoluble product is separated off by filtration and the filtrate is concentrated to dryness under reduced pressure (2.7 kPa) at 40° C. The residue is dissolved in 60 cm³ of dichloromethane and the organic phase is dried over magnesium sulphate and then concentrated to dryness under reduced pressure (2.7 kPa) at 40° C. 7.2 g of 2-fluoro-N-methylaniline are thus obtained in the form of an oil which is used as such in the subsequent syntheses.

2-Fluoroformanilide may be prepared in the following way: 11 g of 2-fluoroaniline are added to a solution of 10.8 g of sodium methylate in 100 cm³ of anhydrous dimethylformamide. The mixture is heated under reflux for 2 hours, distilling the methanol formed, and then concentrated to dryness under reduced pressure (0.1 kPa) at 60° C. The residue is taken up in 1 liter of water and 300 cm³ of diethyl ether. The organic phase is separated off, dried over magnesium sulphate and concentrated to dryness under reduced pressure (2.7 kPa) at 30° C. 12.2 g of 2-fluoroformanilide are thus obtained in the form of an oil which is used as such in the subsequent syntheses.

EXAMPLE 66

The procedure is analogous to that described in Example 1, but 2.6 g of 2-(2-amino-N-phenylacetamido)-

N-(4-fluorophenyl)-N-methylacetamide and 1.1 g of 3-methylphenyl isocyanate are used as the starting material. The crude product obtained is purified by chromatography on 60 g of silica (0.065–0.200 mm) contained in a column 2.0 cm in diameter [eluent: ethyl acetate/cyclohexane (50-50 by volume)], collecting 30 cm³ fractions. Fractions 6 to 10 are combined and concentrated to dryness under reduced pressure (2.7 kPa) at 40° C. After recrystallization from ethyl acetate, 1.8 g of N-(4-fluorophenyl)-N-methyl-2-{2-[3-(3-methylphenyl)ureido]-N-phenylacetamido}acetamide melting at 135° C is obtained.

2-(2-Amino-N-phenylacetamido)-N-(4-fluorophenyl)-N-methylacetamide may be prepared in a manner analogous to that described in Example 1 for the preparation of 2-(2-amino-N-phenylacetamido)-N-phenylacetamide, but using 4.5 g of N-(4-fluorophenyl)-N-methyl-2-(N-phenyl-2-phthalimidoacetamido)acetamide and 1.1 g of hydrazine hydrate as the starting material. 2.6 g of 2-(2-amino-N-phenylacetamido)-N-(4-fluorophenyl)-N-methylacetamide are thus obtained in the form of an oil which is used as such in the subsequent syntheses.

N-(4-Fluorophenyl)-N-methyl-2-(N-phenyl-2-phthalimidoacetamido)acetamide may be prepared in a manner analogous to that described in Example 1 for the preparation of 2-(N-phenyl-2-phthalimidoacetamido)-N-phenylacetamide, but using 5.0 g of 2-(N-phenyl-2-phthalimidoacetamido)acetic acid, 2.3 g of oxalyl dichloride and 3.75 g of 4-fluoro-N-methylaniline as the starting material. After recrystallization from an ethyl acetate/cyclohexane mixture (50-50 by volume), 4.5 g of N-(4-fluorophenyl)-N-methyl-2-(N-phenyl-2-phthalimidoacetamido)acetamide melting at 195° C are obtained.

4-Fluoro-N-methylaniline may be prepared in a manner analogous to that described in Example 65 for the preparation of 2-fluoro-N-methylaniline, but using 23.5 g of 4-fluoroformanilide and 14 g of lithium aluminium hydride as the starting material. 21 g of 4-fluoro-N-methylaniline are thus obtained in the form of an oil which is used as such in the subsequent syntheses.

4-Fluoroformanilide may be prepared in a manner analogous to that described in Example 65 for the preparation of 2-fluoroformanilide but using 33 g of 4-fluoroaniline, 33.6 g of sodium methylate and 250 cm³ of dimethylformamide as the starting material. 23.5 g of 4-fluoroformanilide melting at 60° C are thus obtained.

EXAMPLE 67

The procedure is analogous to that described in Example 1, but 9.0 g of 2-(2-amino-N-phenylacetamido)-N-(3-fluorophenyl)-N-methylacetamide and 3.8 g of 3-methylphenyl isocyanate are used as the starting material. The crude product obtained is purified by chromatography on 200 g of silica (0.065–0.200 mm) contained in a column 3.5 cm in diameter [eluent: dichloromethane/methanol (99-1 by volume)], collecting 40 cm³ fractions. Fractions 26 to 46 are combined and concentrated to dryness under reduced pressure (2.7 kPa) at 40° C. After recrystallization from acetonitrile, 3.7 g of N-(3-fluorophenyl)-N-methyl-2-{2-[3-(3-methylphenyl)ureido]-N-phenylacetamido}acetamide melting at 180° C are obtained.

2-(2-Amino-N-phenylacetamido)-N-(3-fluorophenyl)-N-methylacetamide may be prepared in a manner analogous to that described in Example 1 for the preparation of 2-(2-amino-N-phenylacetamido)-N-phenylacetamide, but using 14.7 g of N-(3-fluorophenyl)-N-methyl-2-(N-phenyl-2-phthalimidoacetamido)acetamide and 3.5 g of hydrazine hydrate as the starting material. 9.0 g of 2-(2-amino-N-phenylacetammido)-N-(3-fluorophenyl)-N-methylacetamide are thus obtained in the form of an oil which is used as such in the subsequent syntheses.

N-(3-Fluorophenyl)-N-methyl-2-(N-phenyl-2-phthalimidoacetamido)acetamide may be prepared in a manner analogous to that described in Example 1 for the preparation of 2-(N-phenyl-2-phthalimidoacetamido)-N-phenylacetamide, but using 12.0 g of 2-(N-phenyl-2-phthalimidoacetamido)acetic acid, 5.4 g of oxalyl dichloride and 9.1 g of 3-fluoro-N-methylaniline as the starting material. After recrystallization from an ethyl acetate/cyclohexane mixture (50-50 by volume), 14.7 g of N-(3-fluorophenyl)-N-methyl-2-(N-phenyl-2-phthalimidoacetamido)acetamide melting at 188° C are obtained.

3-Fluoro-N-methylaniline may be prepared in a manner analogous to that described in Example 65 for the preparation of 2-fluoro-N-methylaniline, but using 12.6 g of 3-fluoroformanilide and 5.2 g of lithium aluminium hydride as the starting material. 9.1 g of 3-fluoro-N-methylaniline are thus obtained in the form of an oil which is used as such in the subsequent syntheses.

3-Fluoroformanilide may be prepared in a manner analogous to that described in Example 65 for the preparation of 2-fluoroformanilide, but using 11 g of 3-fluoroaniline, 10.8 g of sodium methylate and 100 cm³ of dimethylformamide as the starting material. 12.6 g of 3-fluoroformanilide are thus obtained in the form of an oil which is used as such in the subsequent syntheses.

EXAMPLE 68

The procedure is analogous to that described in Example 1, but 3.8 g of 2-(2-amino-N-phenylacetamido)-N-(3,4-difluorophenyl)-N-methylacetamide and 1.4 g of 3-methylphenyl isocyanate are used as the starting material. The crude product obtained is purified by chromatography on 80 g of silica (0.065–0.200 mm) contained in a column 2.5 cm in diameter [eluent: ethyl acetate/cyclohexane (75-25 by volume)], collecting 20 cm³ fractions. Fractions 3 to 8 are combined and concentrated to dryness under reduced pressure (2.7 kPa) at 40° C. After recrystallization from a cyclohexane/ethyl acetate mixture (50-50 by volume), 0.5 g of N-(3,4-difluorophenyl)-N-methyl-2-{2-[3-(3-methylphenyl)ureido]-N-phenylacetamido}acetamide melting at 163° C is obtained.

2-(2-Amino-N-phenylacetamido)-N-(3,4-difluorophenyl)-N-methylacetamide may be prepared in a manner analogous to that described in Example 1 for the preparation of 2-(2-amino-N-phenylacetamido)-N-phenylacetamide, but using 5.0 g of N-(3,4-difluorophenyl)-N-methyl-2-(N-phenyl-2-phthalimidoacetamido)acetamide and 1.0 g of hydrazine hydrate as the starting material. 3.8 g of 2-(2-amino-N-phenylacetamido)-N-(3,4-difluorophenyl)-N-methylacetamide are thus obtained in the form of an oil which is used as such in the subsequent syntheses.

N-(3,4-Difluorophenyl)-N-methyl-2-(N-phenyl-2-phthalimidoacetamido)acetamide may be prepared in a manner analogous to that described in Example 1 for the preparation of 2-(N-phenyl-2-phthalimidoacetamido)-N-phenylacetamide, but using 13.8 g of 2-(N-phenyl-2-phthalimidoacetamido)acetic acid, 5.9 g of oxalyl dichloride and 11.4 g of 3,4- difluoro-N-methylaniline as the starting material. After recrystallization from acetonitrile, 5.5 g of N-(3,4-difluorophenyl)-N-methyl-2-(N-phenyl-2-phthalimidoacetamido)acetamide melting at 205° C are obtained.

3,4-Difluoro-N-methylaniline may be prepared in a manner analogous to that described in Example 65 for the preparation of 2-fluoro-N-methylaniline, but using 14.2 g of 3,4-difluoroformanilide and 3.8 g of lithium aluminium hydride as the starting material. 11.4 g of 3,4-difluoro-N-methylaniline are thus obtained in the form of a brown oil which is used as such in the subsequent syntheses.

3,4-Difluoroformanilide may be prepared in a manner analogous to that described in Example 65 for the preparation of 2-fluoroformanilide, but using 12.8 g of 3,4-difluoroaniline, 10.8 g of sodium methylate and 100 cm³ of dimethylformamide as the starting material. 14.2 g of 3,4-difluoroformanilide are thus obtained in the form of an oil which is used as such in the subsequent syntheses.

EXAMPLE 69

The procedure is analogous to that described in Example 1, but 3.5 g of 2-(2-amino-N-phenylacetamido)-N-(2,5-difluorophenyl)-N-methylacetamide and 1.3 g of 3-methylphenyl isocyanate are used as the starting material. The crude product obtained is purified by chromatography on 60 g of silica (0.065–0.200 mm) contained in a column 2.5 cm in diameter [eluent: ethyl acetate/cyclohexane (70-30 by volume)], collecting 20 cm³ fractions. Fractions 3 to 13 are combined and concentrated to dryness under reduced pressure (2.7 kPa) at 40° C. After recrystallization from diethyl ether, 2.4 g of N-(2,5-difluorophenyl)-N-methyl-2-{2-[3-(3-methylphenyl)ureido]-N-phenylacetamido}acetamide melting at 118° C. are obtained.

2-(2-Amino-N-phenylacetamido)-N-(2,5-difluorophenyl)-N-methylacetamide may be prepared in a manner analogous to that described in Example 1 for the preparation of 2-(2-amino-N-phenylacetamido)-N-phenylacetamide, but using 5.0 g of N-(2,5-difluorophenyl)-N-methyl-2-(N-phenyl-2-phthalimidoacetamido)acetamide and 1.0 g of hydrazine hydrate as the starting material. 3.5 g of 2-(2-amino-N-phenylacetamido)-N-(2,5-difluorophenyl)-N-methylacetamide are thus obtained in the form of an oil which is used as such in the subsequent syntheses.

N-(2,5-Difluorophenyl)-N-methyl-2-(N-phenyl-2-phthalimidoacetamido)acetamide may be prepared in a manner analogous to that described in Example 1 for the preparation of 2-(N-phenyl-2-phthalimidoacetamido)-N-phenylacetamide, but using 12.8 g of 2-(N-phenyl-2-phthalimidoacetamido)acetic acid, 5.9 g of oxalyl dichloride and 11.0 g of 2,5-difluoro-N-methylaniline as the starting material. After recrystallization from acetonitrile, 7.6 g of N-(2,5-difluorophenyl)-N-methyl-2-(N-phenyl-2-phthalimidoacetamido)acetamide melting at 220° C are obtained.

2,5-Difluoro-N-methylaniline may be prepared in a manner analogous to that described in Example 65 for the preparation of 2-fluoro-N-methylaniline, but using 16.6 g of 2,5-difluoroformanilide and 4.8 g of lithium aluminium hydride as the starting material. 11.0 g of 2,5-difluoro-N-methylaniline are thus obtained in the form of an oil which is used as such in the subsequent syntheses.

2,5-Difluoroformanilide may be prepared in a manner analogous to that described in Example 65 for the preparation of 2-fluoroformanilide, but using 12.8 g of 2,5-difluoroaniline, 10.8 g of sodium methylate and 100 cm³ of dimethylformamide as the starting material. 16.6 g of 2,5-difluoroformanilide are thus obtained in the form of an oil which is used as such in the subsequent syntheses.

EXAMPLE 70

The procedure is analogous to that described in Example 40, but 2.1 g of 2-[3-(3-methylphenyl)ureido]acetic acid, 3.0 g of ethyl (RS)-2-anilino-2-phenylcarbamoylacetate and 0.7 cm³ of thionyl chloride are used as the starting material. The crude product obtained is chromatographed on 60 g of silica (0.063–0.200 mm) contained in a column 2 cm in diameter [eluent: dichloromethane (100 cm³) and then dichloromethane/methanol (99-1 by volume)], collecting 20 cm³ fractions. Fractions 54 to 80 are combined and concentrated to dryness under reduced pressure (2.7 kPa) at 60° C. After recrystallization from 300 cm³ of petroleum ether, 1.9 g of ethyl (RS)-2-{2-[3-(3-methylphenyl)ureido]-N-phenylacetamido}-2-phenylcarbamoylacetate melting at 125° C are obtained.

Ethyl (RS)-2-anilino-2-phenylcarbamoylacetate may be prepared in a manner analogous to that described in Example 42 for the preparation of tert-butyl (RS)-2-anilino-2-[(1-pyrrolidinyl)carbonyl]acetate, but using 5.7 g of ethyl (RS)-2-bromo-2-phenylcarbamoylacetate and 3.7 g of aniline in 40 cm³ of acetonitrile as the starting material. 6.2 g of ethyl (RS)-2-anilino-2-phenylcarbamoylacetate are thus obtained in the form of an oil which is used as such in the subsequent syntheses.

Ethyl (RS)-2-bromo-2-phenylcarbamoylacetate may be prepared in a manner analogous to that described in Example 42 for tert-butyl (RS)-2-bromo-2-[(1-pyrrolidinyl)carbonyl]acetate, but using 10.4 g of ethyl 2-phenylcarbamoylacetate, 5.9 g of acetamide and 2.6 cm³ of bromine in 230 cm³ of chloroform as the starting material. 11.5 g of ethyl (RS)-2-bromo-2-phenylcarbamoylacetate melting at 90° C are thus obtained.

Ethyl 2-phenylcarbamoylacetate may be prepared by the method described by F. D. Coattaway et al., J. Chem. Soc., 97, 939 (1910).

EXAMPLE 71

The procedure is as in Example 40, but 2.5 g of 2-[3-(3-methylphenyl)ureido]acetic acid, 4.2 g of tert-butyl (RS)-2-anilino-2-[(3,3-dimethyl-1-piperidino)carbonyl]acetate and 0.87 g of thionyl chloride are used as the starting material. The crude product obtained is chromatographed on 130 g of silica (0.063–0.208 mm) in a column 2.4 cm in diameter [eluents: dichloromethane (1000 cm³) and then dichloromethane/methanol (99-1 by volume)], collecting 20 cm³ fractions. Fractions 55 to 99 are combined and concentrated to dryness under reduced pressure (2.7 kPa) at 60° C. After recrystallization from 30 cm³ of petroleum ether, 0.5 g of tert-butyl (RS)-2-[(3,3-dimethyl-1-piperidino)carbonyl]-2-{2-[3-(3-methylphenyl)ureido]-N-phenylacetamido}acetate melting at 130° C is obtained.

tert-Butyl (RS)-2-anilino-2-[(3,3-dimethyl-1-piperidino)carbonyl]acetate may be prepared in the following way: 2.2 g of aniline are added to a solution of 8.0 g of tert-butyl (RS)-2-bromo-2-[(3,3-dimethyl-1-piperidino)carbonyl]acetate in 3.4 cm³ of triethylamine and the reaction mixture is heated at 90° C for 5 hours and then at a temperature close to 20° C for 20 hours.

The solid mass is treated with 250 cm³ of diethyl ether and the insoluble product is separated off by filtration and washed with twice 100 cm³ of diethyl ether. The filtrate is concentrated to dryness under reduced pressure (2.7 kPa) at 50° C. 6.0 g of tert-butyl (RS)-2-anilino-2-[(3,3-dimethyl-1-piperidino)carbonyl]acetate melting at 70° C are thus obtained.

tert-Butyl (RS)-2-bromo-2-[(3,3-dimethyl-1-piperidino)carbamoyl]acetate may be prepared in a manner analogous to that described in Example 42 for tert-butyl (RS)-2-bromo-2-[(1-pyrrolidinyl)carbonyl]acetate, but using 10.2 g of tert-butyl 2-[(3,3-dimethyl-1-piperidino)carbonyl]acetate, 4.7 g of acetamide and 2.05 cm³ of bromine in 150 cm³ of chloroform as the starting material. 10.8 g of tert-butyl (RS)-2-bromo-2-[(3,3-dimethyl-1-piperidino)carbonyl]acetate are thus obtained in the form of an oil which is used as such in the subsequent syntheses.

tert-Butyl 2-[(3,3-dimethyl-1-piperidino)carbonyl]acetate may be prepared in the following way: 16.2 g of N,N'-diimidazolecarbonyl are added in portions to a solution of 16 g of tert-butyl hydrogen malonate in 450 cm³ of anhydrous tetrahydrofuran. The reaction mixture is stirred at a temperature close to 20° C for 4 hours and 11.7 cm³ of 3,3-dimethylpiperidine are then added. The reaction mixture is further stirred for 20 hours at a temperature close to 20° C and then diluted with 1 liter of water and extracted with three times 200 cm³ of methylene chloride. The organic phases are combined, washed with twice 100 cm³ of water, dried over magnesium sulphate and concentrated to dryness under reduced pressure (2.7 kPa) at 60° C. 22.0 g of tert-butyl 2-[(3,3-dimethyl-1-piperidino)carbonyl]acetate are thus obtained in the form of an oil which is used as such in the subsequent syntheses.

EXAMPLE 72

6.6 g of ethyl 3-aminobenzoate are added to a solution of 7.8 g of 2-{2-[(1-imidazolyl)carboxamido]-N-phenylacetamido}-N-methyl-N-phenylacetamide in 100 cm³ of toluene. The mixture is stirred under reflux for 2 hours and then concentrated to dryness under reduced pressure (2.7 kPa) at 45° C. The residue is dissolved in 200 cm³ of ethyl acetate and the solution obtained is washed with 50 cm³ of a 2N aqueous hydrochloric acid solution and then with twice 50 cm³ of water. The organic phase is dried over magnesium sulphate and concentrated to dryness under reduced pressure (2.7 kPa) at 40° C. The crude product obtained is purified by chromatography on 100 g of silica (0.065–0.200 mm) contained in a column 2.5 cm in diameter [eluent: ethyl acetate], collecting 20 cm³ fractions. Fractions 4 to 11 are combined and concentrated to dryness under reduced pressure (2.7 kPa) at 40° C. After recrystallization from ethyl acetate, 3.8 g of ethyl 3-{3-[N-(N-methyl-N-phenylcarbamoylmethyl)-N-phenylcarbamoylmethyl]ureido}benzoate melting at 174° C are obtained.

EXAMPLE 73

The procedure is analogous to that described in Example 72, but 1.3 g of 2-{2-[(1-imidazolyl)carboxamido]-N-phenylacetamido}-N-methyl-N-phenylacetamide and 0.78 g of 3-aminobenzonitrile are used as the starting material. The crude product obtained is purified by chromatography on 25 g of silica (0.065–0.200 mm) contained in a column 1.8 cm in diameter [eluent: dichloromethane/ethyl acetate (50-50 by volume)], collecting 25 cm³ fractions. Fractions 7 to 17 are combined and concentrated to dryness under reduced pressure (2.7 kPa) at 40° C. After recrystallization from acetonitrile, 0.7 g of 2-{2-[3-(3-cyanophenyl)ureido]-N-phenylacetamido}-N-methyl-N-phenylacetamide melting at 204° C is obtained.

EXAMPLE 74

5 cm³ of an N aqueous sodium hydroxide solution are added to a solution of 2.4 g of ethyl 3-{3-[N-(N-methyl-N-phenylcarbamoylmethyl)-N-phenylcarbamoylmethyl]ureido}benzoate in 90 cm³ of a water/tetrahydrofuran/dioxane mixture (30/40/30 by volume). The mixture is stirred for 16 hours at a temperature close to 25° C and then concentrated to about 50 cm³ under reduced pressure (2.7 kPa) at 40° C. The solution obtained is diluted with 50 cm³ of water, washed with twice 50 cm³ of ethyl acetate, acidified to pH 3 with a 4N aqueous hydrochloric acid solution and extracted with twice 30 cm³ of ethyl acetate. The organic phases are combined, washed with 30 cm³ of water, dried over magnesium sulphate and concentrated to dryness under reduced pressure (2.7 kPa) at 30° C. After recrystallization from ethyl acetate, 1.4 g of 3-{3-[N-(N-methyl-N-phenylcarbamoylmethyl)-N-phenylcarbamoylmethyl]ureido}benzoic acid melting at 232° C are obtained.

EXAMPLE 75

The procedure is analogous to that described in Example 72, but 3 g of 2-{2-[(1-imidazolyl)carboxamido]-N-phenylacetamido}-N-methyl-N-phenylacetamide and 3.3 g of 3-aminobenzophenone are used as the starting material. After recrystallization from dichloromethane, 1.3 g of 2-{2-[3-(3-benzoylphenyl)ureido]-N-phenylacetamido}-N-methyl-N-phenylacetamide melting at 215° C are obtained.

3-Aminobenzophenone may be prepared by the method described by G. J. Esselen, Jr. and L. Clarke, J. Amer. Chem. Soc., 36, 322 (1914).

EXAMPLE 76

0.3 g of sodium borohydride is added in the course of 1 hour to a suspension of 2 g of 2-{2-[3-(3-benzoylphenyl)ureido]-N-phenylacetamido}-N-methyl-N-phenylacetamide in a methanol/tetrahydrofuran/water mixture (70/28/2 by volume). The mixture is stirred for 30 minutes at a temperature close to 25° C and then concentrated to dryness under reduced pressure (2.7 kPa) at 35° C. The residue is dissolved in 50 cm³ of dichloromethane and the solution obtained is washed with 30 cm³ of a 2N aqueous hydrochloric acid solution and then with 30 cm³ of water. The organic phase is dried over magnesium sulphate and then concentrated to dryness under reduced pressure (2.7 kPa) at 35° C. After recrystallization from an ethyl acetate/diethyl ether mixture (60/40 by volume), 1.4 g of (RS)-2-{2-[3-(3-α-hydroxybenzylphenyl)ureido]-N-phenylacetamido}-N-methyl-N-phenylacetamide melting at 160° C are obtained.

EXAMPLE 77

The procedure is analogous to that described in Example 72, but 3.5 g of 2-{2-[(1-imidazolyl)carboxamido]-N-phenylacetamido}-N-methyl-N-phenylacetamide and 2.5 g of 3-nitroaniline are used as the starting material. The crude product obtained is purified by chromatography on 60 g of silica (0.065–0.200 mm) contained in a column 2.2 cm in diameter [eluent: dichloromethane/ethyl acetate (80-20 by volume)], collecting 20 cm³ fractions. Fractions 12 to 20 are combined and concentrated to dryness under reduced pressure (2.7 kPa) at 40° C. After recrystallization from an ethyl acetate/acetonitrile mixture (90/10 by volume), 1.1 g of N-methyl-2-{2-[3-(3-nitrophenyl)-ureido]-N-phenylacetamido}-N-phenylacetamide melting at 152° C are obtained.

EXAMPLE 78

The procedure is analogous to that described in Example 72, but 2.95 g of 2-{2-[(1-imidazolyl)carboxamido]-N-phenylacetamido}-N-methyl-N-phenylacetamide and 2.64 g of 1-(3-aminophenyl)-piperidine are used as the starting material. The crude product obtained is purified by chromatography on 35 g of silica (0.065–0.200 mm) contained in a column 1.5 cm in diameter [eluent: dichloromethane/ethyl acetate (50/50 by volume)], collecting 25 cm³ fractions. Fractions 20 to 26 are combined and concentrated to dryness under reduced pressure (2.7 kPa) at 40° C. After recrystallization from an acetonitrile/dimethylformamide mixture (90/10 by volume), 0.75 g of N-methyl-N-phenyl-2-{2-[3-(3-piperidinophenyl)ureido]-N-phenylacetamido}acetamide melting at 235° C is obtained.

1-(3-Aminophenyl)piperidine may be prepared by the method described by G. Adriant and C. Glacet, Bull. Soc. Chim. Fr., 1511 (1970).

EXAMPLE 79

The procedure is analogous to that described in Example 72, but 2.9 g of 2-{2-[(1-imidazolyl)carboxamido]-N-phenylacetamido}-N-methyl-N-phenylacetamide and 2.6 g of 3-aminobenzenesulphonamide are used as the starting material. The crude product obtained is purified by chromatography on 45 g of silica (0.065–0.200 mm) contained in a column 1.5 cm in diameter [eluent: ethyl acetate), collecting 25 cm³ fractions. Fractions 3 to 7 are combined and concentrated to dryness under reduced pressure (2.7 kPa) at 40° C. After recrystallization from an acetonitrile/ethyl acetate mixture (70/30 by volume), 0.9 g of N-methyl-N-phenyl-2-{2-[3-(3-sulphamoylphenyl)ureido]-N-phenylacetamido}acetamide melting at 175° C is obtained.

3-Aminobenzenesulphonamide may be prepared by the method described by W. A. Jacobs and M. Heidelberger, J. Am. Chem. Soc., 39, 2428 (1917).

EXAMPLE 80

The procedure is analogous to that described in Example 72, but 1.96 g of 2-{2-[(1-imidazolyl)carboxamido]-N-phenylacetamido}-N-methyl-N-phenylacetamide and 1.36 g of 3-aminobenzamide are used as the starting material. After recrystallization from an acetonitrile/ethyl acetate mixture (55/45 by volume), 1.25 g of 3-{3-[N-(N-methyl-N-phenylcarbamoylmethyl)-N-phenylcarbamoylmethyl]ureido}benzamide melting at 170° C are obtained.

3-Aminobenzamide may be prepared by the method described by W. A. Jacobs and M. Heidelberger, J. Am. Chem. Soc, 39, 1438 (1917).

EXAMPLE 81

1.64 g of 4-nitrophenyl isocyanate are added at a temperature close to 25° C to a solution of 3.0 g of 2-(2-amino-N-phenylacetamido)-N-methyl-N-phenylacetamide in 50 cm³ of anhydrous tetrahydrofuran. The mixture is stirred for 12 hours at a temperature close to 25° C and the insoluble product is separated off by filtration. After recrystallization from ethyl acetate, 3.2 g of N-methyl-2-{2-[3-(4-nitrophenyl)ureido]-N-phenylacetamido}-N-phenylacetamide melting at 215° C are obtained.

EXAMPLE 82

0.3 g of 5% palladium-on-charcoal is added to a solution of 1.8 g of N-methyl-2-{2-[3-(3-nitrophenyl)ureido]-N-phenylacetamido}-N-phenylacetamide in 100 cm³ of ethanol. The suspension obtained is stirred for 2 hours at a temperature close to 50° C under a hydrogen atmosphere (100 kPa). After cooling, the catalyst is separated off by filtration and the solution is concentrated to dryness under reduced pressure (2.7 kPa) at 35° C. The residue obtained is dissolved in 60 cm³ of an acetonitrile/diisopropyl ether mixture (20/80 by volume) and 5 cm³ of a 3.5N solution of hydrochloric acid in diisopropyl ether are added. The insoluble product formed is separated off by filtration, air-dried and recrystallization from ethanol. 0.9 g of 2-{2-[3-(3-aminophenyl)ureido]-N-phenylacetamido}-N-methyl-N-phenylacetamide hydrochloride melting at 220° C is thus obtained.

EXAMPLE 83

The procedure is analogous to that described in Example 72, but 1.28 g of 2-{2-[(1-imidazolyl)carboxamido]-N-phenylacetamido}-N-methyl-N-phenylacetamide and 1.05 g of 5-aminosalicylic acid are used as the starting material. The crude product obtained is purified by chromatography on 40 g of silica (0.065–0.200 mm) contained in a column 3 cm in diameter [eluent: tetrahydrofuran/water (99/1 by volume)], collecting 25 cm³ fractions. Fractions 2 to 4 are combined and concentrated to dryness under reduced pressure (2.7 kPa) at 40° C. After recrystallization from a water/acetonitrile mixture (55/45 by volume), 0.18 g of 5-{3-[N-(N-methyl-N-phenylcarbamoylmethyl)-N-phenylcarbamoylmethyl]ureido}salicylic acid melting at 189° C is obtained.

EXAMPLE 84

2.3 g of manganese dioxide are added in 2 portions at a 20-hour interval to a solution of 0.8 g of (RS)-2-{3-[3-(1-hydroxyethyl)phenyl]ureido}-N-[2-oxo-2-(1,2,3,4-tetrahydro-1-quinolyl)ethyl]-N-phenylacetamide in 50 cm³ of methylene chloride. The mixture is stirred at a temperature close to 25° C for 70 hours. The insoluble product is separated off by filtration and the filtrate is concentrated to dryness under reduced pressure (2.7 kPa) at 40° C. After recrystallization from diisopropyl ether, 0.3 g of 2-[3-(3-acetylphenyl)ureido]-N-[2-oxo-2-(1,2,3,4-tetrahydro-1-quinolyl)ethyl]-N-phenylacetamide melting at 130° C is obtained.

EXAMPLE 85

The procedure is analogous to that described in Example 84, but 1.4 g of (RS)-2-{2-{3-[3-(1-hydroxyethyl)phenyl]ureido}-N-phenylacetamido}-N-methyl-N-phenylacetamide and 4.7 g of manganese dioxide are used as the starting material. After recrystallization from ethyl acetate, 0.65 g of 2-{2-[3-(3-acetylphenyl)ureido]-N-phenylacetamido}-N-methyl-N-phenylacetamide melting at 170° C is obtained.

EXAMPLE 86

2 cm³ of distilled water and 0.17 g of hydroxylamine hydrochloride are added to a solution of 1.1 g of 2-{2-[3-(3-acetylphenyl)ureido]-N-phenylacetamido}-N-methyl-N-phenylacetamide in 10 cm³ of ethanol. The mixture is stirred under reflux for 3 hours. After cooling, the insoluble product is separated off by filtration, washed with 3 times 10 cm³ of water and air-dried. After recrystallization from methanol, 0.45 g of (E)-2-{2-{3-[3-(1-hydroxyiminoethyl)phenyl]ureido}-N-phenylacetamido}-N-methyl-N-phenylacetamide melting at 170° C is obtained.

EXAMPLE 87

1.5 g of m-chloroperbenzoic acid in solution in 10 cm³ of methylene chloride is run, in the course of 10 minutes, into a solution of 1.1 g of 2-[3-(3-methylthiophenyl)ureido]-N-[2-oxo-2-(1,2,3,4-tetrahydro-1-quinolyl)ethyl]-N-phenylacetamide in 10 cm³ of methylene chloride kept at a temperature close to 0° C. The mixture is stirred for 2 hours at a temperature close to 25° C and then diluted with 25 cm³ of methylene chloride. The solution is washed with 20 cm³ of a saturated aqueous sodium thiosulphate solution, 20 cm³ of a saturated aqueous sodium bicarbonate solution and then 20 cm³ of a saturated aqueous sodium chloride solution. The organic phase is dried over magnesium sulphate and concentrated to dryness under reduced pressure (2.7 kPa) at 40° C. The crude product obtained is purified by chromatography on 40 g of silica (0,062-0,200 mm) contained in a column 1.2 cm in diameter [eluent: ethyl acetate/methanol (95/5 by volume)], collecting 10 cm³ fractions. Fractions 6 to 13 are combined and concentrated to dryness under reduced pressure (2.7 kPa) at 40° C. After recrystallization from a diisopropyl ether/ethyl acetate mixture (90/10 by volume), 0.5 g of (RS)-2-[3-(3-methylsulphinylphenyl)ureido]-N-[2-oxo-2-(1,2,3,4-tetrahydro-1-quinolyl)ethyl]-N-phenylacetamide melting at 140° C is obtained.

EXAMPLE 88

0.16 g of 0-methylhydroxylamine hydrochloride in solution in 2 cm³ of water is added to a solution of 0.92 g of 2-{2-[3-(3-acetylphenyl)ureido]-N-phenylacetamido}-N-methyl-N-phenylacetamide in 10 cm³ of ethanol. The mixture is stirred under reflux for 3 hours and then at a temperature close to 25° C for 12 hours and concentrated to a volume of about 3 cm³ under reduced pressure (2.7 kPa) at 40° C. 20 cm³ of distilled water are then added and the insoluble product is separated off by filtration and air-dried. After recrystallization from a methanol/diisopropyl ether mixture (60/40 by volume), 0.31 g of (Z)-2-{2-{3-[3-(1-methoxyiminoethyl)phenyl]ureido}-N-phenylacetamido}-N-methyl-N-phenylacetamide melting at 165° C is obtained.

EXAMPLE 89

0.18 g of pyridine and then 0.17 g of hydroxylamine hydrochloride in solution in 3 cm³ of water are added to a solution of 1 g of 2-{2-[3-(3-formylphenyl)ureido]-N-phenylacetamido}-N-methyl-N-phenylacetamide in 6 cm³ of methanol. The mixture is heated under reflux for 3 hours. After cooling, the insoluble product is separated off by filtration, washed with 3 times 3 cm³ of water and air-dried. After recrystallization from a dimethylformamide/water mixture (50/50 by volume), 0.5 g of (E)-2-{2-[3-(3-hydroxyiminomethylphenyl)ureido]-N-phenylacetamido}-N-methyl-N-phenylacetamide melting at 219° C is obtained.

2-{2-[3-(3-Formylphenyl)ureido]-N-phenylacetamido}-N-methyl-N-phenylacetamide may be prepared in a manner analogous to that described in Example 84 for the preparation of 2-[3-(3-acetylphenyl)ureido]-N-[2-oxo-2-(1,2,3,4-tetrahydro-1-quinolyl)ethyl]-N-phenylacetamide, but using 1.3 g of 2-{2-[3-(3-hydroxymethylphenyl)ureido]-N-phenylacetamido}-N-methyl-N-phenylacetamide and 2.7 g of manganese dioxide as the starting material. The crude product obtained is purified by chromatography on 25 g of silica (0.065-0.200 mm) contained in a column 1.8 cm in diameter (eluent: ethyl acetate), collecting 25 cm³ fractions. Fractions 3 to 7 are combined and concentrated to dryness under reduced pressure (2.7 kPa) at 40° C. 1.1 g of 2-{2-[3-(3-formylphenyl)ureido]-N-phenylacetamido}-N-methyl-N-phenylacetamide are thus obtained in the form of a meringue which is used as such in the subsequent syntheses.

EXAMPLE 90

0.30 g of triethylamine and then 0.24 g of acetyl chloride are added to a solution of 1.38 g of (RS)-2-{2-{3-[3-(1-hydroethyl)phenyl]ureido}-N-phenylacetamido}-N-methyl-N-phenylacetamide in 30 cm³ of methylene chloride kept at a temperature close to 5° C. The mixture is stirred at a temperature close to 5° C for 1 hour and then at a temperature close to 25° C for 12 hours. The solution obtained is washed with twice 10 cm³ of water. The organic phase is dried over magnesium sulphate and concentrated to dryness under reduced pressure (2.7 kPa) at 40° C. The crude product obtained is purified by chromatography on 60 g of silica (0.065-0.200 mm) contained in a column 2.5 cm in diameter [eluent: methylene chloride/ethyl acetate (50/50 by volume)], collecting 25 cm³ fractions. Fractions 6 to 11 are combined and concentrated to dryness under reduced pressure (2.7 kPa) at 40° C. After recrystallization from an ethyl acetate/diethyl ether mixture (70/30 by volume), 0.32 g of (RS)-1-{3-{3-[N-(N-methyl-N-phenylcarbamoylmethyl)-N-phenylcarbamoylmethyl]ureido}phenyl}ethanol melting at 168° C is obtained.

EXAMPLE 91

The procedure is analogous to that described in Example 72, but 1.96 g of 2-{2-[(1-imidazolyl)carboxamido]-N-phenylacetamido}-N-methyl-N-phenylacetamide and 1.5 g of (RS)-3-(1-methoxyethyl)aniline are used as the starting material. After recrystallization from acetonitrile, 0.71 g of (RS)-2-{2-{3-[3-(1-methoxyethyl)phenyl]ureido}-N-phenylacetamido}-N-methyl-N-phenylacetamide melting at 194° C is obtained.

(RS)-3-(1-Methoxyethyl)aniline may be prepared in the following way: 7 g of an oily suspension (50% by weight) of sodium hydride are added in the course of 5 minutes to a solution of 20 g of (RS)-3-(1-hydroxyethyl)aniline in 300 cm³ of anhydrous dimethylformamide kept at a temperature close to 10° C. The mixture is stirred for 30 minutes at a temperature close to 10° C and 20.7 g of methyl iodide are then added thereto in the course of 10 minutes. The mixture is then stirred at a temperature close to 40° C for 2 hours, cooled and then poured into 500 cm³ of water. The aqueous phase is extracted with 3 times 250 cm³ of ethyl acetate and the combined organic phases are then washed with twice 200 cm³ of water, dried over magnesium sulphate and concentrated to dryness under reduced pressure (2.7 kPa) at 40° C. The crude residue obtained is purified by chromatography on 300 g of silica (0.065–0.200 mm) contained in a column 4.2 cm in diameter [eluent: methylene chloride/ethyl acetate (50/50 by volume)], collecting 50 cm³ fractions. Fractions 7 to 12 are combined and concentrated to dryness under reduced pressure (2.7 kPa) at 40° C. 5 g of (RS)-3-(1-methoxyethyl)aniline are thus obtained in the form of an oil which is used as such in the subsequent syntheses.

EXAMPLE 92

The procedure is analogous to that described in Example 72, but 4.0 g of N-[2-(3,3-dimethylpiperidino)-2-oxoethyl]-2-[(1-imidazolyl)carboxamido]-N-phenylacetamide and 3.3 g of ethyl 3-aminobenzoate are used as the starting material. The crude product is purified by chromatography on 50 g of silica (0.065–0.200 mm) contained in a column 2.0 cm in diameter [eluent: methylene chloride/ethyl acetate (40/60 by volume)], collecting 20 cm³ fractions. Fractions 5 to 13 are combined and concentrated to dryness under reduced pressure (2.7 kPa) at 40° C. After recrystallization from an ethyl acetate/diisopropyl ether mixture (60/40 by volume), 2.6 g of ethyl 3-{3-{N-[2-(3,3-dimethylpiperidino)-2-oxoethyl]-N-phenylcarbamoylmethyl}ureido}benzoate melting at 164° C are obtained.

EXAMPLE 93

The procedure is analogous to that described in Example 74, but 2.0 g of ethyl 3-{3-{N-[2-(3,3-dimethylpiperidino)-2-oxoethyl]-N-phenylcarbamoylmethyl}ureido}benzoate and 4 cm³ of a 1N aqueous sodium hydroxide solution are used as the starting material. After recrystallization from an ethyl acetate/dimethylformamide mixture (90/10 by volume), 1.1 g of 3-{3-{N-[2-(3,3-dimethylpiperidino)-2-oxoethyl]-N-phenylcarbamoylmethyl}ureido}benzoic acid melting at 270° C are obtained.

EXAMPLE 94

The procedure is analogous to that described in Example 74, but 1.5 g of ethyl 3-{3-[N-(N-methyl-N-phenylcarbamoylmethyl)-N-phenylcarbamoylmethyl]ureido}phenylacetate and 3 cm³ of a 1N aqueous sodium hydroxide solution are used as the starting material. After recrystallization from ethyl acetate, 0.9 g of 3-{3-[N-(N-methyl-N-phenylcarbamoylmethyl)-N-phenylcarbamoylmethyl]ureido}phenylacetic acid melting at 228° C is obtained.

Ethyl 3-{3-[N-(N-methyl-N-phenylcarbamoylmethyl)-N-phenylcarbamoylmethyl]ureido}phenylacetate may be prepared in a manner analogous to that described in Example 72 for the preparation of ethyl 3-{3-[N-(N-methyl-N-phenylcarbamoylmethyl)-N-phenylcarbamoylmethyl]ureido}benzoate, but using 1.75 g of 2-{2-[(1-imidazolyl)carboxamido]-N-phenylacetamido}-N-methyl-N-phenylacetamide and 1.6 g of ethyl 3-aminophenylacetate as the starting material. The crude product obtained is purified by chromatography on 30 g of silica (0.065–0.200 mm) contained in a column 1.8 cm in diameter [eluent: dichloromethane/ethyl acetate (50/50 by volume)], collecting 20 cm³ fractions. Fractions 13 to 23 are combined and concentrated to dryness under reduced pressure (2.7 kPa) at 40° C. 1.5 g of ethyl 3-{3-[N-(N-methyl-N-phenylcarbamoylmethyl)-N-phenylcarbamoylmethyl]ureido}phenylacetate are thus obtained in the form of an oil which is used as such in the subsequent syntheses.

Ethyl 3-aminophenylacetate may be prepared in the following way: 0.1 g of 5% palladium-on-charcoal is added to a solution of 2.0 g of ethyl 3-nitrophenylacetate in 20 cm³ of ethanol. The suspension is stirred for 2 hours at a temperature close to 25° C under a hydrogen atmosphere (100 kPa). The catalyst is then separated off by filtration and the filtrate is concentrated to dryness under reduced pressure (2.7 kPa) at 40° C. 1.7 g of ethyl 3-aminophenylacetate are thus obtained in the form of an oil which is used as such in the subsequent syntheses.

Ethyl 3-nitrophenylacetate may be prepared by the method described by Segers and A. Bruylants, Bul. Soc. Chim. Belg., 64, 87 (1955).

EXAMPLE 95

2.5 g of trifluoroacetic acid are added to a suspension of 1.5 g of tert-butyl 3-{3-[N-(N-methyl-N-phenylcarbamoylmethyl)-N-phenylcarbamoylmethyl]ureido}phenoxyacetate in 20 cm³ of 1,2-dichloroethane and the mixture is heated under reflux for 1 hour and then left at a temperature close to 25° C for 12 hours and concentrated to dryness under reduced pressure (2.7 kPa) at 40° C. The residue obtained is purified by chromatography on 40 g of silica (0.065–0.200 mm) contained in a column 3 cm in diameter [eluent: methylene chloride/methanol (80-20 by volume)], collecting 20 cm³ fractions. Fractions 6 to 17 are combined and concentrated to dryness under reduced pressure (2.7 kPa) at 40° C. After dissolving the solid obtained in 10 cm³ of a 4N aqueous sodium hydroxide solution and filtering the solution obtained, 10 cm³ of a 4N aqueous hydrochloric acid solution are added. The insoluble product is separated off by filtration, washed with 5 times 5 cm³ of water and air-dried. 0.55 g of 3-{3-[N-(N-methyl-N-phenylcarbamoylmethyl)-N-phenylcarbamoylmethyl]ureido}phenoxyacetic acid melting at 130° C is thus obtained.

tert-Butyl 3-{3-[N-(N-methyl-N-phenylcarbamoylmethyl)-N-phenylcarbamoylmethyl]ureido}phenoxyacetate may be prepared in a manner analogous to that described in Example 72 for the preparation of ethyl 3-{3-[N-(N-methyl-N-phenylcarbamoylmethyl)-N-phenylcarbamoylmethyl]ureido}benzoate, but using 3.5 g of 2-{2-[(1-imidazolyl)carboxamido]-N-phenylacetamido}-N-methyl-N-phenylacetamide and 4 g of tert-butyl 3-aminophenoxyacetate as the starting material. The crude product obtained is purified by chromatography on 90 g of silica (0.065–0.200 mm) contained in a column 2.5 cm in diameter [eluent: methylene chloride/ethyl acetate (80/20 by volume)], collecting 25 cm³ fractions. Fractions 15 to 29 are combined and concentrated to dryness under reduced pressure (2.7 kPa) at 40° C. After recrystallization from isopropanol, 1.3 g of tert-butyl 3-{3-[N-(N-methyl-N-phenylcarbamoylmethyl)-N-phenylcarbamoylmethyl]ureido}phenoxyacetate melting at 174° C are obtained.

tert-Butyl 3-aminophenoxyacetate may be prepared in the following way: 0.2 g of 5% palladium-on-charcoal is added to a solution of 5.4 g of tert-butyl 3-nitrophenoxyacetate in 50 cm³ of ethanol. The suspension is stirred for 2 hours at a temperature close to 25° C under a hydrogen atmosphere (100 kPa). The catalyst is then separated off by filtration and the filtrate is concentrated to dryness under reduced pressure (2.7 kPa) at 40° C. 4.8 g of tert-butyl 3-aminophenoxyacetate are thus obtained in the form of an oil which is used as such in the subsequent syntheses.

tert-Butyl 3-nitrophenoxyacetate may be prepared in the following way: 1.44 g of an oily suspension (50% by weight) of sodium hydride are added in the course of 10 minutes to a solution of 4.17 g of 3-nitrophenol in 50 cm³ of anhydrous dimethylformamide. The mixture obtained is stirred at a temperature close to 25° C for 30 minutes and 5.85 g of tert-butyl bromoacetate are then added in the course of 10 minutes. The mixture is stirred for 2 hours at a temperature close to 25° C and then poured into 150 cm³ of water and extracted with twice 50 cm³ of ethyl acetate. The combined organic phases are dried over magnesium sulphate and concentrated to dryness under reduced pressure (2.7 kPa) at 35° C. After recrystallization from cyclohexane, 5.4 g of tert-butyl 3-nitrophenoxyacetate melting at 52° C are obtained.

EXAMPLE 96

The procedure is analogous to that described in Example 74, but 0.8 g of ethyl 3-{3-{N-[2-oxo-2-(1,2,3,4-tetrahydro-1-quinolyl)ethyl]-N-phenylcarbamoylmethyl}ureido}benzoate and 1.55 cm³ of a 1N aqueous sodium hydroxide solution are used as the starting material. The crude product obtained is dissolved in 10 cm³ of a 1N aqueous sodium hydroxide solution. The solution is washed with 10 cm³ of ethyl acetate and then acidified to pH 1 with 11 cm³ of a 1N aqueous hydrochloric acid solution. The insoluble product is separated off by filtration, washed with 3 times 2 cm³ of water and air-dried. 0.35 g of 3-{3-{N-[2-oxo-2-(1,2,3,4-tetrahydro-1-quinolyl)ethyl]-N-phenylcarbamoylmethyl}ureido}benzoic acid melting at 280° C is thus obtained.

EXAMPLE 97

The procedure is analogous to that described in Example 72, but 3 g of 2-[(1-imidazolyl)carboxamido]-N-[2-oxo-2-(1,2,3,4-tetrahydro-1-quinolyl)ethyl]-N-phenylacetamide and 2.4 g of ethyl 3-aminobenzoate are used as the starting material. The crude product obtained is purified by chromatography on 80 g of silica (0.065–0.200 mm) contained in a column 2.5 cm in diameter [eluent: methylene chloride/ethyl acetate (40/60 by volume)], collecting 25 cm³ fractions. Fractions 8 to 16 are combined and concentrated to dryness under reduced pressure (2.7 kPa) at 40° C. After recrystallization from an ethyl acetate/diisopropyl ether mixture (70/30 by volume), 1.2 g of ethyl 3-{3-{N-[2-oxo-2-(1,2,3,4-tetrahydro-1-quinolyl)ethyl]-N-phenylcarbamoylmethyl}ureido}benzoate melting at 174° C are obtained.

EXAMPLE 98

The procedure is analogous to that described in Example 72, but 1.74 g of N-[2-(3,3-dimethylpiperidino)-2-oxoethyl]-2-[(1-imidazolyl)carboxamido]-N-phenylacetamide and 1 g of 3-(1-hydroxyiminoethyl)aniline are used as the starting material. The crude product obtained is purified by chromatography on 50 g of silica (0.065–0.200 mm) contained in a column 2.2 cm in diameter [eluent: ethyl acetate], collecting 20 cm³ fractions. Fractions 6 to 13 are combined and concentrated to dryness under reduced pressure (2.7 kPa) at 40° C. After recrystallization from acetonitrile, 0.3 g of (E)-N-[2-(3,3-dimethylpiperidino)-2-oxoethyl]-2-{3-[3-(1-hydroxyiminoethyl)phenyl]ureido}-N-phenylacetamide melting at 248° C is obtained.

3-(1-Hydroxyiminoethyl)aniline may be prepared in the following way: 3.16 g of pyridine and then 3.06 g of hydroxylamine hydrochloride in solution in 10 cm³ of water are added to a solution of 5.4 g of 3-aminoacetophenone in 20 cm³ of methanol. The mixture is heated under reflux for 5 hours, cooled to a temperature close to 20° C and poured into 20 cm³ of water. The solution obtained is brought to pH 8 using a 1N aqueous sodium hydroxide solution. The insoluble product is separated off by filtration, washed with 5 times 20 cm³ of water and air-dried. 4.2 g of 3-(1-hydroxyiminoethyl)aniline melting at 133° C are thus obtained.

EXAMPLE 99

The procedure is analogous to that described in Example 74, but 2.2 g of methyl (RS)-3-{3-[N-(N-methyl-N-phenylcarbamoylmethyl)-N-phenylcarbamoylmethyl]ureido}mandelate and 4.35 cm³ of a 1N aqueous sodium hydroxide solution are used as the starting material. After recrystallization from a water/dimethylformamide mixture (63/35 by volume), 1.6 g of (RS)-3-{3-[N-(N-methyl-N-phenylcarbamoylmethyl)-N-phenylcarbamoylmethyl]ureido}mandelic acid melting at 246° C are obtained.

Methyl (RS)-3-{3-[N-(N-methyl-N-phenylcarbamoylmethyl)-N-phenylcarbamoylmethyl]ureido}mandelate may be prepared in a manner analogous to that described in Example 72 for the preparation of ethyl 3-{3-[N-(N-methyl-N-phenylcarbamoylmethyl)-N-phenylcarbamoylmethyl]ureido}benzoate, but using 3.5 g of 2-{2-[(1-imidazolyl)carboxamido]-N-phenylacetamido}-N-methyl-N-phenylacetamide and 3.24 g of methyl (RS)-3-aminomandelate as the starting material. The crude product obtained is purified by chromatography on 70 g of silica (0.065–0.200 mm) contained in a column 3 cm in diameter [eluent: methylene chloride/ethyl acetate (50/50 by volume)], collecting 30 cm³ fractions. Fractions 18 to 29 are combined and concentrated to dryness under reduced pressure (2.7 kPa) at 40° C. 2.5 g of methyl (RS)-3-{3-[N-(N-methyl-N-phenylcarbamoylmethyl)-N-phenylcarbamoylmethyl]ureido}mandelate are thus obtained in the form of a meringue which is used as such in the subsequent syntheses.

Methyl (RS)-3-aminomandelate may be prepared in the following way: 0.5 g of 5% palladium-on-charcoal is added to a solution of 15 g of methyl (RS)-3-nitromandelate in 150 cm³ of ethanol. The suspension is stirred for 2 hours at a temperature close to 25° C under a hydrogen atmosphere (100 kPa). The catalyst is then separated off by filtration and the filtrate is concentrated to dryness under reduced pressure (2.7 kPa) at 40° C. 13.1 g of methyl (RS)-3-aminomandelate are thus obtained in the form of an oil which is used as such in the subsequent syntheses.

Methyl (RS)-3-nitromandelate may be prepared by the method described by L. S. Fosdick and J. C. Calandra, J. Am. Chem. Soc., 63, 1101 (1941).

EXAMPLE 100

The procedure is analogous to that described in Example 74, but 3 g of ethyl 3-{3-{3-[N-(N-methyl-N-phenylcarbamoylmethyl)-N-phenylcarbamoylmethyl]ureido}phenyl}propionate and 5.8 cm³ of a 1N aqueous sodium hydroxide solution are used as the starting material. After recrystallization from an ethyl acetate/dimethylformamide mixture (90/10 by volume), 0.9 g of 3-{3-{3-[N-(N-methyl-N-phenylcarbamoylmethyl)-N- phenylcarbamoylmethyl]ureido}phenyl}propionic acid melting at 208° C is obtained.

Ethyl 3-{3-{3-[N-(N-methyl-N-phenylcarbamoylmethyl)-N-phenylcarbamoylmethyl]ureido}phenyl}propionate may be prepared in a manner analogous to that described in Example 72 for the preparation of ethyl 3-{3-[N-(N-methyl-N-phenylcarbamoylmethyl)-N-phenylcarbamoylmethyl]ureido}benzoate, but using 3.13 g of 2-{2-[(1-imidazolyl)carboxamido]-N-phenylacetamido}-N-methyl-N-phenylacetamide and 3.0 g of ethyl 3-(3-aminophenyl)propionate as the starting material. The crude product is purified by chromatography on 50 g of silica (0.065–0.200 mm) contained in a column 2 cm in diameter (eluent: ethyl acetate), collecting 20 cm³ fractions. Fractions 4 to 7 are combined and concentrated to dryness under reduced pressure (2.7 kPa) at 40° C. 3 g of ethyl 3-{3-{3-[N-(N-methyl-N-phenylcarbamoylmethyl)-N-phenylcarbamoylmethyl]ureido}phenyl}propionate are thus obtained in the form of an oil which is used as such in the subsequent syntheses.

Ethyl 3-(3-aminophenyl)propionate may be prepared in a manner analogous to that described in Example 99 for the preparation of methyl (RS)-3-aminomandelate, but using 6.6 g of ethyl (E)-3-nitrocinnamate and 0.2 g of 5% palladium-on-charcoal as the starting material. 7.5 g of ethyl 3-(3-aminophenyl)propionate are thus obtained in the form of an oil which is used as such in the subsequent syntheses.

Ethyl (E)-3-nitrocinnamate may be prepared in the following way: 5 cm³ of pure sulphuric acid are added to a solution of 31 g of (E)-3-nitrocinnamic acid in 300 cm³ of ethanol. The mixture is stirred under reflux for 3 hours. After cooling and adding 50 cm³ of water, the solution is concentrated to about 60 cm³ under reduced pressure (2.7 kPa) at 40° C. 250 cm³ of ethyl acetate are added and the organic phase is then washed with twice 100 cm³ of a 2N aqueous sodium hydroxide solution and twice 100 cm³ of water, dried over magnesium sulphate and concentrated to dryness under reduced pressure (2.7 kPa) at 40° C. 32 g of ethyl (E)-3-nitrocinnamate melting at 70° C are thus obtained.

(E)-3-Nitrocinnamic acid may be prepared in the following way: a mixture of 30.2 g of 3-nitrobenzaldehyde, 20.8 g of malonic acid, 15.8 g of pyridine and 5 drops of piperidine is heated under reflux for 1 hour. After cooling, 50 cm³ of water are added and the insoluble product is separated off by filtration, washed with 3 times 50 cm³ of water and air-dried. 31 g of (E)-3-nitrocinnamic acid melting at 205° C are thus obtained.

EXAMPLE 101

The procedure is analogous to that described in Example 74, but 1.0 g of ethyl (E)-3-{3-[N-(N-methyl-N-phenylcarbamoylmethyl)-N-phenylcarbamoylmethyl]ureido}cinnamate and 2 cm³ of a 1N aqueous sodium hydroxide solution are used as the starting material. After recrystallization from ethyl acetate, 0.4 g of (E)-3-{3-[N-(N-methyl-N-phenylcarbamoylmethyl)-N-phenylcarbamoylmethyl]ureido}cinnamic acid melting at 210° C is obtained.

Ethyl (E)-3-{3-[N-(N-methyl-N-phenylcarbamoylmethyl)-N-phenylcarbamoylmethyl]ureido}cinnamate may be prepared in a manner analogous to that described in Example 72 for the preparation of ethyl 3-{3-[N-(N-methyl-N-phenylcarbamoylmethyl)-N-phenylcarbamoylmethyl]ureido}benzoate, but using 3.6 g of 2-{2-[(1-imidazolyl)carboxamido]-N-phenylacetamido}-N-methyl-N-phenylacetamide and 3.5 g of ethyl (E)-3-aminocinnamate as the starting material. The crude product is purified by chromatography on 50 g of silica (0.065–0.200 mm) contained in a column 2 cm in diameter (eluent: ethyl acetate), collecting 20 cm³ fractions. Fractions 5 to 17 are combined and concentrated to dryness under reduced pressure (2.7 kPa) at 40° C. 2.9 g of ethyl (E)-3-{3-[N-(N-methyl-N-phenylcarbamoylmethyl)-N-phenylcarbamoylmethyl]ureido}cinnamate are thus obtained in the form of a meringue which is used as such in the subsequent syntheses.

Ethyl (E)-3-aminocinnamate may be prepared by the method described by Bayer A. G., Netherlands Patent Application 74 16 449 (C. A. 84, 58 882q).

EXAMPLE 102

The procedure is analogous to that described in Example 72, but 3.1 g of 2-{2-[(1-imidazolyl)carboxamido]-N-phenylacetamido}-N-methyl-N-phenylacetamide and 7 g of tetra-n-butylammonium 3-aminobenzenesulphonate are used as the starting material. The crude product obtained is dissolved in 6 cm³ of acetone and a solution of 0.9 g of potassium nonafluorobutanesulphonate in 4 cm³ of acetone is added. The insoluble product is separated off by filtration, washed with twice 3 cm³ of acetone and 4 times 3 cm³ of diisopropyl ether and then purified by chromatography on 30 g of silica (0.065–0.200 mm) contained in a column 2.4 cm in diameter [eluent: tetrahydrofuran/water (92/8 by volume)], collecting 10 cm³ fractions. Fractions 4 to 11 are combined and concentrated to dryness under reduced pressure (2.7 kPa) at 45° C. The residue is stirred for 30 minutes in 6 cm³ of acetone and the insoluble product is separated off by filtration, washed with twice 2 cm³ of acetone and 4 times 2 cm³ of diisopropyl ether and then air-dried. 0.2 g of potassium 3-{3-[N-(N-methyl-N-phenyl-carbamoylmethyl)-N-phenylcarbamoylmethyl]ureido}-benzenesulphonate melting at about 280° C is thus obtained.

Tetra-n-butylammonium 3-aminobenzenesulphonate may be prepared in a manner analogous to that described in Example 99 for the preparation of methyl 3-aminomandelate, but using 13 g of tetra-n-butylammonium 3-nitrobenzenesulphonate and 0.2 g of 5% palladium-on-charcoal as the starting material. 12.4 g of tetra-n-butylammonium 3-aminobenzenesulphonate are thus obtained in the form of an oil which is used as such in the subsequent syntheses.

Tetra-n-butylammonium 3-nitrobenzenesulphonate may be prepared in the following way: 6.6 g of sodium 3-nitrobenzenesulphonate and then 9.8 g of tetra-n-butylammonium hydrogen sulphate are added to 800 cm³ of a 0.5M aqueous potassium dihydrogen phosphate solution. The mixture is extracted with 500 cm³ of methylene chloride. The organic phase is dried over magnesium sulphate and concentrated to dryness under reduced pressure (2.7 kPa) at 40° C. 13 g of tetra-n-butylammonium 3-nitrobenzenesulphonate are thus obtained in the form of an oil which is used as such in the subsequent syntheses.

EXAMPLE 103

The procedure is analogous to that described in Example 72, but 2.35 g of 2-{2-[(1-imidazolyl)carboxamido]-N-phenylacetamido}-N-methyl-N-phenylacetamide and 1.8 g of (RS)-2-(3-aminophenyl)-2-hydroxyethanol are used as the starting material. After recrystallization from ethanol, 1.3 g of (RS)-2-{2-{3-[3-(1,2-dihydroxyethyl)phenyl]ureido}-N-phenylacetamido}-N-methyl-N-phenylacetamide melting at 190° C are obtained.

(RS)-2-(3-Aminophenyl)-2-hydroxyethanol may be prepared in a manner analogous to that described in Example 99 for the preparation of methyl (RS)-3-aminomandelate, but using 2.3 g of (RS)-2-hydroxy-2-(3-nitrophenyl)ethanol and 0.15 g of 5% palladium-on-charcoal as the starting material. 1.8 g of (RS)-2-(3-aminophenyl)-2-hydroxyethanol are thus obtained in the form of an oil which is used as such in the subsequent syntheses.

(RS)-2-Hydroxy-2-(3-nitrophenyl)ethanol may be prepared in the following way: 2.2 g of 2-(3-nitrophenyl)oxirane are added to 90 cm$^3$ of a 2N aqueous sulphuric acid solution. The mixture obtained is stirred at a temperature close to 95° C for 3 hours. After cooling and adding 18 cm$^3$ of a 10N aqueous sodium hydroxide solution, the insoluble oil is extracted with twice 150 cm$^3$ of ethyl acetate. The combined organic phases are washed with 100 cm$^3$ of water, dried over magnesium sulphate and then concentrated to dryness under reduced pressure (2.7 kPa) at 40° C. 2.3 g of (RS)-2-hydroxy-2-(3-nitrophenyl)ethanol melting at 45° C are thus obtained.

2-(3-Nitrophenyl)oxirane may be prepared in the following way: 0.68 g of sodium borohydride is added to a solution of 4.9 g of 3-nitrophenacyl bromide in 100 cm$^3$ of ethanol. The mixture is stirred for 12 hours at a temperature close to 25° C and then poured into 150 cm$^3$ of water. The solution obtained is concentrated to about 150 cm$^3$ under reduced pressure (2.7 kPa) at 40° C and then extracted with 3 times 100 cm$^3$ of ethyl acetate. The combined organic phases are dried over magnesium sulphate and concentrated to dryness under reduced pressure (2.7 kPa) at 40° C. The residue obtained is purified by chromatography on 100 g of silica (0.065-0.200 mm) contained in a column 3.2 cm in diameter (eluent: methylene chloride), collecting 30 cm$^3$ fractions. Fractions 4 to 8 are combined and concentrated to dryness under reduced pressure (2.7 kPa) at 40° C. 2.2 g of 2-(3-nitrophenyl)oxirane are thus obtained in the form of an oil which is used as such in the subsequent syntheses.

EXAMPLE 104

The procedure is analogous to that described in Example 74, but 0.9 g of methyl 3-{3-[N-(N-methyl-N-phenylcarbamoylmethyl)-N-phenylcarbamoylmethyl]ureido}phenylglyoxylate and 1.8 cm$^3$ of a 1N aqueous sodium hydroxide solution are used as the starting material. The crude product is dissolved in 20 cm$^3$ of a 4N aqueous sodium hydroxide solution. The solution obtained is washed with twice 20 cm$^3$ of ethyl acetate and 20 cm$^3$ of a 4N aqueous hydrochloric acid solution are then added. The insoluble product is separated off by filtration, washed with 5 times 5 cm$^3$ of water and air-dried. 0.66 g of 3-{3-[N-(N-methyl-N-phenylcarbamoylmethyl)-N-phenylcarbamoyl]ureido}phenylglyoxylic acid melting at 220° C is thus obtained.

Methyl 3-{3-[N-(N-methyl-N-phenylcarbamoylmethyl)-N-phenylcarbamoylmethyl]ureido}phenylglyoxylate may be prepared in a manner analogous to that described in Example 84 for the preparation of 2-[3-(3-acetylphenyl)ureido]-N-[2-oxo-2-(1,2,3,4-tetrahydro-1-quinolyl)ethyl]-N-phenylacetamide, but using 1.7 g of methyl (RS)-3-{3-[N-(N-methyl-N-phenylcarbamoylmethyl)-N-phenylcarbamoylmethyl]ureido}mandelate and 5.3 g of manganese dioxide as the starting material. The crude product is purified by chromatography on 70 g of silica (0.065-0.200 mm) contained in a column 2.5 cm in diameter [eluent: methylene chloride/ethyl acetate (60/40 by volume)], collecting 25 cm$^3$ fractions. Fractions 25 to 33 are combined and concentrated to dryness under reduced pressure (2.7 kPa) at 40° C. 1.3 g of methyl 3-{3-[N-(N-methyl-N-phenylcarbamoylmethyl)-N-phenylcarbamoylmethyl]ureido}phenylglyoxylate are thus obtained in the form of a meringue which is used as such in the subsequent syntheses.

EXAMPLE 105

The procedure is analogous to that described in Example 81, but 0.6 g of 2-(2-amino-N-phenylacetamido)-N-isopropyl-N-phenylacetamide and 0.24 g of 3-methylphenyl isocyanate are used as the starting material. The crude product obtained is purified by chromatography on 30 g of silica (0.065-0.200 mm) contained in a column 1.5 cm in diameter [eluent: dichloromethane/ethyl acetate (80/20 by volume)], collecting 20 cm$^3$ fractions. Fractions 6 to 10 are combined and concentrated to dryness under reduced pressure (2.7 kPa) at 40° C. After recrystallization from diethyl ether, 0.3 g of N-isopropyl 2-{2-[3-(3-methylphenyl)ureido]-N-phenylacetamido}-N-phenylacetamide melting at 170° C is obtained.

2-(2-Amino-N-phenylacetamido)-N-isopropyl-N-phenylacetamide may be prepared in a manner analogous to that described in Example 72 for the preparation of 2-(2-amino-N-phenylacetamido)-N-methyl-N-phenylacetamide, but using 1.3 g of N-isopropyl-N-phenyl-2-(N-phenyl-2-phthalimidoacetamido)acetamide and 0.28 g of hydrazine hydrate as the starting material. 0.6 g of 2-(2-amino-N-phenylacetamido)-N-isopropyl-N-phenylacetamide is thus obtained in the form of an oil which is used as such in the subsequent syntheses.

N-Isopropyl-N-phenyl-2-(N-phenyl-2-phthalimidoacetamido)acetamide may be prepared in a manner analogous to that described in Example 72 for the preparation of N-methyl-N-phenyl-2-(N-phenyl-2-phthalimidoacetamido)acetamide, but using 3.4 g of 2-(N-phenyl-2-phthalimidoacetamido)acetic acid, 1.4 g of oxalyl dichloride and 3.0 g of N-isopropylaniline as the starting material. After recrystallization from diethyl ether, 1.3 g of N-isopropyl-N-phenyl-2-(N-phenyl-2-phthalimidoacetamido)acetamide melting at 152° C are thus obtained.

N-Isopropylaniline may be prepared by the method described by K. A. Schellenberg, J. Org. Chem., 28, 3259 (1963).

EXAMPLE 106

0.49 g of 3-methylphenyl isocyanate is added at a temperature close to 25° C to a solution of 1.2 g of 2-amino-N-[2-(8-azaspiro[4,5]decan-8-yl)-2-oxoethyl]-N-phenylacetamide in 50 cm$^3$ of anhydrous tetrahydrofuran. The mixture is stirred for 12 hours at a temperature close to 25° C and the insoluble product is separated off by filtration. After recrystallization from ethyl acetate, 0.7 g of N-[2-(8azaspiro[4,5]decan-8-yl)-2-oxoethyl]-2-[3-(3-methylphenyl)ureido]-N-phenylacetamide melting at 183° C. is obtained.

2-Amino-N-[2-(8-azaspiro[4,5]decan-8-yl)-2-oxoethyl]-N-phenylacetamide may be prepared in the following way: 0.43 g of hydrazine hydrate is added to a solution of 2 g of N-[2-(8-azaspiro[4,5]decan-8-yl)-2-oxoethyl]-N-phenyl-2-phthalimidoacetamide in 100 cm³ of methanol. The reaction mixture is heated under reflux for 2 hours. After cooling and adding 25 cm³ of an N aqueous hydrochloric acid solution, the insoluble product is separated off by filtration. The filtrate is concentrated under reduced pressure (2.7 kPa) at 30° C. The residue is dissolved in 75 cm³ of water and the solution is then washed with 40 cm³ of diethyl ether, rendered alkaline using sodium hydroxide solution and extracted with twice 40 cm³ of ethyl acetate. The combined organic phases are dried over magnesium sulphate and then concentrated to dryness under reduced pressure (2.7 kPa) at 30° C. 1.2 g of 2-amino-N-[2-(8-azaspiro[4,5]decan-8-yl)-2-oxoethyl]-N-phenylacetamide are thus obtained in the form of an oil which is used as such in the subsequent syntheses.

N-[2-(8-Azaspiro[4,5]decan-8-yl)-2-oxoethyl]-N-phenyl-2-phthalimidoacetamide may be prepared in the following way: 1.65 g of oxalyl dichloride and then 0.1 cm³ of dimethylformamide are added to a suspension of 4 g of 2-(2-phthalimido-N-phenylacetamido)acetic acid in 40 cm³ of 1,2-dichloroethane. The mixture is stirred for 2 hours at a temperature close to 25° C and 3.3 g of 8-azaspiro[4,5]decane are then added. The solution is stirred for 2 hours at a temperature close to 25° C and then washed with twice 40 cm³ of water, dried over magnesium sulphate and concentrated to dryness under reduced pressure (2.7 kPa) at 40° C. The product obtained is purified by chromatography on 70 g of silica (0.065–0.200 mm) contained in a column 2.5 cm in diameter [eluent: ethyl acetate/cyclohexane (75/25 by volume)], collecting 25 cm³ fractions. Fractions 2 to 5 are combined and concentrated to dryness under reduced pressure (2.7 kPa) at 40° C. After recrystallization from an ethyl acetate/cyclohexane mixture (50/50 by volume), 2.1 g of N-[2-(8-azaspiro[4,5]decan-8-yl)-2-oxoethyl]-N-phenyl-2-phthalimidoacetamide melting at 190° C are obtained.

8-Azaspiro[4,5]decane may be prepared by the method described by J. M. McManus et al., J. Med. Chem., 774 (1965).

EXAMPLE 107

Following a procedure analogous to that described in Example 106, but using 1.8 g of (RS)-2-amino-N-[2-(3-(N,N-diethylcarbamoyl)piperidino)-2-oxoethyl]-N-phenylacetamide and 0.64 g of 3-methylphenyl isocyanate as the starting material, 0.92 g of (RS)-N-[2-(3-(N,N-diethylcarbamoyl)piperidino)-2-oxoethyl]-2-[3-(3-methylphenyl)ureido]-N-phenyl acetamide melting at 156° C is obtained after recrystallization from an ethyl acetate/diisopropyl ether mixture (50/50 by volume).

(RS)-2-Amino-N-[2-(3-(N,N-diethylcarbamoyl)piperidino)-2-oxoethyl]-N-phenylacetamide may be prepared in a manner analogous to that described in Example 106 for the preparation of 2-amino-N-[2-(8-azaspiro[4,5]decan-8-yl)-2-oxoethyl]-N-phenylacetamide, but using 2.9 g of (RS)-N-[2-(3-(N,N-diethylcarbamoyl)piperidino)-2-oxoethyl]-N-phenyl-2-phthalimidoacetamide and 0.57 g of hydrazine hydrate as the starting material. 1.8 g of (RS)-2-amino-N-[2-(3-(N,N-diethylcarbamoyl)piperidino)-2-oxoethyl]-N-phenylacetamide are thus obtained in the form of an oil which is used as such in the subsequent syntheses.

(RS)-N-[2-(3-(N,N-diethylcarbamoyl)piperidino)-2-oxoethyl]-N-phenyl-2-phthalimidoacetamide may be prepared in a manner analogous to that described in Example 106 for the preparation of N-[2-(8-azaspiro[4,5]decan-8-yl)-2-oxoethyl]-N-phenyl-2-phthalimidoacetamide, but using 3.4 g of 2-(N-phenyl-2-phthalimidoacetamido)acetic acid, 1.4 g of oxalyl dichloride and 4.6 g of (RS)-N,N-diethylnipecotamide. 2.9 g of N-[2-(3-(N,N-diethylcarbamoyl)piperidino)-2-oxoethyl]-N-phenyl-2-phthalimidoacetamide are thus obtained in the form of an amorphous powder which is used as such in the subsequent syntheses.

EXAMPLE 108

The procedure is analogous to that described in Example 106, but 2.0 g of 2-amino-N-[2-oxo-2-(1,2,3,4-tetrahydro-2-isoquinolyl)ethyl]-N-phenylacetamide and 0.8 g of 3-methylphenyl isocyanate are used as the starting material. The crude product is purified by chromatography on 70 g of silica (0.065–0.200 mm) contained in a column 2.5 cm in diameter [eluent: methylene chloride/methanol (98-2 by volume)], collecting 20 cm³ fractions. Fractions 12 to 26 are combined and concentrated to dryness under reduced pressure (2.7 kPa) at 40° C. After recrystallization from ethyl acetate, 1.0 g of 2-[3-(3-methylphenyl)ureido]-N-[2-oxo-2-(1,2,3,4-tetrahydro-2-isoquinolyl)ethyl]-N-phenylacetamide melting at 135° C is obtained.

2-Amino-N-[2-oxo-(1,2,3,4-tetrahydro-2-isoquinolyl)ethyl]-N-phenylacetamide may be prepared in a manner analogous to that described in Example 106 for the preparation of 2-amino-N-[2-(8-azaspiro[4,5]decan-8-yl)-2-oxoethyl]-N-phenylacetamide, but using 2.9 g of N-[2-oxo-2-(1,2,3,4-tetrahydro-2-isoquinolyl)ethyl]-N-phenyl-2-phthalimidoacetamide and 0.63 g of hydrazine hydrate as the starting material. 2.0 g of 2-amino-N-[2-oxo-2-(1,2,3,4-tetrahydro-2-isoquinolyl)ethyl]-N-phenylacetamide are thus obtained in the form of an oil which is used as such in the subsequent syntheses.

N-[2-Oxo-2-(1,2,3,4-tetrahydro-2-isoquinolyl)ethyl]-N-phenyl-2-phthalimidoacetamide may be prepared in a manner analogous to that described in Example 106 for the preparation of N-[2-(8-azaspiro[4,5]decan-8-yl)-2-oxoethyl]-N-phenyl-2-phthalimidoacetamide, but using 4.3 g of 2-(N-phenyl-2-phthalimidoacetamido)acetic acid, 1.65 g of oxalyl dichloride and 3.6 g of 1,2,3,4-tetrahydroisoquinoline as the starting material. The crude product obtained is purified by chromatography on 80 g of silica (0.065–0.200 mm) contained in a column 2.5 cm in diameter [eluent: methylene chloride/methanol (98-2 by volume)], collecting 30 cm³ fractions. Fractions 6 to 15 are combined and concentrated to dryness under reduced pressure (2.7 kPa) at 40° C. 2.9 g of N-[2-oxo-2-(1,2,3,4-tetrahydro-2-isoquinolyl)ethyl]-N-phenyl-2-phthalimidoacetamide are thus obtained in the form of an amorphous powder which is used as such in the subsequent syntheses.

EXAMPLE 109

0.86 g of hydrazine hydrate is added to a suspension of 4 g of 2-(N-phenyl-2-phthalimidoacetamido)-N-(8-quinolyl)acetamide in 40 cm³ of methanol. The reaction mixture is heated under reflux for 40 minutes and then concentrated to dryness under reduced pressure (2.7 kPa) at 40° C. The residue is stirred for 30 minutes in 30 cm³ of anhydrous tetrahydrofuran and the insoluble product is separated off by filtration. 0.75 g of 3-methylphenyl isocyanate is then added to the filtrate and the mixture is stirred for 30 minutes at a temperature close to 25° C and then concentrated to dryness under reduced pressure (2.7 kPa) at 40° C. The residue obtained is purified by chromatography on 50 g of silica (0.065–0.200 mm) contained in a column 2.2 cm in diameter [eluent: methylene chloride], collecting 25 cm³ fractions. Fractions 11 to 13 are combined and concentrated to dryness under reduced pressure (2.7 kPa) at 40° C. After recrystallization from an acetonitrile/ethyl acetate mixture (55/45 by volume), 0.4 g of 2-{2-[3-(3-methylphenyl)ureido]-N-phenylacetamido}-N-(8-quinolyl)acetamide melting at 170° C is obtained.

2-(N-Phenyl-2-phthalimidoacetamido)-N-(8-quinolyl)acetamide may be prepared in a manner analogous to that described in Example 106 for the preparation of N-[2-(8-azaspiro[4,5]decan-8-yl)-2-oxoethyl]-N-phenyl-2-phthalimidoacetamide, but using 3.4 g of 2-(N-phenyl-2-phthalimidoacetamido)acetic acid, 1.5 g of oxalyl dichloride and 1.76 g of 8-aminoquinoline as the starting material. 4 g of 2-(N-phenyl-2-phthalimidoacetamido)-N-(8-quinolyl)acetamide are thus obtained in the form of an amorphous powder which is used as such in the subsequent syntheses.

EXAMPLE 110

The procedure is analogous to that described in Example 106, but 5.9 g of ethyl (RS)-1-[2-(2-amino-N-phenylacetamido)acetyl]piperidine-3-carboxylate and 2.26 g of 3-methylphenyl isocyanate are used as the starting material. The crude product obtained is purified by chromatography on 250 g of silica (0.062–0.200 mm) contained in a column 4.2 cm in diameter [eluent: methylene chloride/ethyl acetate (50/50 by volume)], collecting 40 cm³ fractions. Fractions 4 to 10 are combined and concentrated to dryness under reduced pressure (2.7 kPa) at 40° C. After recrystallization from ethyl acetate, 1.4 g of ethyl (RS) 1-{2-{2-[3-(3-methylphenyl)ureido]-N-phenylacetamido}acetyl}-piperidine-3-carboxylate melting at 166° C are obtained.

Ethyl (RS)-1-[2-(2-amino-N-phenylacetamido)acetyl]piperidine-3-carboxylate may be prepared in a manner analogous to that described in Example 106 for the preparation of 2-amino-N-[2-(8-azaspiro[4,5]decan-8-yl)-2-oxoethyl]-N-phenylacetamide, but using 8.1 g of ethyl (RS)-1-[2-(N-phenyl-2-phthalimidoacetamido)acetyl]piperidine-3-carboxylate and 0.85 g of hydrazine hydrate as the starting material. 5.6 g of ethyl (RS)-1-[2-(2-amino-N-phenylacetamido)acetyl]piperidine-3-carboxylate are thus obtained in the form of an oil which is used as such in the subsequent syntheses.

Ethyl (RS)-1-[2-(N-phenyl-2-phthalimidoacetamido)acetyl]piperidine-3-carboxylate may be prepared in a manner analogous to that described in Example 106 for the preparation of N-[2-(8-azaspiro[4,5]decan-8-yl)-2-oxoethyl]-N-phenyl-2-phthalimidoacetamide, but using 6.8 g of 2-(N-phenyl-2-phthalimidoacetamido)acetic acid, 2.8 g of oxalyl dichloride and 7.85 g of ethyl (RS)-nipecotate as the starting material. 9.4 g of ethyl (RS)-1-[2-(N-phenyl-2-phthalimidoacetamido)acetyl]piperidine-3-carboxylate are thus obtained in the form of an amorphous powder which is used as such in the subsequent syntheses.

EXAMPLE 111

Following a procedure analogous to that described in Example 106, but using 1.8 g of 2-amino-N-[2-oxo-2-(1-perhydroquinolyl)ethyl]-N-phenylacetamide and 0.73 g of 3-methylphenyl isocyanate as the starting material, 1.4 g of 2-[3-(3-methylphenyl)ureido]-N-[2-oxo-2-(1-perhydroquinolyl)]-N-phenylacetamide (mixture of the cis and trans isomers) melting at 223° C are obtained after recrystallization from acetonitrile.

2-Amino-N-[2-oxo-2-(1-perhydroquinolyl)ethyl]-N-phenylacetamide may be prepared in a manner analogous to that described in Example 106 for the preparation of 2-amino-N-[2-(8-azaspiro[4,5]decan-8-yl-)-2-oxoethyl]-N-phenylacetamide, but using 2.7 g of N-[2-oxo-2-(1-perhydroquinolyl)ethyl]-N-phenyl-2-phthalimidoacetamide and 0.6 g of hydrazine hydrate as the starting material. 1.8 g of 2-amino-N-[2-oxo-2-(1-perhydroquinolyl)ethyl]-N-phenylacetamide (mixture of the cis and trans isomers) are thus obtained in the form of an oil which is used as such in the subsequent syntheses.

N-[2-Oxo-2-(1-perhydroquinolyl)ethyl]-N-phenyl-2-phthalimidoacetamide may be prepared in a manner analogous to that described in Example 106 for the preparation of N-[2-(8-azaspiro[4,5]decan-8-yl)-2-oxoethyl]-N-phenyl-2-phthalimidoacetamide, but using 3.4 g of 2-(N-phenyl-2-phthalimidoacetamido)acetic acid, 1.4 g of oxalyl dichloride and 4.17 g of perhydroquinoline (mixture of the cis and trans isomers) as the starting material. The crude product obtained is purified by chromatography on 50 g of silica (0.065–0.200 mm) contained in a column 2.0 cm in diameter [eluent: methylene chloride/ethyl acetate (80-20 by volume)], collecting 20 cm³ fractions. Fractions 10 to 17 are combined and concentrated to dryness under reduced pressure (2.7 kPa) at 40° C. 2.7 g of N-[2-oxo-2-(1-perhydroquinolyl)ethyl]-N-phenyl-2-phthalimidoacetamide (mixture of the cis and trans isomers) are thus obtained in the form of an amorphous powder which is used as such in the subsequent syntheses.

EXAMPLE 112

Following a procedure analogous to that described in Example 106, but using 1.8 g of (RS)-2-amino-N-[2-oxo-2-(2-phenyl-1-pyrrolidinyl)ethyl]-N-phenylacetamide and 0.7 g of 3-methylphenyl isocyanate as the staring material, 1.8 g of (RS)-N-[2-oxo-2-(2-phenyl-1-pyrrolidinyl)ethyl]-2-[3-(3-methylphenyl)ureido]-N-phenylacetamide melting at 152° C are obtained after recrystallization from an ethyl acetate/cyclohexane mixture (50/50 by volume).

(RS)-2-Amino-N-[2-oxo-2-(2-phenyl-1-pyrrolidinyl)ethyl]-N-phenylacetamide may be prepared in a manner analogous to that described in Example 106 for the preparation of 2-amino-N-[2-(8-azaspiro[4,5]-decan-8-yl)-2-oxoethyl]-N-phenylacetamide, but using 2.8 g of (RS)-N-[2-oxo-2-(2-phenyl-1-pyrrolidinyl)ethyl]-N-phenyl-2-phthalimidoacetamide and 0.6 g of hydrazine hydrate as the starting material. 1.8 g of (RS)-2-amino-N-[2-oxo-2-(2-phenyl-1-pyrrolidinyl)ethyl]-N-phenylacetamide are thus obtained in the form of an oil which is used as such in the subsequent syntheses.

(RS)-N-[2-oxo-2-(2-phenyl-1-pyrrolidinyl)ethyl]-N-phenyl-2-phthalimidoacetamide may be prepared in a manner analogous to that described in Example 106 for the preparation of N-[2-(8-azaspiro[4,5]-decan-8-yl)-2-oxoethyl]-N-phenyl-2-phthalimidoacetamide, but using 4.0 g of 2-(N-phenyl-2-phthalimidoacetamido)acetic acid, 1.65 g of oxalyl dichloride and 3.5 g of (RS)-2-phenylpyrrolidine as the starting material. The crude product obtained is purified by chromatography on 70 g of silica (0.065–0.200 mm) contained in a column 2.5 cm in diameter [eluent: ethyl acetate/cyclohexane (75/25 by volume)], collecting 20 cm³ fractions. Fractions 8 to 14 are combined and concentrated to dryness under reduced pressure (2.7 kPa) at 40° C. 2.8 g of (RS)-N-[2-oxo-2-(2-phenyl-1-pyrrolidinyl)ethyl]-N-phenyl-2-phthalimidoacetamide are thus obtained in the form of a meringue which is used as such in the subsequent syntheses.

(RS)-2-Phenylpyrrolidine may be prepared by the method described by A. Etienne and Y. Correia, Bull. Soc. Chim. Fr., 3704 (1969).

EXAMPLE 113

The procedure is analogous to that described in Example 106, but 5.0 g of 2-(2-amino-N-phenylacetamido)-N-(4-(dimethylamino)phenyl)-N-methylacetamide and 1.95 g of 3-methylphenyl isocyanate are used as the starting material. After recrystallization from acetonitrile, 1.7 g of N-(4-(dimethylamino)phenyl)-N-methyl-2-{2-[3-(3-methylphenyl)ureido]-N-phenylacetamido}acetamide melting at 190° C are obtained.

2-(2-Amino-N-phenylacetamido)-N-(4-(dimethylamino)phenyl)-N-methylacetamide may be prepared in a manner analogous to that described in Example 106 for the preparation of 2-amino-N-[2-(8-azaspiro[4,5]decan-8-yl)-2-oxoethyl]-N-phenylacetamide, but using 8.6 g of N-(4-(dimethylamino)phenyl)-N-methyl-2-(N-phenyl-2-phthalimidoacetamido)acetamide and 1.8 g of hydrazine hydrate as the starting material. 5.0 g of 2-(2-amino-N-phenylacetamido)-N-(4-(dimethylamino)phenyl)-N-methylacetamide are thus obtained in the form of an oil which is used as such in the subsequent syntheses.

N-(4-(Dimethylamino)phenyl)-N-methyl-2-(N-phenyl-2-phthalimidoacetamido)acetamide may be prepared in a manner analogous to that described in Example 106 for the preparation of N-[2-(8-azaspiro[4,5]decan-8-yl)-2-oxoethyl]-N-phenyl-2-phthalimidoacetamide, but using 8.4 g of 2-(N-phenyl-2-phthalimidoacetamido)acetic acid, 3.4 g of oxalyl dichloride and 8.0 g of 4-(dimethylamino)-N-methylaniline as the starting material. After recrystallization from an ethyl acetate/cyclohexane mixture (50/50 by volume), 8.6 g of N-(4-(dimethylamino)phenyl)-N-methyl-2-(N-phenyl-2-phthalimidoacetamido)acetamide melting at 190° C are obtained.

4-(Dimethylamino)-N-methylaniline may be prepared in the following way: a solution of 9.4 g of 4-(dimethylamino)formanilide in 80 cm³ of anhydrous tetrahydrofuran is added in the course of 15 minutes to a suspension of 4.04 g of lithium aluminium hydride in 100 cm³ of anhydrous tetrahydrofuran, stirred at a temperature close to 25° C. The mixture is stirred at a temperature close to 25° C for 3 hours. After cooling to a temperature close to 5° C, 4.6 cm³ of water, 3.4 cm³ of a 5N aqueous sodium hydroxide solution and then 15.5 cm³ of water are added successively. The suspension obtained is stirred for 30 minutes and 150 cm³ of diethyl ether are added. The insoluble product is separated off by filtration and the filtrate is concentrated to dryness under reduced pressure (2.7 kPa) at 40° C. The residue is dissolved in 60 cm³ of dichloromethane and the organic phase is dried over magnesium sulphate and concentrated to dryness under reduced pressure (2.7 kPa) at 40° C. 8 g of 4-(dimethylamino)-N-methylaniline are thus obtained in the form of an oil which is used as such in the subsequent syntheses.

4-(Dimethylamino)formanilide may be prepared in the following way: 13.6 g of 4-(dimethylamino)aniline are added to a solution of 10.8 g of sodium methylate in 100 cm³ of anhydrous dimethylformamide. The mixture is heated under reflux for 2 hours, distilling the methanol formed, and then concentrated to dryness under reduced pressure (0.1 kPa) at 60° C. The residue is taken up in 1 liter of water and 300 cm³ of diethyl ether. The organic phase is separated off by settling, dried over magnesium sulphate and concentrated to dryness under reduced pressure (2.7 kPa) at 30° C. 9.4 g of 4-(dimethylamino)formanilide melting at 105° C are thus obtained.

EXAMPLE 114

Following a procedure analogous to that described in Example 106, but using 1.0 g of 2-amino-N-[2-(8-aza-1,4-dioxaspiro[4,5]decan-8-yl)-2-oxoethyl]-N-phenylacetamide and 0.4 g of 3-methylphenyl isocyanate as the starting material, 0.6 g of N-[2-(8-aza-1,4-dioxaspiro[4,5]decan-8-yl)-2-oxoethyl]-2-[3-(3-methylphenyl)ureido]-N-phenylacetamide melting at 130° C is obtained after recrystallization from a cyclohexane/ethyl acetate mixture (50/50 by volume).

2-Amino-N-[2-(8-aza-1,4-dioxaspiro[4,5]decan-8-yl)-2-oxoethyl]-N-phenylacetamide may be prepared in a manner analogous to that described in Example 106 for the preparation of 2-amino-N-[2-(8-azaspiro[4,5]decan-8-yl)-2-oxoethyl]-N-phenylacetamide, but using 2.7 g of N-[2-(8-aza-1,4-dioxaspiro[4,5]decan-8-yl)-2-oxoethyl]-N-phenyl-2-phthalimidoacetamide and 0.58 g of hydrazine hydrate as the starting material. 1.0 g of 2-amino-N-[2-(8-aza-1,4-dioxaspiro[4,5]decan-8-yl)-2-oxoethyl]-N-phenylacetamide is thus obtained in the form of an oil which is used as such in the subsequent syntheses.

N-[2-(8-Aza-1,4-dioxaspiro[4,5]decan-8-yl)-2-oxoethyl]-N-phenyl-2-phthalimidoacetamide may be prepared in the following way: 5.3 g of N,N'-diimidazolecarbonyl are added to a suspension of 10 g of 2-(N-phenyl-2-phthalimidoacetamido)acetic acid in 100 cm³ of anhydrous tetrahydrofuran. The mixture is stirred at a temperature close to 25° C for 3 hours and 4.75 g of 8-aza-1,4-dioxaspiro[4,5]decane are then added. The mixture is stirred at a temperature close to 25° C for 15 hours. The insoluble product is separated off by filtration and the filtrate is concentrated to dryness under reduced pressure (2.7 kPa) at 40° C. The residue is purified by chromatography on 70 g of silica (0.065–0.200 mm) contained in a column 2.5 cm in diameter [eluent: ethyl acetate], collecting 50 cm³ fractions. Fractions 5 to 9 are combined and concentrated to dryness under reduced pressure (2.7 kPa) at 40° C. After recrystallization from an ethyl acetate/diisopropyl ether mixture (50/50 by volume), 2.7 g of N-[2-(8-aza-1,4-dioxaspiro[4,5]decan-8-yl)-2-oxoethyl]-N-phenyl-2-phthalimidoacetamide melting at 200° C are obtained.

EXAMPLE 115

The procedure is analogous to that described in Example 74, but 2.5 g of ethyl 3-{3-{N-[N-(2-fluorophenyl)-N-methylcarbamoylmethyl]-N-phenylcarbamoylmethyl}ureido}benzoate and 4.9 cm³ of a 1N aqueous sodium hydroxide solution are used as the starting material. After recrystallization from an ethyl acetate/dimethylformamide mixture (90/10 by volume), 0.5 g of 3-{3-{N-[N-(2-fluorophenyl)-N-methylcarbamoylmethyl]-N-phenylcarbamoylmethyl}ureido}benzoic acid melting at 250° C is obtained.

Ethyl 3-{3-{N-[N-(2-fluorophenyl)-N-methylcarbamoylmethyl]-N-phenylcarbamoylmethyl}ureido}benzoate may be prepared in a manner analogous to that described in Example 72 for the preparation of ethyl 3-{3-[N-(N-methyl-N-phenylcarbamoylmethyl]-N-phenylcarbamoylmethyl]ureido}benzoate but using 11.6 g of N-(2-fluorophenyl)-2-{2-[(1-imidazolyl)carboxamido]-N-phenylacetamido}-N-methylacetamide and 9.2 g of ethyl 3-aminobenzoate as the starting material. The crude product obtained is purified by chromatography on 100 g of silica (0.065–0.200 mm) contained in a column 5 cm in diameter [eluent: methylene chloride/ethyl acetate (40/60 by volume)], collecting 20 cm³ fractions. Fractions 6 to 10 are combined and concentrated to dryness under reduced pressure (2.7 kPa) at 40° C. 2.5 g of ethyl 3-{3-{N-[N-(2-fluorophenyl)-N-methylcarbamoylmethyl]-N-phenylcarbamoylmethyl-}ureido}benzoate melting at about 105° C are thus obtained.

N-(2-Fluorophenyl)-2-{2-[(1-imidazolyl)carboxamido]-N-phenylacetamido}-N-methylacetamide may be prepared in a manner analogous to that described in Example 29 for the preparation of 2-{2-[(1-imidazolyl)carboxamido]-N-phenylacetamido}-N-methyl-N-phenylacetamide but using 9.4 g of 2-(2-amino-N-phenylacetamido)-N-(2-fluorophenyl)-N-methylacetamide and 7.3 g of N,N'-diimidazolecarbonyl as the starting material. 11.6 g of N-(2-fluorophenyl)-2-{2-[(1-imidazolyl)carboxamido]-N-phenylacetamido}-N-methylacetamide are thus obtained in the form of an oil which is used as such in the subsequent syntheses.

EXAMPLE 116

The procedure is analogous to that described in Example 72, but 3.1 g of 2-{2-[(1-imidazolyl)carboxamido]-N-phenylacetamido}-N-methyl-N-phenylacetamide and 7.0 g of tetra-n-butylammonium 3-amino-benzylsulphonate are used as the starting material. The crude product obtained is dissolved in 30 cm³ of acetone and a solution of 2.45 g of potassium nonafluorobutanesulphonate in 10 cm³ of acetone is added. The insoluble product is separated off by filtration, washed with twice 3 cm³ of acetone and air-dried. After recrystallization from ethanol, 0.7 g of potassium 3-{3-[N-(N-methyl-N-phenylcarbamoylmethyl)-N-phenylcarbamoylmethyl]ureido}benzylsulphonate melting at 194° C is obtained.

Tetra-n-butylammonium 3-aminobenzylsulphonate may be prepared in a manner analogous to that described in Example 99 for the preparation of methyl (RS)-3-aminomandelate, but using 11.6 g of tetra-n-butylammonium 3-nitrobenzylsulphonate and 0.3 g of 5% palladium-on-charcoal as the starting material. 10.5 g of tetra-n-butylammonium 3-aminobenzylsulphonate are thus obtained in the form of an oil which is used as such in the subsequent syntheses.

Tetra-n-butylammonium 3-nitrobenzylsulphonate may be prepared in the following way: 6.9 g of sodium 3-nitrobenzylsulphonate and then 9.9 g tetra-n-butylammonium hydrogen sulphonate are added to 800 cm³ of a 0.5M aqueous potassium dihydrogen phosphate solution. The mixture is extracted with 500 cm³ of methylene chloride. The organic phase is dried over magnesium sulphate and concentrated to dryness under reduced pressure (2.7 kPa) at 40° C. 13 g of tetra-n-butylammonium 3-nitrobenzylsulphonate are thus obtained in the form of an oil which is used as such in the subsequent syntheses.

Sodium 3-nitrobenzylsulphonate may be prepared by the method described by Purgotti and Monti, Gaz. Chim. Ital., 30, II, 247.

EXAMPLE 117

The procedure is analogous to that described in Example 74, but 0.7 g of methyl (RS)-2-{3-{3-[N-(N-methyl-N-phenylcarbamoylmethyl)-N-phenylcarbamoylmethyl]ureido}phenyl}propionate and 1.3 cm³ of a 1N aqueous sodium hydroxide solution are used as the starting material. The crude product obtained is dissolved in 4 cm³ of a 1N aqueous sodium hydroxide solution. The solution is filtered and then acidified to pH 1 using a 1N aqueous hydrochloric acid solution. The insoluble product is separated off by filtration, washed with 5 times 2 cm³ of water and air-dried. 0.5 g of (RS)-2-{3-{3-[N-(N-methyl-N-phenylcarbamoylmethyl)-N-phenylcarbamoylmethyl]ureido}phenyl}propionic acid melting at 140° C is thus obtained.

Methyl (RS)-2-{3-{3-[N-(N-methyl-N-phenylcarbamoylmethyl)-N-phenylcarbamoylmethyl]ureido}phenyl}propionate may be prepared in a manner analogous to that described in Example 72 for the preparation of ethyl 3-{3-[N-(N-methyl-N-phenylcarbamoylmethyl)-N-phenylcarbamoylmethyl]ureido}benzoate, but using 1.1 g of 2-{2-[(1-imidazolyl)carboxamido]-N-phenylacetamido}-N-methyl-N-phenylacetamide and 1.0 g of methyl (RS)-2-(3-aminophenyl) propionate as the starting material. The crude product is purified by chromatography on 50 g of silica (0.065–0.200 mm) contained in a column 2.5 cm in diameter [eluent: methylene chloride/ethyl acetate (60/40) by volume)], collecting 25 cm³ fractions. Fractions 5 to 13 are combined and concentrated to dryness under reduced pressure (2.7 kPa) at 40° C. 0.7 g of methyl (RS)-2-{3-{3-[N-(N-methyl-N-phenylcarbamoylmethyl)-N-phenylcarbamoylmethyl]-ureido}phenyl}propionate melting at 184° C is thus obtained.

Methyl (RS)-2-(3-aminophenyl)propionate may be prepared in a manner analogous to that described in Example 99 for the preparation of methyl (RS)-3-aminomandelate, but using 4 g of methyl (RS)-2-(3-nitrophenyl)propionate and 0.3 g of 5% palladium-on-charcoal as the starting material. 3.3 g of methyl (RS)-2-(3-aminophenyl)propionate are thus obtained in the form of an oil which is used as such in the subsequent syntheses.

Methyl (RS)-2-(3-nitrophenyl)propionate may be prepared in the following way: hydrochloric acid is bubbled for 3 hours into a solution of 5 g of (RS)-2-(3-nitrophenyl)propionitrile in 40 cm³ of methanol. The mixture obtained is stirred under reflux for 30 minutes and the insoluble product is separated off by filtration. The filtrate is concentrated to dryness under reduced pressure (2.7 kPa) at 40° C. The crude product is purified by chromatography on 80 g of silica (0.065–0.200 mm) contained in a column 3.5 cm in diameter [eluent: petroleum ether/ethyl acetate (80/20 by volume)], collecting 100 cm³ fractions. Fractions 1 and 2 are combined and concentrated to dryness under reduced pressure (2.7 kPa) at 40° C. 4.0 g of methyl (RS)-2-(3-nitrophenyl)propionate are thus obtained in the form of an oil which is used as such in the subsequent syntheses.

(RS)-2-(3-Nitrophenyl)propionitrile may be prepared by the method described by E. Felder et al., J. Med. Chem., 13, 559 (1970).

EXAMPLE 118

The procedure is analogous to that described in Example 72, but 1.6 g of 2-{2-[(1-imidazolyl)carboxamido]-N-phenylacetamido}-N-methyl-N-phenylacetamide and 1.2 g of 5-amino-2-methoxyphenylmethanol are used as the starting material. The crude product obtained is purified by chromatography on 50 g of silica (0.065–0.20 mm) contained in a column 3 cm in diameter [eluent: methylene chloride/ethanol (95/5 by volume)], collecting 20 cm³ fractions. Fractions 21 to 29 are combined and concentrated to dryness under reduced pressure (2.7 kPa) at 40° C. After recrystallization from acetonitrile, 0.82 g of 2-{2-[3-(3-hydroxymethyl-4-methoxyphenyl)ureido]-N-phenylacetamido}-N-methyl-N-phenylacetamide melting at 181° C is thus obtained.

5-Amino-2-methoxyphenylmethanol may be prepared in a manner analogous to that described in Example 99 for the preparation of methyl (RS)-3-aminomandelate, but using 3 g of 2-methoxy-5-nitrophenylmethanol and 0.5 g of 5% palladium-on-charcoal as the starting material. 1.2 g of 5-amino-2-methoxyphenylmethanol are thus obtained in the form of a meringue which is used as such in the subsequent syntheses.

2-Methoxy-5-nitrophenylmethanol may be prepared in the following way: 2.0 g of an oily suspension (50% by weight) of sodium hydride are added in the course of 10 minutes to a solution of 9.3 g of 2-hydroxy-5-nitrophenylmethanol in 110 cm³ of anhydrous dimethylformamide. The mixture obtained is stirred at a temperature close to 25° C for 30 minutes and 7.8 g of methyl iodide are then added in the course of 10 minutes. The mixture is stirred for 2 hours at a temperature close to 25° C, then poured into 500 cm³ of water and extracted with 3 times 150 cm³ of ethyl acetate. The combined organic phases are dried over magnesium sulphate and concentrated to dryness under reduced pressure (2.7 kPa) at 35° C. After recrystallization from ethyl acetate, 8 g of 2-methoxy-5-nitrophenylmethanol melting at 124° C are obtained.

2-Hydroxy-5-nitrophenylmethanol may be prepared in the following way: 2.0 g of sodium borohydride are added in the course of 10 minutes to a solution of 10 g of 2-hydroxy-5-nitrobenzaldehyde in 300 cm³ of ethanol. The mixture is stirred for 12 hours at a temperature close to 25° C and then poured into 200 cm³ of a 1N aqueous hydrochloric acid solution. The solution obtained is concentrated to about 200 cm³ under reduced pressure (2.7 kPa) at 40° C and then extracted with twice 100 cm³ of ethyl acetate. The combined organic phases are dried over magnesium sulphate and concentrated to dryness under reduced pressure (2.7 kPa) at 40° C. 8.5 g of 2-hydroxy-5-nitrophenylmethanol melting at 126° C are thus obtained.

EXAMPLE 119

The procedure is analogous to that described in Example 74, but 1.3 g of methyl 2-methoxy-5-{3-[N-(N-methyl-N-phenylcarbamoylmethyl)-N-phenylcarbamoylmethyl]ureido}benzoate and 2.6 cm³ of a 1N aqueous sodium hydroxide solution are used as the starting material. The solution is filtered and then acidified to pH 1 using a 1N aqueous hydrochloric acid solution. The insoluble product is separated off by filtration, washed with 5 times 2 cm³ of water and air-dried. 0.53 g of 2-methoxy-5-{3-[N-(N-methyl-N-phenylcarbamoylmethyl)-N-phenylcarbamoylmethyl]ureido}benzoic acid melting at 165° C is thus obtained.

Methyl 2-methoxy-5-{3-[N-(N-methyl-N-phenylcarbamoylmethyl)-N-phenylcarbamoylmethyl]ureido}benzoate may be prepared in a manner analogous to that described in Example 72 for the preparation of ethyl 3-{3-[N-(N-methyl-N-phenylcarbamoylmethyl)-N-phenylcarbamoylmethyl]ureido}benzoate, but using 2.35 g of 2-{2-[(1-imidazolyl)carboxamido]-N-phenylacetamido}-N-methyl-N-phenylacetamide and 2.2 g of methyl 5-amino-2-methoxybenzoate as the starting material. The crude product is purified by chromatography on 150 g of silica (0.065–0.200 mm), contained in a column 4.0 cm in diameter [eluent: methylene chloride/ethanol (95/5 by volume)], collecting 30 cm³ fractions. Fractions 14 to 30 are combined and concentrated to dryness under reduced pressure (2.7 kPa) at 40° C. After recrystallization from ethyl acetate, 1.3 g of methyl-2-methoxy-5-{3-[N-(N-methyl-N-phenylcarbamoylmethyl)-N-phenylcarbamoylmethyl]ureido} benzoate melting at 140° C are obtained.

Methyl 5-amino-2-methoxybenzoate may be prepared in a manner analogous to that described in Example 99 for the preparation of methyl (RS)-3-aminomandelate, but using 20 g of methyl 2-methoxy-5-nitrobenzoate and 0.5 g of 5% palladium-on-charcoal as the starting material. 17 g of methyl 5-amino-2-methoxybenzoate are thus obtained in the form of an oil which is used as such in the subsequent syntheses.

Methyl 2-methoxy-5-nitrobenzoate may be prepared in the following way: 25 g of methyl 2-chloro-5-nitrobenzoate are added to a solution of 7.3 g of sodium methylate in 600 cm³ of methanol. The mixture is stirred under reflux for 3 hours and then run into 1000 cm³ of a 0.1N aqueous hydrochloric acid solution. The insoluble product is separated off by filtration, washed with 5 times 60 cm³ of water and air-dried. 19.7 g of methyl 2-methoxy-5-nitrobenzoate melting at 99° C are thus obtained.

Methyl 2-chloro-5-nitrobenzoate may be prepared in the following way: 80 cm³ of methanol and 16 cm³ of methanesulphonic acid are added to a solution of 30.1 g of 2-chloro-5-nitrobenzoic acid in 580 cm³ of 1,2-dichloroethane. The mixture is stirred under reflux for 12 hours and then at a temperature close to 25° C for 12 hours. The solution is washed with twice 200 cm³ of water, twice 150 cm³ of a saturated aqueous sodium bicarbonate solution and twice 150 cm³ of water and then dried over magnesium sulphate and concentrated to dryness under reduced pressure (2.7 kPa) at 35° C. 31 g of methyl 2-chloro-5-nitrobenzoate melting at 70° C are thus obtained.

EXAMPLE 120

The procedure is analogous to that described in Example 74, but 1.5 g of methyl 2-chloro-5-{3-[N-(N-methyl-N-phenylcarbamoylmethyl)-N-phenylcarbamoylmethyl]ureido}benzoate and 2.9 cm³ of a 1N aqueous sodium hydroxide solution are used as the starting material. The crude product obtained is dissolved in 24 cm³ of a 0.1N aqueous sodium hydroxide solution. The solution is washed with 20 cm³ of ethyl acetate and acidified to pH 1 using a 1N aqueous hydrochloric acid solution. The insoluble product is washed with 5 times 2 cm³ of water and air-dried. 0.8 g of 2-chloro-5-{3-[N-(N-methyl-N-phenylcarbamoylmethyl)-N-phenylcarbamoylmethyl]ureido}benzoic acid melting at 240° C. is thus obtained.

Methyl 2-chloro-5-{3-[N-(N-methyl-N-phenylcarbamoylmethyl)-N-phenylcarbamoylmethyl]ureido} benzoate may be prepared in a manner analogous to that described in Example 72 for the preparation of ethyl 3-{3-[N-(N-methyl-N-phenylcarbamoylmethyl)-N- phenylcarbamoylmethyl]ureido}benzoate, but using 2.1 g of 2-{2-[(1-imidazolyl)carboxamido]-N-phenylacetamido}-N-methyl-N-phenylacetamide and 2.0 g of methyl 5-amino-2-chlorobenzoate as the starting material. The crude product obtained is purified by chromatography on 60 g of silica (0.065–0.200 mm) contained in a column 3 cm in diameter [eluent: cyclohexane/ethyl acetate (30/70 by volume)], collecting 30 cm³ fractions. Fractions 12 to 23 are combined and concentrated to dryness under reduced pressure (2.7 kPa) at 40° C. 1.5 g of methyl 2-chloro-5-{3-[N-(N-methyl-N-phenylcarbamoylmethyl)-N-phenylcarbamoylmethyl]ureido}benzoate melting at 210° C. are thus obtained.

Methyl 5-amino-2-chlorobenzoate may be prepared in the following way: 80 cm³ of water, 4.17 cm³ of an 11.9N aqueous hydrochloric acid solution and 4.2 g of iron powder are added to a suspension of 6 g of methyl 2-chloro-5-nitrobenzoate in 800 cm³ of ethanol. The mixture is stirred under reflux for 4 hours and the insoluble product is then separated off by filtration and washed with 100 cm³ of methylene chloride. The filtrate is concentrated to about 100 cm³ washed with 3 times 50 cm³ of ethyl acetate, rendered alkaline to pH 7 using a saturated aqueous sodium bicarbonate solution and extracted with 3 times 50 cm³ of diethyl ether. The combined organic phases are dried over magnesium sulphate and concentrated to dryness under reduced pressure (2.7 kPa) at 30° C. 2 g of methyl 5-amino-2-chlorobenzoate are thus obtained in the form of an oil which is used as such in the subsequent syntheses.

EXAMPLE 121

The procedure is analogous to that described in Example 74, but 1.6 g of methyl 2-methoxy-5-{3-[N-(N-methyl-N-phenylcarbamoylmethyl)-N-phenylcarbamoylmethyl]ureido}phenylacetate and 3.1 cm³ of a 1N aqueous sodium hydroxide solution are used as the starting material. The crude product obtained is dissolved in 8 cm³ of a 1N aqueous sodium hydroxide solution. The solution is washed with 10 cm³ of ethyl acetate and filtered and the filtrate is acidified to pH 1 using a 1N aqueous hydrochloric acid solution. The insoluble product is washed with 5 times 2 cm³ of water and air-dried. 1.1 g of 2-methoxy-5-{3-[N-(N-methyl-N-phenylcarbamoylmethyl)-N-phenylcarbamoylmethyl]ureido}phenylacetic acid melting at 130° C. are thus obtained.

Methyl 2-methoxy-5-{3-[N-(N-methyl-N-phenylcarbamoylmethyl)-N-phenylcarbamoylmethyl]ureido}phenylacetate may be prepared in a manner analogous to that described in Example 72 for the preparation of ethyl 3-{3-[N-(N-methyl-N-phenylcarbamoylmethyl)-N-phenylcarbamoylmethyl]ureido}benzoate, but using 2.2 g of 2-{2-[(1-imidazolyl)carboxamido]-N-phenylacetamido}-N-methyl-N-phenylacetamide and 2.6 g of methyl 5-amino-2-methoxyphenylacetate as the starting material. The crude product obtained is purified by chromatography on 70 g of silica (0.065–0.200 mm) contained in a column 3 cm in diameter [eluent: methylene chloride/ethyl acetate (65/35 by volume)], collecting 25 cm³ fractions. Fractions 18 to 33 are combined and concentrated to dryness under reduced pressure (2.7 kPa) at 40° C. 1.7 g of methyl 2-methoxy-5-{3-[N-(N-methyl-N-phenylcarbamoylmethyl)-N-phenylcarbamoyl-methyl]ureido}phenylacetate are thus obtained in the form of a meringue which is used as such in the subsequent syntheses.

Methyl 5-amino-2-methoxyphenylacetate may be prepared in a manner analogous to that described in Example 99 for the preparation of methyl (RS)-3-aminomandelate, but using 3.1 g of methyl 2-methoxy-5-nitrophenylacetate and 0.3 g of 5% palladium-on-charcoal as the starting material. 2.2 g of methyl 5-amino-2-methoxyphenylacetate are thus obtained in the form of an oil which is used as such in the subsequent syntheses.

Methyl 2-methoxy-5-nitrophenylacetate may be prepared in the following way: hydrochloric acid is bubbled for 3 hours through a solution of 4 g of 2-methoxy-5-nitrophenylacetonitrile in 40 cm³ of methanol. The mixture obtained is stirred under reflux for 1 hour and then for 12 hours at a temperature close to 25° C. The insoluble product is separated off by filtration, washed with 5 times 10 cm³ of water and air-dried. 3.2 g of methyl 2-methoxy-5-nitrophenylacetate melting at 92° C. are thus obtained.

2-Methoxy-5-nitrophenylacetonitrile may be prepared in the following way: 10 cm³ of a 3.5M potassium cyanide solution are added to a solution of 6.2 g of 2-methoxy-5-nitrobenzyl bromide in 60 cm³ of methanol. The mixture is stirred under reflux for 4 hours and then concentrated to dryness under reduced pressure. The residue obtained is taken up in 100 cm³ of diethyl ether and 100 cm³ of water. The organic phase is dried over magnesium sulphate and then concentrated to dryness under reduced pressure (2.7 kPa) at 35° C. The crude product obtained is purified by chromatography on 40 g of silica (0.065–0.200 mm) contained in a column 3 cm in diameter (eluent: methylene chloride), collecting 20 cm³ fractions. Fractions 3 to 8 are combined and concentrated to dryness under reduced pressure (2.7 kPa) at 40° C. 4.2 g of 2-methoxy-5-nitrophenylacetonitrile melting at 100° C. are thus obtained.

2-Methoxy-5-nitrobenzyl bromide may be prepared in the following way: 13.9 g of carbon tetrabromide and then 8.9 g of triphenylphosphine are added in the course of 10 min to a solution of 5.2 g of 2-methoxy-5-nitrophenylmethanol in 150 cm³ of acetonitrile. The mixture is stirred for 1 hour at a temperature close to 20° C. and then concentrated to dryness under reduced pressure (2.7 kPa) at 40° C. The crude product obtained is purified by chromatography on 25 g of silica (0.065–0.200 mm) contained in a column 4.0 cm in diameter [eluent: methylene chloride/petroleum ether (40/60 by volume)], collecting 125 cm³ fractions. Fractions 5 to 12 are combined and concentrated to dryness under reduced pressure (2.7 kPa) at 40° C. 5.6 g of 2-methoxy-5-nitrobenzyl bromide melting at 78° C. are thus obtained.

EXAMPLE 122

The procedure is analogous to that described in Example 81, but 1 g of (RS)-2-amino-N-[2-oxo-2-(2-phenylpiperidino)ethyl]-N-phenylacetamide and 0.38 g of 3-methylphenyl isocyanate are used as the starting material. After recrystallization from an ethyl acetate/diethyl ether mixture (60/40 by volume), 0.9 g of (RS)-2-[3-(3-methylphenyl)ureido]-N-[2-oxo-2-(2-phenylpiperidino)ethyl]-N-phenylacetamide melting at 125° C. is thus obtained.

(RS)-2-Amino-N-[2-oxo-2-(2-phenylpiperidino)ethyl]-N-phenylacetamide may be prepared in a manner analogous to that described in Example 2 for the preparation of 2-(2-amino-N-phenylacetamido)-N-methyl-N-phenylacetamide, but using 15.7 g of (RS)-N-[2-oxo-2-(2-phenylpiperidino)ethyl]-N-phenyl-2- phthalimidoacetamide and 3.2 g of hydrazine hydrate as the starting material. 8.6 g of (RS)-2-amino-N-[2-oxo-2-(2-phenylpiperidino)ethyl]-N-phenylacetamide are thus obtained in the form of an oil which is used as such in the subsequent syntheses.

(RS)-N-[2-Oxo-2-(2-phenylpiperidino)ethyl]-N-phenyl-2-phthalimidoacetamide may be prepared in a manner analogous to that described in Example 2 for the preparation of N-methyl-N-phenyl-2-(N-phenyl-2-phthalimidoacetamido)acetamide, but using 13.5 g of 2-(N-phenyl-2-phthalimidoacetamido)acetic acid, 5.1 g of oxalyl dichloride, 2.6 g of pyridine and 5.9 g of (RS)-2-phenylpiperidine as the starting material. 15.8 g of (RS)-N-[2-oxo-2-(2-phenylpiperidino)ethyl]-N-phenyl-2-phthalimidoacetamide are thus obtained in the form of a meringue which is used as such in the subsequent syntheses.

(RS)-2-Phenylpiperidine may be prepared by the method described by C. G. Overberger and L. P. Herin, J. Org. Chem., 22, 417 (1962).

EXAMPLE 123

The procedure is analogous to that described in Example 72, but 1.1 g of (RS)-2-[(1-imidazolyl)carboxamido]-N-[2-oxo-2-(2-phenylpiperidino)ethyl]-N-phenylacetamide and 0.55 g of 3-hydroxymethylaniline are used as the starting material. The crude product is purified by chromatography on 50 g of silica (0.065–0.200 mm) contained in a column 2.5 cm in diameter [eluent: methylene chloride/ethyl acetate (40/60 by volume)], collecting 40 cm³ fractions. Fractions 7 to 11 are combined and concentrated to dryness under reduced pressure (2.7 kPa) at 40° C. After recrystallization from an ethyl acetate/diisopropyl ether mixture (20/80 by volume), 0.7 g of (RS)-2-[3-(3-hydroxymethylphenyl)ureido]-N-[2-oxo-2-(2-phenylpiperidino)ethyl]-N-phenylacetamide melting at 104° C. is obtained.

(RS)-2-[(1-Imidazolyl)carboxamido]-N-[2-oxo-2-(2-phenylpiperidino)ethyl]-N-phenylacetamide may be prepared in a manner analogous to that described in Example 72 for the preparation of 2-{2-[(1-imidazolyl)carboxamido]-N-phenylacetamido}-N-methyl-N-phenylacetamide, but using 7.5 g of (RS)-2-amino-N-[2-oxo-2-(2-phenylpiperidino)ethyl]-N-phenylacetamide and 5.2 g of N,N'-diimidazolecarbonyl as the starting material. 7.3 g of (RS)-N-[2-oxo-2-(3,3-dimethylpiperidino)ethyl]-N-phenyl-2-phthalimidoacetamide are thus obtained in the form of a meringue which is used as such in the subsequent syntheses.

EXAMPLE 124

The procedure is analogous to that described in Example 74, but 0.6 g of ethyl (RS)-3-{3-{N-2-oxo-2-(2-phenylpiperidino)ethyl]-N-phenylcarbamoylmethyl}ureido}phenylacetate and 1.1 cm³ of a 1N sodium hydroxide solution are used as the starting material. The product is dissolved in 3 cm³ of a 1N aqueous sodium hydroxide solution. The solution is filtered and then acidified with 3 cm³ of a 1N aqueous hydrochloric acid solution. The insoluble product is separated off by filtration, washed with 5 times 2 cm³ of water and air-dried. 0.5 g of (RS)-3-{3-{N-[2-oxo-2-(2-phenylpiperidino)ethyl]-N-phenylcarbamoylmethyl}ureido}phenylacetic acid melting at 135° C. is thus obtained.

Ethyl (RS)-3-{3-[N-[2-oxo-2-(2-phenylpiperidino)ethyl]-N-phenylcarbamoylmethyl}ureido}phenylacetate may be prepared in a manner analogous to that described in Example 72 for the preparation of ethyl 3-[N-(N-methyl-N-phenylcarbamoylmethyl)-N-phenylcarbamoylmethyl]benzoate, but using 1.3 g of (RS)-2-[(1-imidazolyl)carboxamido]-N-[2-oxo-2-(2-phenylpiperidino)ethyl]-N-phenylacetamide and 1 g of ethyl 3-aminophenylacetate as the starting material. The crude product obtained is purified by chromatography on 80 g of silica (0.065–0.200 mm) contained in a column 3 cm in diameter [eluent: methylene chloride/ethyl acetate (70/30 by volume)], collecting 30 cm³ fractions. Fractions 11 to 38 are combined and concentrated to dryness under reduced pressure (2.7 kPa) at 40° C. 0.8 g of ethyl (RS)-3-{3-{N-[2-oxo-2-(2-phenylpiperidino)ethyl]-N-phenylcarbamoylmethyl}ureido}phenylacetate is thus obtained in the form of a meringue which is used as such in the subsequent syntheses.

EXAMPLE 125

The procedure is analogous to that described in Example 74, but 0.9 g of ethyl 3-{3-[N-(2-oxo-2-thiomorpholinoethyl)-N-phenylcarbamoylmethyl]ureido}benzoate and 1.9 cm³ of a 1N aqueous sodium hydroxide solution are used as the starting material. The crude product obtained is dissolved in 5 cm³ of a 1N aqueous sodium hydroxide solution. The solution is filtered and then acidified to pH 1 using a 1N aqueous hydrochloric acid solution. The insoluble product is separated off by filtration, washed with 5 times 2 cm³ of water and air-dried. 0.6 g of 3-{3-[N-(2-oxo-2-thiomorpholinoethyl)-N-phenylcarbamoylmethyl]ureido}benzoic acid melting at 280° C. is thus obtained.

Ethyl 3-{3-[N-(2-oxo-2-thiomorpholinoethyl)-N-phenylcarbamoylmethyl]ureido}benzoate may be prepared in a manner analogous to that described in Example 72 for the preparation of ethyl 3-{3-[N-(N-methyl-N-phenylcarbamoylmethyl)-N-phenylcarbamoylmethyl]ureido}benzoate, but using 1.5 g of 2-[(1-imidazolyl)carboxamido]-N-(2-oxo-2-thiomorpholinoethyl)-N-phenylacetamide and 1.3 g of ethyl 3-aminobenzoate as the starting material. The crude product obtained is purified by chromatography on 70 g of silica (0.065–0.200 mm) contained in a column 3 cm in diameter [eluent: methylene chloride/ethyl acetate (50/50 by volume)], collecting 30 cm³ fractions. Fractions 1 and 2 are combined and concentrated to dryness under reduced pressure (2.7 kPa) at 40° C. 2.5 g of ethyl 3-{3-[N-(2-oxo-2-thiomorpholinoethyl)-N-phenylcarbamoylmethyl]ureido}benzoate melting at 183° C. are thus obtained.

2-[(1-Imidazolyl)carboxamido]-N-(2-oxo-2-thiomorpholinoethyl)-N-phenylacetamide may be prepared in a manner analogous to that described in Example 29 for the preparation of 2-{2-[(1-imidazolyl)carboxamido]-N-phenylacetamido}-N-methyl-N-phenylacetamide, but using 1.8 g of 2-amino-N-(2-oxo-2-thiomorpholinoethyl)-N-phenylacetamide and 3.7 g of N,N'-diimidazolecarbonyl as the starting material. 1.5 g of 2-[(1-imidazolyl)carboxamido]-N-(2-oxo-2-thiomorpholinoethyl)-N-phenylacetamide are thus obtained in the form of a meringue which is used as such in the subsequent syntheses.

2-Amino-N-(2-oxo-2-thiomorpholinoethyl)-N-phenylacetamide may be prepared in a manner analogous to that described in Example 2 for the preparation of 2-(2-amino-N-phenylacetamido)-N-methyl-N-phenylacetamide, but using 4.8 g of N-(2-oxo-2-thiomorpholinoethyl)-N-phenyl-2-phthalimidoacetamide and 1.1 g of hydrazine hydrate as the starting material.

1.8 g of 2-amino-N-(2-oxo-2-thiomorpholinoethyl)-N-phenylacetamide are thus obtained in the form of an oil which is used as such in the subsequent syntheses.

N-(2-Oxo-2-thiomorpholinoethyl)-N-phenyl-2-phthalimidoacetamide may be prepared in a manner analogous to that described in Example 2 for the preparation of N-methyl-N-phenyl-2-(N-phenyl-2-phthalimidoacetamido)acetamide, but using 4.9 g of 2-(N-phenyl-2-phthalimidoacetamido)acetic acid, 2.0 g of oxalyl dichloride and 3.0 g of thiomorpholine as the starting material. 5.9 g of N-(2-oxo-2-thiomorpholinoethyl)-N-phenyl-2-phthalimidoacetamide are thus obtained in the form of an oil which is used as such in the subsequent syntheses.

EXAMPLE 126

The procedure is analogous to that described in Example 81, but 0.7 g of 2-amino-N-[2-(2,2-dimethylthiomorpholino)-2-oxoethyl]-N-phenylacetamide and 0.28 g of 3-methylphenyl isocyanate are used as the starting material. After recrystallization from an ethyl acetate/acetonitrile mixture (80/20 by volume), 0.6 g of N-[2-(2,2-dimethylthiomorpholino)-2-oxoethyl]-2-[3-(3-methylphenyl)ureido]-N-phenylacetamide melting at 186° C. is obtained.

2-Amino-N-[2-(2,2-dimethylthiomorpholino)-2-oxoethyl]-N-phenylacetamide may be prepared in a manner analogous to that described in Example 2 for the preparation of 2-(2-amino-N-phenylacetamido)-N-methyl-N-phenylacetamide, but using 8.0 g of N-[2-(2,2-dimethylthiomorpholino)-2-oxoethyl]-N-phenyl-2-phthalimidoacetamide and 1.77 g of hydrazine hydrate as the starting material. 4.4 g of 2-amino-N-[2-(2,2-dimethylthiomorpholino)-2-oxoethyl]-N-phenylacetamide are thus obtained in the form of an oil which is used as such in the subsequent syntheses.

N-[2-(2,2-Dimethylthiomorpholino)-2-oxoethyl]-N-phenyl-2-phthalimidoacetamide may be prepared in a manner analogous to that described in Example 2 for the preparation of N-methyl-N-phenyl-2-(N-phenyl-2-phthalimidoacetamido)acetamide, but using 7.0 g of 2-(N-phenyl-2-phthalimidoacetamido)acetic acid, 2.9 g of oxalyl dichloride, 2.1 g of pyridine and 3.5 g of 2,2-dimethylthiomorpholine as the starting material. 8.1 g of N-[2-(2,2-dimethylthiomorpholino)-2-oxoethyl]-N-phenyl-2-phthalimidoacetamide are thus obtained in the form of an oil which is used as such in the subsequent syntheses.

2,2-Dimethylthiomorpholine may be prepared by the method described by J. McManus et al., J. Med. Chem., 766 (1965).

EXAMPLE 127

The procedure is analogous to that described in Example 74, but 1.3 g of ethyl 3-{3-{N-[2-(2,2-dimethylthiomorpholino)-2-oxoethyl]-N-phenylcarbamoylmethyl}ureido}benzoate and 2.5 cm³ of a 1N aqueous sodium hydroxide solution are used as the starting material. The crude product obtained is dissolved in 5 cm³ of a 1N aqueous sodium hydroxide solution. The solution is filtered and then acidified to pH 1 using a 1N aqueous hydrochloric acid solution. The insoluble product is separated off by filtration, washed with 5 times 2 cm³ of water and air-dried. 0.6 g of 3-{3-{N-[2-(2,2-dimethylthiomorpholino)-2-oxoethyl]-N-phenylcarbamoylmethyl}ureido}benzoic acid melting at 275° C. is thus obtained.

Ethyl 3-{3-{N-[2-(2,2-dimethylthiomorpholino)-2-oxoethyl]-N-phenylcarbamoylmethyl}ureido}benzoate may be prepared in a manner analogous to that described in Example 72 for the preparation of ethyl 3-{3-[N-(N-methyl-N-phenylcarbamoylmethyl)-N-phenylcarbamoylmethyl]ureido}benzoate but using 2.0 g of N-[2-(2,2-dimethylthiomorpholino)-2-oxoethyl]-2-[(1-imidazolyl)carboxamido]-N-phenylacetamide and 1.6 g of ethyl 3-aminobenzoate as the starting material. The crude product obtained is purified by chromatography on 60 g of silica (0.065–0.200 mm) contained in a column 3 cm in diameter [eluent: methylene chloride/ethyl acetate (60/40 by volume)], collecting 25 cm³ fractions. Fractions 9 to 25 are combined and concentrated to dryness under reduced pressure (2.7 kPa) at 40° C. 1.3 g of ethyl 3-{3-{N-[2-(2,2-dimethylthiomorpholino)-2-oxoethyl]-N-phenylcarbamoylmethyl}ureido}benzoate are thus obtained in the form of a meringue which is used as such in the subsequent syntheses.

N-[2-(2,2-Dimethylthiomorpholino)-2-oxoethyl]-2-[(1-imidazolyl)carboxamido]-N-phenylacetamide may be prepared in a manner analogous to that described in Example 29 for the preparation of 2-{2-[(1-imidazolyl)carboxamido]-N-phenylacetamido}-N-methyl-N-phenylacetamide, but using 3.6 g of 2-amino-N-[2-(2,2-dimethylthiomorpholino)-2-oxoethyl]-N-phenylacetamide and 2.7 g of N,N'-diimidazolecarbonyl as the starting material. 4.3 g of N-[2-(2,2-dimethylthiomorpholino)-2-oxoethyl]-2-[(1-imidazolyl)carboxamido]-N-phenylacetamide are thus obtained in the form of a meringue which is used as such in the subsequent syntheses.

EXAMPLE 128

0.56 g of hydroxylamine hydrochloride is added to a solution of 0.65 g of sodium methylate in 15 cm³ of methanol. The mixture is stirred for 30 minutes at a temperature close to 25° C. and a solution of 2 g of ethyl 3-{3-{N-[N-(2-fluorophenyl)-N-methylcarbamoylmethyl]-N-phenylcarbamoylmethyl}ureido}benzoate in 10 cm³ of methanol is then added. The mixture is stirred under reflux for 2 hours and then for 12 hours at 25° C. The insoluble product is separated off by filtration. The filtrate is acidified to pH 1 using a 0.1N hydrochloric acid solution and then extracted with twice 50 cm³ of ethyl acetate. The combined organic phases are dried over magnesium sulphate and then concentrated to dryness under reduced pressure (2.7 kPa) at 40° C. The crude product obtained is purified by chromatography on 40 g of silica (0.065–0.200 mm) contained in a column 1.5 cm in diameter [eluent: ethyl acetate/methanol (9/10 by volume)], collecting 20 cm³ fractions. Fractions 5 to 10 are combined and concentrated to dryness under reduced pressure (2.7 kPa) at 40° C. After recrystallization from acetonitrile, 0.3 g of 3-{3-{N-[N-(2-fluorophenyl)-N-methylcarbamoylmethyl]-N-phenylcarbamoylmethyl}ureido}benzenecarbohydroxamic acid melting at 220° C. is obtained.

EXAMPLE 129

The procedure is analogous to that described in Example 72, but 0.65 g of 2-{2-[(1-imidazolyl)carboxamido]-N-phenylacetamido}-N-methyl-N-phenylacetamide and 0.5 g of (E)-3-(3-aminophenyl)-prop-2-en-1-ol are used as the starting material. The crude product obtained is purified by chromatography on 40 g of silica (0.065–0.200 mm) contained in a column 2 cm in diameter [eluent: methylene chloride/ethyl acetate (50/50 by volume)], collecting 10 cm³ fractions. Fractions 8 to 15 are combined and concentrated to dryness under reduced pressure (2.7 kPa) at 40° C. After recrystallization from an ethyl acetate/diisopropyl ether mixture (15/85 by volume), 0.45 g of (E)-2-{2-{3-[3-(3-hydroxypropen-1-yl)phenyl]ureido}-N-phenylacetamido}-N-methyl-N-phenylacetamide melting at 120° C. is obtained.

(E)-3-(3-Aminophenyl)prop-2-en-1-ol may be prepared in the following way: 1 g of lithium aluminium hydride is added in the course of 10 minutes to a solution of 1.7 g of ethyl (E)-3-aminocinnamate in 75 cm³ of diethyl ether kept at a temperature close to −15° C. The suspension obtained is stirred at a temperature close to −10° C. for 2 hours and 1.2 cm³ of water, 0.85 cm³ of a 5N aqueous sodium hydroxide solution and 3.9 cm³ of water are then added. The insoluble product is separated off by filtration and the filtrate is concentrated to dryness under reduced pressure (2.7 kPa) at 30° C. The crude product obtained is purified by chromatography on 35 g of silica (0.065–0.200 mm) contained in a column 2.0 cm in diameter (eluent: ethyl acetate), collecting 20 cm³ fractions. Fractions 6 to 10 are combined and concentrated to dryness under reduced pressure (2.7 kPa) at 40° C. After recrystallization from ethyl acetate, 0.5 g of (E)-3-(3-aminophenyl)prop-2-en-1-ol) melting at 85° C. is obtained.

EXAMPLE 130

The procedure is analogous to that described in Example 72, but 1.7 g of 2-{2-[(1-imidazolyl)carboxamido]-N-phenylacetamido}-N-methyl-N-phenylacetamide and 1.5 g of 5-(3-aminobenzyl)tetrazole are used as the starting material. The crude product obtained is purified by chromatography on 50 g of silica (0.065–0.200 mm) contained in a column 3 cm in diameter [eluent: methylene chloride/ethanol (90/10 by volume)], collecting 20 cm³ fractions. Fractions 1 and 2 are combined and concentrated to dryness under reduced pressure (2.7 kPa) at 40° C. After recrystallization from an acetonitrile/diisopropyl ether mixture (50/50 by volume), 0.4 g of N-methyl-N-phenyl-2-{2-{3-{3-[(5-tetrazolyl)methyl]phenyl}ureido}-N-phenylacetamido}acetamide melting at 206° C. is obtained.

5-(3-Aminobenzyl)tetrazole may be prepared in the following way: 0.3 g of 5% palladium-on-charcoal is added to a solution of 3.9 g of 5-(3-nitrobenzyl)tetrazole in 80 cm³ of ethanol. The suspension is stirred for 2 hours at a temperature close to 25° C. under a hydrogen atmosphere (100 kPa). The catalyst is then separated off by filtration and the filtrate is concentrated to dryness under reduced pressure (2.7 kPa) at 40° C. 3.1 g of 5-(3-aminobenzyl)tetrazole melting at 140° C. is thus obtained.

5-(3-Nitrobenzyl)tetrazole may be prepared in the following way: 1.43 g of sodium nitride and 1.17 g of anhydrous ammonium chloride are added to a solution of 1.6 g of 3-nitrophenylacetonitrile in 25 cm³ of anhydrous dimethylformamide. The mixture is stirred at a temperature close to 100° C. for 22 hours and then concentrated to dryness under reduced pressure (1.2 kPa) at 80° C. The residue obtained is taken up with 25 cm³ of a 2N hydrochloric acid solution and the mixture is extracted with twice 50 cm³ of methylene chloride. The combined organic phases are dried over magnesium sulphate and concentrated to dryness under reduced pressure (2.7 kPa) at 35° C. 1.6 g of 5-(3-nitrobenzyl)tetrazole melting at 140° C. are thus obtained.

3-Nitrophenylacetonitrile may be prepared in the following way: 20 cm³ of an 8.5M aqueous potassium cyanide solution are added to a solution of 20.6 g of 3-nitrobenzyl chloride in 120 cm³ of methanol. The mixture is stirred under reflux for 4 hours and then concentrated to dryness under reduced pressure (2.7 kPa) at 45° C. The residue is taken up in 200 cm³ of diethyl ether and 150 cm³ of water. The organic phase is dried over magnesium sulphate and concentrated to dryness under reduced pressure (2.7 kPa) at 35° C. The crude product obtained is purified by chromatography on 50 g of silica (0.065–0.200 mm) contained in a column 2 cm in diameter (eluent: methylene chloride), collecting 30 cm³ fractions. Fractions 4 to 9 are combined and concentrated to dryness under reduced pressure (2.7 kPa) at 40° C. 11 g of 3-nitrophenylacetonitrile melting at 60° C. are thus obtained.

EXAMPLE 131

The procedure is analogous to that described in Example 74, but 0.4 g of methyl 2-hydroxyimino-2-{3-{3-[N-(N-methyl-N-phenylcarbamoylmethyl)-N-phenylcarbamoylmethyl]ureido}phenyl}acetate, form A, and 7.7 cm³ of a 0.1N aqueous sodium hydroxide solution are used as the starting material. The product obtained is dissolved in 2 cm³ of a 1N aqueous sodium hydroxide solution and filtered and the filtrate is then acidified to pH 1 using a 4N aqueous hydrochloric acid solution. The insoluble product is separated off by filtration, washed with 3 times 1 cm³ of water and air-dried. 0.35 g of 2-hydroxyimio-2-{3-{3-[N-(N-methyl-N-phenylcarbamoylmethyl)-N-phenylcarbamoylmethyl]ureido}phenyl}acetic acid, form A, melting at 158° C. is thus obtained.

Forms A and B of methyl 2-hydroxyimino-2-{3-{3-[N-(N-methyl-N-phenylcarbamoylmethyl)-N-phenylcarbamoylmethyl]ureido}phenyl}acetate may be prepared in the following way: 0.14 g of pyridine and then 0.15 g of hydroxylamine hydrochloride in solution in 2.5 cm³ of water are added to a solution of 0.9 g of methyl 3-{3-[N-(N-methyl-N-phenylcarbamoylmethyl)-N-phenylcarbamoylmethyl]ureido}phenylglyoxylate in 5 cm³ of methanol. The mixture is heated under reflux for 3 hours and run into 25 cm³ of water. The insoluble product is separated off by filtration, washed with 3 times 2 cm³ of water and purified by chromatography on 20 g of silica (0.065–0.200 mm) contained in a column 2.0 cm in diameter [eluent: methylene chloride/ethyl acetate (50/50 by volume)], collecting 10 cm³ fractions. Fractions 5 to 10 are combined and concentrated to dryness under reduced pressure (2.7 kPa) at 40° C. 0.4 g of methyl 2-hydroxyimino-2-{3-{3-[N-(N-methyl-N-phenylcarbamoylmethyl)-N-phenylcarbamoylmethyl]ureido}phenyl}acetate, form A, is thus obtained in the form of a meringue which is used as such in the subsequent syntheses. Fractions 22 to 30 are combined and concentrated to dryness under reduced pressure (2.7 kPa) at 40° C. 0.3 g of methyl 2-hydroxyimino-2-{3-{3-[N-(N-methyl-N-phenylcarbamoylmethyl)-N-phenylcarbamoylmethyl]ureido}phenyl}acetate, form B, is thus obtained in the form of a meringue which is used as such in the subsequent syntheses.

EXAMPLE 132

The procedure is analogous to that described in Example 74, but 0.3 g of methyl 2-hydroxyimino-2-{3-{3-[N-(N-methyl-N-phenylcarbamoylmethyl)-N-phenylcarbamoylmethyl]ureido}phenyl}acetate, form B, and 5.8 cm$^3$ of a 0.1N aqueous sodium hydroxide solution are used as the starting material. The crude product obtained is dissolved in 2 cm$^3$ of a 1N aqueous sodium hydroxide solution and filtered and the filtrate is then acidified to pH 1 using a 4N aqueous hydrochloric acid solution. The insoluble product is separated off by filtration, washed with 3 times 0.5 cm$^3$ of water and air-dried. 0.1 g of 2-hydroxyimino-2-{3-{3-[N-(N-methyl-N-phenylcarbamoylmethyl)-N-phenylcarbamoylmethyl]ureido}phenyl}acetic acid, form B, melting at 220° C. is thus obtained.

EXAMPLE 133

0.47 g of triethylamine and 1.32 g of trifluoromethanesulphonic anhydride are added to a solution of 1.7 g of 2-{2-[3-(3-aminophenyl)ureido]-N-phenylacetamido}-N-methyl-N-phenylacetamide in 25 cm$^3$ of methylene chloride. The mixture is stirred for 18 hours at a temperature close to 25° C., diluted with 30 cm$^3$ of methylene chloride and washed with 3 times 50 cm$^3$ of water. The organic phase is dried over magnesium sulphate, concentrated to dryness under reduced pressure (2.7 kPa) at 35° C. and purified by chromatography on 50 g of silica (0.065–0.200 mm) contained in a column 2.5 cm in diameter [eluent: methylene chloride/methanol (95/5 by volume)], collecting 30 cm$^3$ fractions. Fractions 10 to 20 are combined and concentrated to dryness under reduced pressure (2.7 kPa) at 40° C. After recrystallization from ethyl acetate, 0.32 g of N-methyl-N-phenyl-2-{2-[3-(3-trifluoromethylsulphamoylphenyl)ureido]-N-phenylacetammido}acetamide melting at 232° C. is obtained.

EXAMPLE 134

The procedure is analogous to that described in Example 74, but 1.0 g of ethyl 3-{3-[N-(N-methyl-N-phenylcarbamoylmethyl)-N-phenylcarbamoylmethyl]ureido}phenylthioacetate and 1.9 cm$^3$ of a 1N aqueous sodium hydroxide solution are used as the starting material. The crude product obtained is dissolved in 30 cm$^3$ of a 1N aqueous sodium hydroxide solution. The solution is washed with 30 cm$^3$ of ethyl acetate and filtered and the filtrate is acidified to pH 1 using a 1N aqueous hydrochloric acid solution. The insoluble product is washed with 5 times 2 cm$^3$ of water and air-dried. 0.65 g of 3-{3-[N-(N-methyl-N-phenylcarbamoylmethyl)-N-phenylcarbamoylmethyl]ureido}phenylthioacetic acid melting at 185° C. is thus obtained.

Ethyl 3-{3-[N-(N-methyl-N-phenylcarbamoylmethyl)-N-phenylcarbamoylmethyl]ureido}phenylthioacetate may be prepared in a manner analogous to that described in Example 72 for the preparation of 3-{3-[N-(N-methyl-N-phenylcarbamoylmethyl)-N-phenylcarbamoylmethyl]ureido}benzoate, but using 1.44 g of 2-{2-[(1-imidazolyl)carboxamido]-N-phenylacetamido}-N-methyl-N-phenylacetamide and 1.6 g of ethyl 3-aminophenylthioacetate as the starting material. The crude product obtained is purified by chromatography on 50 g of silica (0.065–0.200 mm) contained in a column 2.5 cm in diameter [eluent: methylene chloride/ethanol (95/5 by volume)], collecting 50 cm$^3$ fractions. Fractions 11 to 17 are combined and concentrated to dryness under reduced pressure (2.7 kPa) at 40° C. 1.0 g of ethyl 3-{3-[N-(N-methyl-N-phenylcarbamoylmethyl)-N-phenylcarbamoylmethyl]ureido}phenylthioacetate melting at 120° C. is thus obtained.

Ethyl 3-aminophenylthioacetate may be prepared in the following way: 16.7 g of ethyl bromoacetate are added in the course of 5 minutes to a solution of 12.5 g of 3-aminothiophenol in 200 cm$^3$ of ethanol. The mixture is stirred at a temperature close to 20° C. for 3 hours and then concentrated to dryness under reduced pressure (2.7 kPa) at 40° C. The product obtained is dissolved in a mixture of 100 cm$^3$ of ethyl acetate and 100 cm$^3$ of a 1N aqueous sodium hydroxide solution. The organic phase is separated off, washed with twice 50 cm$^3$ of water, dried over magnesium sulphate and concentrated to dryness under reduced pressure (2.7 kPa) at 40° C. The product obtained is purified by chromatography on 250 g of silica (0.065–0.200 mm) contained in a column 5 cm in diameter [eluent: ethyl acetate/cyclohexane (70/30 by volume)], collecting 20 cm$^3$ fractions. Fractions 12 to 19 are combined and concentrated to dryness under reduced pressure (2.7 kPa) at 40° C. 13 g of ethyl 3-aminophenylthioacetate are thus obtained in the form of an oil which is used as such in the subsequent syntheses.

The present invention also relates to medicaments comprising at least one compound of formula (I) or a salt of a compound of this type in the pure state or in the form of a composition in which it is associated with any other pharmaceutically compatible product, which may be inert or physiologically active. The medicaments according to the invention may be employed by oral, parenteral or rectal administration or topical application.

Solid compositions for oral administration which may be used are tablets, pills, powders (gelatine capsules, cachets) or granules. In these compositions, the active ingredient according to the invention is mixed with one or more inert diluents, such as starch, cellulose, sucrose, lactose or silica, under a stream of argon. These compositions may also comprise substances other than the diluents, for example one or more lubricants such as magnesium stearate or talc, a colorant, a coating (coated tablets) or a glaze.

Liquid compositions for oral administration which may be used are pharmaceutically acceptable solutions, suspensions, emulsions, syrups and elixirs containing inert diluent such as water, ethanol, glycerol, vegetable oils or paraffin oil. These compositions may comprise substances other than the diluents, for example wetting compounds, sweeteners, thickeners, flavorings or stabilizers.

Sterile compositions for parenteral administration may preferably be aqueous or non-aqueous solutions, suspensions or emulsions. As solvent or vehicle it is possible to employ water, propylene glycol, a polyethylene glycol, vegetable oils, in particular olive oil, injectable organic esters, for example ethyl oleate, or other suitable organic solvents. These compositions may also contain adjuvants, in particular wetting agents, agents for rendering isotonic, emulsifiers, dispersing agents and stabilizers. The sterilization may be effected in various ways, for example by aseptising filtration, by incorporating sterilizing agents into the composition, by irradiation or by heating. They may also be prepared in the form of sterile solid compositions which may be dissolved at the time of use in sterile water or any other injectable sterile medium.

The compositions for rectal administration are suppositories or rectal capsules which contain, in addition to the active compound, excipients such as cacao butter, semisynthetic glycerides or polyethylene glycols.

The compositions for topical application may be, for example, creams, lotions, eye lotions, mouth washes, nasal drops or aerosols.

In human therapy, the compounds according to the invention are particularly useful for the treatment and the prevention of disorders associated with CCK and gastrin in the nervous system and the gastrointestinal system. These compounds may therefore be used in the treatment and the prevention of psychoses, anxiety disorders, Parkinson's disease, tardive dyskinesia, irritable colon syndrome, acute pancreatitis, ulcers and disorders of the intestinal motility, and certain tumors of the lower oesophagus, the colon and the intestine, as a booster for the analgesic activity of narcotic and non-narcotic analgesic medicaments and as an appetite regulator.

The doses depend on the desired effect, the duration of the treatment and the mode of administration used; they are generally between 0.05 g and 1 g per day administered orally for an adult, with single doses ranging from 10 mg to 500 mg of active substance.

In general, the physician will determine the appropriate posology as a function of the age, the weight and all other factors inherent to the subject to be treated. The following examples illustrate compositions according to the invention:

Example A

Capsules containing 50 mg of active compound and having the following composition are prepared using the customary technique:

| | |
|---|---|
| (E)-2-{2-{3-[3-(l-hydroxyiminoethyl)phenyl]-ureido}-N-phenylacetamido}-N-methyl-N-phenyl-acetamide | 50 mg |
| cellulose | 18 mg |
| lactose | 55 mg |
| colloidal silica | 1 mg |
| sodium carboxymethyl starch | 10 mg |
| talc | 10 mg |
| magnesium stearate | 1 mg |

Example B

Tablets containing 50 mg of active compound and having the following composition are prepared by the customary technique:

| | |
|---|---|
| 2-{2-[3-(3-hydroxymethylphenyl)ureido]-N-phenyl-acetamido}-N-methyl-N-phenylacetamide | 50 mg |
| lactose | 104 mg |
| cellulose | 40 mg |
| polyvidone | 10 mg |
| sodium carboxymethyl starch | 22 mg |
| talc | 10 mg |
| magnesium stearate | 2 mg |
| colloidal silica | 2 mg |
| mixture of hydroxymethyl cellulose, glycerol and titanium oxide (72-3.5-24.5) q.s. 1 complete 245-mg coated tablet | |

Example C

An injectable solution containing 10 mg of active compound and having the following composition is prepared:

| | |
|---|---|
| 3-{3-[N-(N-methyl-N-phenylcarbamoylmethyl)-N-phenylcarbamoylmethyl]ureido}benzoic acid | 50 mg |
| benzoic acid | 80 mg |
| benzyl alcohol | 0.06 cm$^3$ |
| sodium benzoate | 80 mg |
| 95% ethanol | 0.4 cm$^3$ |
| sodium hydroxide | 24 mg |
| propylene glycol | 1.6 cm$^3$ |
| water q.s. | 4 cm$^4$ |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Compounds of formula:

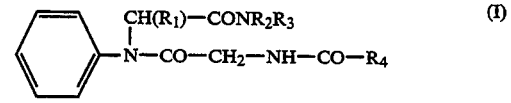

in which $R_1$ represents a hydrogen atom, an alkyl alkoxycarbonyl or a phenyl radical, or a phenyl radical substituted by at least one substituent chosen from halogen atoms, alkyl, alkoxy, alkylthio, nitro and amino radicals, $R_2$ represents a hydrogen atom or an alkyl radical, or an alkyl radical substituted by an alkoxycarbonyl radical, $R_3$ represents an alkyl, phenylalkyl, indanyl, cycloalkylalkyl, phenyl, or phenyl substituted by at least one substituent chosen from halogen atoms, alkyl, alkoxy, alkylthio and dialkylamino radicals, or quinolyl radical, or $R_2$ and $R_3$ form together with the nitrogen atom to which they are attached a saturated or unsaturated monocyclic or polycyclic heterocycle containing 4 to 9 carbon atoms and at least one heteroatom chosen from O, N, and S and which is unsubstituted or substituted by at least one alkyl, alkoxycarbonyl, dialkylcarbamoyl, phenyl or alkoxy radical or, in combination with a carbon atom of the heterocycle, a monocyclic spiro ring having 4 or 5 members and which optionally contains at least one heteroatom, chosen from, $R_4$ represents a phenyl radical, or a phenyl radical substituted by at least one substituent chosen from halogen atoms, alkyl, alkoxy, alkylthio radicals, naphthyl, indolyl, quinolyl radical or a phenylamino and phenylene in which the phenyl ring is substituted by at least one substituent chosen from halogen atoms, alkyl, alkoxy, alkylthio, hydroxyl, nitro, amino, acyl, cyano, sulphamoyl, trifluoromethylsulphonamido, carbamoyl, benzoyl, carboxyl, alkoxycarbonyl, phenylhydroxymethyl, piperidino, hydroxyiminoalkyl, alkoxyiminoalkyl, hydroxyaminocarbonyl, alkoxyaminocarbonyl, 5-tetrazolyl, 5-terazolylalkyl, alkylsulphinyl, monohydroxyalkyl or polyhydroxyalkyl, sulpho, —alk—O—CO—alk, —alk—O—alk, —alk—COOX, —O—alk—COOX, —alk'—COOX, —CH=CH—COOX, —CO—COOX, —alk—SO$_3$H, —CH=CH—alk', —C(=NOH)—COOX and —S—alk—COOX radicals, X represents a hydrogen atom or an alkyl radical, alk represents an alkyl or alkylene radical, and alk' represents a hydroxyalkylene or hydroxyalkyl radical, with the exception of compounds in which $R_1$ represents a hydrogen atom, $R_2$ and $R_3$ each represent an alkyl radical or $R_2$ and $R_3$ form, with the nitrogen atom to which they are attached, a 1-pyrrolidinyl radical unsubstituted or substituted by an alkyl radical and $R_4$ represents a naphthyl or indolyl radical or a phenylamino radical in which the phenyl ring is unsubstituted or substituted by an alkyl, alkoxy, nitro, hydroxyl or alkylthio radical or by one or two halogen atoms, with the proviso that the acyl radicals contain 2 to 4 carbon atoms, the alkyl, alkylene and alkoxy radicals and the alkyl, alkylene and alkoxy moieties containing 1 to 4 carbon atoms in a straight or branched chain and the cycloalkyl radicals contain 3 to 6 carbon atoms, as well as the racemates and enantiomers thereof when they contain at least one asymmetric center and the salts thereof.

2. Compound of formula (I) according to claim 1, wherein $R_2$ and $R_3$ represent with the nitrogen atom to which they are attached a heterocycle chosen from the piperidino, or piperidino substituted by at least one alkyl, alkoxycarbonyl, phenyl or dialkylcarbamoyl radical, 1-perhydroazepinyl, 1,2,3,6-tetrahydro-1-pyridyl, 1,2,3,4-tetrahydro-1-quinolyl, 1-pyrrolidinyl, 3,4-dihydro-1,4-2H-benzoxazin-4-yl, 3,4-dihydro-1,4-2H-benzothiazin-4-yl, N-alkyl-1,2,3,4-tetrahydro-1-quinoxalinyl, 1-perhydroquinolyl, 1,2,3,4-tetrahydro-2-isoquinolyl, 8-azaspiro[(4,5]-decan-8-yl, 2- or 3-phenyl-1-pyrrolidinyl, 8-aza-1,4-dioxaspiro[(4,5])decan-8-yl, thiomorpholino, or thiomorpholino substituted by at least one alkyl radical, or 1-indolinyl rings.

3. Compound of formula (I) according to claim 1, wherein $R_1$ represents a hydrogen atom, $R_2$ represents an alkyl radical and $R_3$ represents a phenyl radical, or $R_2$ and $R_3$ form with the nitrogen atom to which they are attached a piperidino radical substituted by at least one alkyl radical or a thiomorpholino radical substituted by at least one alkyl radical, and $R_4$ represents a phenylamino radical in which the phenyl ring is substituted by at least one substituent chosen from the hydroxyl, carboxyl, hydroxyiminoalkyl, —alk—COOH, alkyl, alkylthio, monohydroxyalkyl and —C(=NOH)—COOH radicals as well as the racemates and enantiomers thereof when they contain at least one asymmetric center and the salts thereof.

4. A pharmaceutical composition for the treatment or prevention of disorders associated with CCK and gastrin in the nervous system and the gastrointestinal system comprising an effective amount as active ingredient, at least one compound of formula (I) according to claim 1, together with a pharmaceutically acceptable carrier.

5. A pharmaceutical composition for the treatment or prevention of disorders associated with CCK and gastrin in the nervous system and the gastrointestinal system comprising an effective amount as active ingredient, at least one compound of formula (I) according to claim 2, together with a pharmaceutically acceptable carrier.

6. Method for the treatment or prevention of disorders associated with CCK and gastrin in the nervous system and the gastrointestinal system comprising using the medicament according to claim 4.

7. A pharmaceutical composition for the treatment or prevention of disorders associated with CCK and gastrin in the nervous system and the gastrointestinal system comprising an effective amount as active ingredient, at least one compound of formula (I) according to claim 3 together with a pharmaceutically acceptable carrier.

8. Method for the treatment or prevention of disorders associated with CCK and gastrin in the nervous system and the gastrointestinal system comprising using the medicament according to claim 5.

9. Method for the treatment or prevention of disorders associated with CCK and gastrin in the nervous system and the gastrointestinal system comprising using the medicament according to claim 7.

10. Process for the preparation of compounds of formula (I) according to claim 1, wherein $R_4$ represents an unsubstituted or substituted phenylamino radical, comprising reacting a derivative of formula:

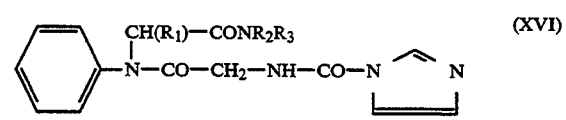

(XVI)

in which $R_1$, $R_2$ and $R_3$ are as defined in claim 1, with an amine of formula:

(XVII)

in which $R_7$ represent a phenyl radical which is unsubstituted or substituted by at least one substituent chosen from halogen atoms, alkyl, alkoxy, alkylthio, hydroxyl, nitro, amino, acyl, cyano, sulphamoyl, trifluoromethylsulphonamido, carbamoyl, benzoyl, carboxyl, alkoxycarbonyl, phenylhydroxymethyl, piperidino, hydroxyiminoalkyl, alkoxyiminoalkyl, 5-tetrazolyl, 5-tetrazolylalkyl, alkylsulphinyl, hydroxyaminocarbonyl, alkoxyaminocarbonyl, monohydroxyalkyl or polyhydroxyalkyl, sulpho, —alk—O—CO—alk, —alk—O—alk, —alk—COOX, —O—alk—COOX, —alk'—COOX, —CH=CH=COOX, —CO—COOX, —alk—SO$_3$H, —CH=CH—alk', —C(=NOH)—COOX and —S—alk—COOX radicals, isolating the product and, optionally, converted to a salt.

* * * * *

UNITED STATES PATENT AND TRADEMARK OFFICE
CERTIFICATE OF CORRECTION

PATENT NO. : 5,382,590

DATED : January 17, 1995

INVENTOR(S) : Jean-Dominique BOURZAT et al.

It is certified that error appears in the above-identified patent and that said Letters Patent is hereby corrected as shown below:

On title page, item [87] PCT Pub. Date:

change "Oct. 22, 1991" to --August 22, 1991--.

Signed and Sealed this

Twenty-fifth Day of April, 1995

Attest:

BRUCE LEHMAN

*Attesting Officer*      *Commissioner of Patents and Trademarks*